(12) United States Patent
Mao et al.

(10) Patent No.: US 7,667,024 B2
(45) Date of Patent: Feb. 23, 2010

(54) OLIGONUCLEOTIDES LABELED WITH A PLURALITY OF FLUOROPHORES

(75) Inventors: Fei Mao, Fremont, CA (US); Xing Xin, Foster City, CA (US)

(73) Assignee: AlleLogic Biosciences Corp., Hayward, CA (US)

(*) Notice: Subject to any disclaimer, the term of this patent is extended or adjusted under 35 U.S.C. 154(b) by 166 days.

(21) Appl. No.: 10/993,625

(22) Filed: Nov. 19, 2004

(65) Prior Publication Data

US 2005/0272053 A1 Dec. 8, 2005

Related U.S. Application Data

(60) Provisional application No. 60/253,263, filed on Nov. 19, 2003.

(51) Int. Cl.
C07H 21/02 (2006.01)
C07H 21/04 (2006.01)
C12Q 1/68 (2006.01)
C12P 19/34 (2006.01)

(52) U.S. Cl. ............... 536/24.3; 536/24.33; 435/6; 435/91.2; 435/975

(58) Field of Classification Search ............ None
See application file for complete search history.

(56) References Cited

U.S. PATENT DOCUMENTS

| | | | |
|---|---|---|---|
| 4,766,062 A | 8/1988 | Diamond | |
| 5,118,605 A * | 6/1992 | Urdea | 435/6 |
| 5,118,801 A | 6/1992 | Lizardi | |
| 5,210,015 A | 5/1993 | Gelfand | |
| 5,268,486 A | 12/1993 | Waggoner | |
| 5,312,728 A | 5/1994 | Lizardi | |
| 5,538,848 A | 7/1996 | Livak | |
| 5,691,146 A * | 11/1997 | Mayrand | 435/6 |
| 5,696,157 A | 12/1997 | Wang | |
| 5,723,591 A | 3/1998 | Livak | |
| 5,800,996 A | 9/1998 | Lee | |
| 5,801,155 A | 9/1998 | Kutyavin | |
| 5,846,726 A * | 12/1998 | Nadeau et al. | 435/6 |
| 5,866,336 A | 2/1999 | Nazarenko | |
| 5,925,517 A | 7/1999 | Tyagi | |
| 6,037,137 A | 3/2000 | Komoriya | |
| 6,117,635 A | 9/2000 | Nazarenko | |
| 6,130,101 A | 10/2000 | Mao | |
| 6,133,445 A | 10/2000 | Waggoner | |
| 6,150,097 A | 11/2000 | Tyagi | |
| 6,174,670 B1 | 1/2001 | Wittwer | |
| 6,258,569 B1 | 7/2001 | Livak | |
| 6,472,153 B1 | 10/2002 | Dempcy et al. | |
| 6,479,303 B1 | 11/2002 | Waggoner | |
| 6,485,901 B1 * | 11/2002 | Gildea et al. | 435/5 |
| 6,486,308 B2 | 11/2002 | Kutyavin | |
| 6,492,346 B1 | 12/2002 | Hedgpeth | |
| 6,545,164 B1 | 4/2003 | Waggoner | |
| 6,573,047 B1 | 6/2003 | Hung et al. | |
| 6,635,427 B2 | 10/2003 | Wittwer | |
| 6,893,868 B2 * | 5/2005 | Packard et al. | 435/325 |
| 2001/0001063 A1 | 5/2001 | Todd | |
| 2002/0006479 A1 | 1/2002 | Sekine | |
| 2002/0077487 A1 | 6/2002 | Leung | |

FOREIGN PATENT DOCUMENTS

| | | | |
|---|---|---|---|
| WO | WO 97/27317 | * | 7/1997 |
| WO | WO 00/13026 A1 | | 3/2000 |

OTHER PUBLICATIONS

Randolph, J.B. et al., Nucl. Acids Res., vol. 25, pp. 2923-2929 (1997).*
Haralambidis, J. et al., Nucl. Acids Res., vol. 15, pp. 4857-4876 (1987).*
Foldes-Papp, Z. et al., J. Biotechnol., vol. 86, pp. 203-224 (2001).*
Stratagene Catalog, p. 39 (1988).*
Hung, S-C. et al., Anal. Biochem., vol. 243, pp. 15-27 (1996).*
Glazer, A. et al., Curr. Opinion Biotechn., vol. 8, pp. 94-102 (1997).*
Zhu, Z. et al., Nucl. Acids Res., vol. 22, pp. 3418-3422 (1994).*
Livak, K.J. et al., PCR Meth. Appl., vol. 4, pp. 357-362 (1995).*
Afonina, Irina et al. "Efficient priming of PCR with short oligonucleotides conjugated to a minor groove binder," *Nucleic Acids Res.*, 1997, pp. 2657-2660, vol. 25, No. 13.
Ahsen, Nicolas von. "Labeled Primers for Mutation Scanning: Making Diagnostic Use of the Nucleobase Quenching Effect," *Clin. Chem.*, 2003, pp. 355-356, vol. 49.
Bernacchi, Serena et al. "Exciton interaction in molecular beacons: a sensitive sensor for short range modifications of the nucleic acid structure," *Nucleic Acids Res.*, 2001, vol. 29, No. 13.
Blackman, Michael et al. "Structural and Biochemical Characterization of a Fluorogenic Rhodamine-Labeled Malarial Protease Substrate," *Biochemistry*, 2002, pp. 12244-12252, vol. 41.
Connolly, Bernard A. et al. "Chemical synthesis of olignucleotides containing a free sulphydryl group and subsequent attachments of thiol specific probes," *Nucleic Acids Res.*, 1985, pp. 4485-4502, vol. 13, No. 12.

(Continued)

*Primary Examiner*—Teresa E Strzelecka
(74) *Attorney, Agent, or Firm*—Wilson Sonsini Goodrich & Rosati

(57) ABSTRACT

An embodiment of the invention discloses new methods for designing labeled nucleic acid probes and primers by labeling oligonucleotides with a plurality of spectrally identical or similar dyes and optionally with one or more quencher dyes. Oligonucleotides labeled in accordance with some embodiments of the invention exhibit a detectable increase in signal, for example, fluorescent signal when the labeling dyes are separated from one another. Methods for separating the dye include cleaving the labeled oligonucleotides include using enzymes that have 5'-exonuclease activity. In one embodiment nucleic acid primers of the present invention may fluoresce upon hybridization to a target sequence and incorporation into the amplification product. Nucleic acid probes and primers of the present invention have wide applications ranging from general detection of a target nucleic acid sequence to clinical diagnostics. Major advantages of the oligonucleotides including nucleic acid probes and primers of many embodiments of the present invention are their synthetic simplicity, spectral versatility and superior fluorescent signal.

42 Claims, 31 Drawing Sheets

OTHER PUBLICATIONS

Cradic, Kendall W., et al. "Substitution of 3'-Phosphate Cap with a Carbon-Based Blocker Reduces the Possibility of Fluorescence Resonance Energy Transfer Probe Failure in Real-Time PCR Assays," *Clin. Chem.*, 2004, pp. 1080-1082, vol. 50.

Dreyer, Geoggrey B. et al. "Sequence-specific cleavage of single-stranded DNA: Oligodeoxynucleotide-EDTA-Fe(II)," *Proc. Natl. Acad. Sci.*, Feb. 1985, pp. 968-972, vol. 82.

Flavell, Andrew J. et al. "A microarray-based high throughput molecular marker genotyping method: the tagged microarray marker (TAM) approach," *Nucleic Acids Res.*, 2003, vol. 31, No. 19.

Geoghegan, Kieran F. "Dye-Pair Reporter Systems for Protein-Peptide Molecular Interactions," *Amer. Chem. Soc.*, Dec. 14, 1999, pp. 71-77, vol. 11, No. 1.

Gloffke, Wendy. "Quantitative PCR Update: Reviewing the latest trends and applications in quantitative, real-time PCR," www.the-scientist.com/yr2003/apr/lcprofile1_030421.html, Date Unknown.

Gundry, Cameron N., et al. "Amplicon Melting Analysis with Labeled Primers: A Closed-Tube Method for Differentiating Homozygotes and Heterozygotes," *Clin. Chem.*, 2003, pp. 396-406, vol. 49, No. 3.

Hawkins, Mary E. et al. "Use of pteridine nucleoside analogs as hybridization probes," *Nucleic Acids Res.*, 2004, vol. 32, No. 7.

He, Junlin et al. "Propynyl groups in duplex DNA: stability of base pairs incorporating 7-substituted 8-aza-7-deazapurines or 5-substituted pyrimidines," *Nucleic Acids Res.*, 2002, pp. 5485-5496, vol. 30, No. 24.

Holland, Pamela M. et al. "Detection of specific polymerase chain reaction product by utilizing the 5' → 3' exonuclease activity of *Thermus aquaticus* DNA polymerase," *Proc. Natl. Acad. Sci. USA*, Aug. 1991, pp. 7276-7280, vol. 88.

Ishiguro, Takahiko et al. "Fluorescence detection of specific sequence of nucleic acids by oxazole yellow-linked oligonucleotides. Homogeneous quantitative monitoring of in vitro transcription," *Nucleic Acids Res.*, 1996, pp. 4992-4997, vol. 24, No. 24.

Johansson, Mary Katherine et al. "Intramolecular Dimers: A New Strategy to Fluorescence Quenching in Dual-Labeled Oligonucleotide Probes," *J. Am. Chem. Soc.*, 2002, pp. 6950-6956, vol. 124, No. 24.

Kalinina, Olga et al. "Nanoliter scale PCR with TaqMan detection," *Nucleic Acids Res.*, 1997, pp. 1999-2004, vol. 25, No. 10.

Khairutdinov, R.F. et al. "Photophysics of Cyanine Dyes: Subnanosecond Relaxation Dynamics in Monomers, Dimers, and H- and J-Aggregates in Solution," *J. Phys. Chem.*, 1997, pp. 2602-2610, vol. 101.

Kumar, Surat et al. "Solution structure of a highly stable DNA duplex conjugated to a minor groove binder," *Nucleic Acids Res.*, 1998, pp. 831-838, vol. 26, No. 3.

Kutyavin, Igor V. et al. "Reduced aggregation and improved specificity of G-rich oligodeioxyribonucleotides containing pyrazolo[3,4-d]pyrimidine guanine bases," *Nucleic Acids Res.*, 2002, pp. 4952-4959, vol. 30, No. 22.

Lee, Linda G. et al. "Allelic discrimination by nick-translation PCR with fluorogenic probes," *Nucleic Acids Res.*, 1993, pp. 3761-3766, vol. 21, No. 16.

Marras, Salvatore A. E. "Efficiencies of fluorescence resonance energy transfer and contact-mediated quenching in oligonucleotides," *Nucleic Acids Res.*, 2002, vol. 30, No. 21.

Mullis, Kary B. et al. "Specific Synthesis of DNA in Vitro via a Polymerase-Catalyzed Chain Reaction," *Methods Enzymol.*, 1987, pp. 335-350, vol. 155.

Mujumdar, Ratnakar B. et al. "Cyanine Dye Labeling Reagents: Sulfoindocyanine Succinimidyl Esters," *Bioconjugate Chem.*, Mar./Apr. 1993, vol. 4, No. 2.

Nazarenko, Irina et al. "Multiplex quantitative PCR using self-quenched primers labeled with a single flourophore," *Nucleic Acids Res.*, 2002, vol. 30, No. 9.

Nelson, Paul S. et al. "A new and versatile reagent for incorporating multiple primary aliphatic amines into synthetic oligonucleotides," *Nucleic Acids Res.*, 1989, pp. 7179-7186, vol. 17, No. 18.

Okamura, Yukio et al. "Double-labeled donor probe can enhance the signal of fluorescence resonance energy transfer (FRET) in detection of nucleic acid hybridization," *Nucleic Acids Res.*, 2000, vol. 28, No. 24.

Packard, Beverly Z. et al. "Profluorescent protease substrates: Intramolecular dimmers described by the exciton model," *Proc. Natl. Acad. Sci.*, Oct. 1996, pp. 11640-11645, vol. 93.

Rohatgi, K.K. et al. "Nature of Bonding in Dye Aggregates," *J. Phys. Chem.*, 1966, pp. 1695-1701, vol. 70, No. 6.

Rudert, W.A., et al. "Double-Labeled Fluorescent Probes for 5' Nuclease Assays: Purification and Performance Evaluation," *BioTechniques*, Jun. 1997, pp. 1140-1145, vol. 22, No. 6.

Saiki, Randall K. et al. "Enzymatic Amplification of β-Globin Genomic Sequences and Restriction Site Analysis for Diagnosis of Sickle Cell Anemia," *Science*, 1985, pp. 1350-1354.

Simeonov, Anton et al. "Single nucleotide polymorphism genotyping using short, fluorescently labeled locked nucleic acid (LNA) probes and fluorescence polarization detection," *Nucleic Acids Res.*, 2002, vol. 30, No. 17.

Sproat, Brian S. et al. "The synthesis of protected 5'-amino-2', 5'-dideoxyribonucleoside-3'-O-phosphoramidites; application of 5'-amino-oligodeoxyribonucleotides," *Nucleic Acids Res.*, 1987, pp. 6181-6196, vol. 15, No. 15.

Stojanovic, Milan N., et al. "Homogeneous assays based on deoxyribozyme catalysis," *Nucleic Acids Res.*, pp. 2915-2918, 2000, vol. 28, No. 15.

Stryer, Lubert et al. "Energy Transfer: A Spectroscopic Ruler," *Proc. Natl. Acad. Sci.*, 1967, pp. 719-726, vol. 58.

Thelwell, Nicola, et al. "Mode of action and application of Scorpion primers to mutation detection," *Nucleic Acids Res.*, pp. 3752-3761, 2000, vol. 28, No. 19.

Tyagi, Sanjay et al. "Molecular Beacons: Probes that Fluoresce upon Hybridization," *Nat. Biotechnol.*, Mar. 1996, pp. 303-308, vol. 14.

"User Bulletin #2, ABI PRISM 7700 Sequence Detection System," Applied Biosystems: A Division of Perkin-Elmer, Dec. 11, 1997.

Vaughn, Cecily P. et al. "Intrinsic Deoxyguanosine Quenching of Fluorescein-Labeled Hybridization Probes: A Simple Method for Real-time PCR Detection and Genotyping," *Laboratory Investigation*, Nov. 2001, pp. 1575-1577, vol. 18, No. 11.

Walter, Nils G. et al. "Fluorescence correlation analysis of probe diffusion simplifies quantitative pathogen detection by PCR," *Proc. Natl. Acad. Sci. USA*, Nov. 1996, pp. 12805-12810, vol. 93.

West, W. et al. "The Dimeric State of Cyanine Dyes," *J. Phys. Chem.*, Jun. 1965, pp. 1894-1903, vol. 69, No. 6.

Whitcombe, David et al. "A homogeneous fluorescence assay for PCR amplicons: its application to real-time, single-tube genotyping," *Clin. Chem.*, 1998, pp. 918-923, vol. 44.

Yamane, Akio. "MagiProbe: a novel fluorescence quenching-based oligonucleotide probe carrying a fluorophore and an intercalator," *Nucleic Acids Res.*, 2002, vol. 30, No. 19.

Zuckerman, Ronald et al. "Efficient methods for attachment of thiol specific probes to the 3'-ends of synthetic oligodeoxyribonucleotides," *Nucleic Acids Res.*, 1987, pp. 5305-5321, vol. 15, No. 13.

Kutyavin, et al. 3'-Minor groove binder-DNA probes increase sequence specificity at PCR extension temperatures. Nucleic Acids Research, 2000; 28(2):655-661.

Piatek, et al. Molecular beacon sequence analysis for detecting drug resistance in *Mycobacterium tuberculosis*. Nature Biotechnology. 1998; 16:359-363.

\* cited by examiner (Details in Example 2)

(Details in Example 3)

(Details in Example 3)

(Details in Example 2)

(Details in Example 4)

(Details in Example 3)

(Details in Example 4)

(Details in Example 5)

(Details in Example 5)

(Details in Example 5)

(Details in Example 6)

(Details in Example 7)

(Details in Example 7)

(Details in Example 8)

(Details in Example 8)

(Details in Example 8)

(Details in Example 8)

(Details in Example 9)

(Details in Example 9)

(Details in Example 10)

(Details in Example 10)

(Details in Example 7)

(Details in Example 10)

(Details in Example 10)

(Details in Example 10)

(Details in Example 10)

(Details in Example 11)

Solid line : CR110 channel
Dash line : R6G channel (Details in Example 12)

Table 1 Sequence Information

| SEQ ID | Seq Name[1] | Length | Type | Sequence Detail[2] |
|---|---|---|---|---|
| 1 | GAPDH F | 19 | primer | 5'-GAAGGTGAAG GTCGGAGTC-3' |
| 2 | GAPDH R | 20 | primer | 5'-GAAGATGGTG ATGGGATTTC-3 |
| 3 | GAPDH P | 19 | probe | 5'-(5-CR110-L$_3$-)CAAGCTTCCC GTTCTCAGC(-L$_1$-5-CR110)-3' |
| 4 | MCG F | 20 | primer | 5'-TCAAGAGGTG CCACGTCTCC-3' |
| 5 | MCG R | 28 | primer | 5'-CTGATCTGTC TCAGGACTCT GACACTGT-3' |
| 6 | MCG P | 23 | probe | 5'-(6-ROX-L$_3$-)CAGCACAACT ACGCAGCGCC TCC(-L$_1$-6-ROX)-3' |
| 7 | MCG P | 23 | probe | 5'-(6-CR110-L$_3$-)CAGCACAACT ACGCAGCGCC TCC(-L$_1$-6-CR110)-3' |
| 8 | GAPDH P | 19 | probe | 5'-(6-JOE-L$_3$-)CAAGCTTCCC GTTCTCAGC(-L$_1$-6-TAMRA)-3' |
| 9 | GAPDH P | 19 | probe | 5'-(5-R6G-L$_3$-)CAAGCTTCCC GTTCTCAGC(-L$_1$-5-R6G)-3' |
| 10 | GAPDH P | 19 | probe | 5'-(5-CR110-L$_3$-)CAAGCTTCCC GTTCTCAGCp-3' |
| 11 | GAPDH P | 19 | probe | 5'-CAAGCTTCCC GTTCTCAGC(-L$_1$-5-CR110)-3' |
| 12 | GAPDH Beacon P | 32 | probe | 5'-(6-CR110-L$_3$-)CCAAGCGGCT GAGAACGGGA AGCTTGGCTT GG(-L$_1$-6-CR110)-3' |
| 13 | GAPDH Beacon P | 32 | probe | 5'-(6-TAMRA-L$_3$-)CCAAGCGGCT GAGAACGGGA AGCTTGGCTT GG(-L$_1$-6-TAMRA)-3' |
| 14 | GAPDH Beacon P | 32 | probe | 5'-(6-ROX-L$_3$-)CCAAGCGGCT GAGAACGGGA AGCTTGGCTT GG(-L$_1$-6-ROX)-3' |
| 15 | GAPDH F1 | 19 | primer | 5'-(5-CR110-L$_3$-)GAAGGTGAAG GTCGGAGT(-L$_2$-5-CR110)C-3' |
| 16 | GAPDH F2 (xG) | 18 | primer | 5'-(5-CR110-L$_3$-)AAGGTGAAGG TCGGAGT(-L$_2$-5-CR110)C-3' |
| 17 | GAPDH R1 | 20 | primer | 5'-(5-CR110-L$_3$-)GAAGATGGTG ATGGGATT(-L$_2$-5-CR110)TC-3' |
| 18 | GAPDH F1 | 19 | primer | 5'-(5-CR110-L$_3$-)GAAGGTGAAG GTCGGAGTC-3' |
| 19 | GAPDH F2 (xG) | 18 | primer | 5-AAGGTGAAGG TCGGAGT(-L$_2$-5-CR110)C-3' |
| 20 | GAPDH F1 | 19 | primer | 5'-GAAGGTGAAG GTCGGAGT(-L$_2$-5-CR110)C-3' |
| 21 | GAPDH P | 19 | probe | 5'-(6-CR110-L$_3$-)CAAGCTTCCC GTTCTCAGC(-L$_1$-6-CR110)-3' |
| 22 | GAPDH P | 19 | probe | 5'-(6-TAMRA-L$_3$-)CAAGCTTCCC GTTCTCAGC(-L$_1$-6-TAMRA)-3' |
| 23 | GAPDH P | 19 | probe | 5'-(6-ROX-L$_3$-)CAAGCTTCCC GTTCTCAGC(-L$_1$-6-ROX)-3' |
| 24 | GAPDH gene | 226 | gene | |
| 25 | MCG gene | 181 | gene | |
| 26 | ER Forward | 19 | primer | 5'-CCACGGACCATGACCATGA-3' |
| 27 | ER Reverse | 18 | primer | 5'-TCTTGAGCTGCGGACGGT-3' |
| 28 | ER Codon10C | 20 | probe | 5'-(6-CR110-L$_3$-)CCAAAGCATCCGGGATGGCC(-L$_1$-6-CR110)-3' |
| 29 | ER Codon10T | 20 | probe | 5'-(5-R6G-L$_3$-)CCAAAGCATCTGGGATGGCC(-L$_1$-5-R6G)-3' |
| 30 | ER Codon10C gene | 106 | gene | |
| 31 | ER Codon10T gene | 106 | gene | |
| 32 | HCV gene | 109 | gene | |
| 33 | HCV Forward | 22 | primer | 5'-GCACGAATCCTAAACCTCAAAA-3' |
| 34 | HCV Reverse | 22 | primer | 5'-GGCAACAAGTAAACTCCACCAA-3' |
| 35 | HCV Probe | 21 | probe | 5'-(6-ROX-L$_3$-)ATCTGACCACCGCCCGGGAAC(-L$_1$-6-ROX)-3' |
| 36 | MCG P | 23 | probe | 5'-(cy5-L$_3$-)CAGCACAACT ACGCAGCGCC TCC(-L$_1$-cy5)-3' |

[1]. Seq Name is used only for identifying unique sequence. Same sequence labeled with different dye has the same Seq Name while label information is shown under Sequence Detail.

[2]. L$_1$ is a 7-carbon branched linker between the amine group and 3' end; L$_2$ is a 10-atom linear linker between a T and the amine group; and L$_3$ is a 6-carbon liner linker between 5' end and the amine group. The structures of the linkers are shown below:

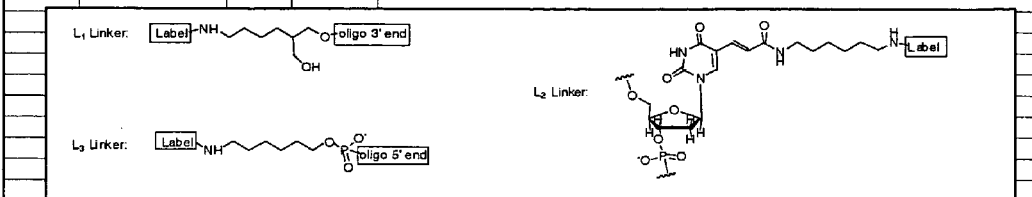

| TABLE 2 Examples of some routes to useful covalent linkages | | |
| --- | --- | --- |
| Electrophilic Group | Nucleophilic Group | Resulting Covalent Linkage |
| activated esters * | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | esters |
| alkyl sulfonates | thiols | thioethers |
| alkyl sulfonates | carboxylic acids | esters |
| alkyl sulfonates | alcohols/phenols | esters |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotrizaines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. succinimidyloxy (—$OC_4H_4O_2$) sulfosuccinimidyloxy (—$OC_4H_3O_2$—$SO_3H$), -1-oxybenzotriazolyl (—$OC_6H_4N_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or —$OCNR^aNHR^b$ where $R^a$ and $R^b$, which may be the same or different, are $C_1$-$C_6$ alkyl, $C_1$-$C_6$ perfluoroalkyl, or $C_1$-$C_6$ alkoxy; or cyclohexyl, 3-dimethylaminopropyl, or N-morpholinoethyl).
**Acyl azides can also rearrange to isocyanates

SEQUENCE LISTING

```
<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gaaggtgaag gtcggagtc                                                  19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gaagatggtg atgggatttc                                                 20

<210> SEQ ID NO 3
<211> LENGTH: 19
<212> TYPE: DNA
<213> ORGANISM: Artificial Sequence
<220> FEATURE:
<223> OTHER INFORMATION: probe 5CR 110 labeled at 5'- and 3'- terminal
      amines

<400> SEQUENCE: 3
```

```
caagcttccc gttctcagc                                                    19
```

```
<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tcaagaggtg ccacgtctcc                                                   20
```

```
<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
ctgatctgtc tcaggactct gacactgt                                          28
```

```
<210> SEQ ID NO 6
<211> LENGTH: 23
<212> TYPE: DNA
<213> ORGANISM: Artificial Sequence
<220> FEATURE:
<223> OTHER INFORMATION: probe 6ROX labeled at 5'- and 3'- terminal
      amines

<400> SEQUENCE: 6
cagcacaact acgcagcgcc tcc                                               23
```

```
<210> SEQ ID NO 7
<211> LENGTH: 23
<212> TYPE: DNA
<213> ORGANISM: Artificial Sequence
<220> FEATURE:
<223> OTHER INFORMATION: probe 6CR110 labeled at 5'- and 3'- terminal
      amine

<400> SEQUENCE: 7
cagcacaact acgcagcgcc tcc                                               23
```

```
<210> SEQ ID NO 8
<211> LENGTH: 19
<212> TYPE: DNA
<213> ORGANISM: Artificial Sequence
<220> FEATURE:
<223> OTHER INFORMATION: probe JOE labeled at 5'- terminal amine and
      TAMRA at at 3'- terminal amine

<400> SEQUENCE: 8
caagcttccc gttctcagc                                                    19
```

```
<210> SEQ ID NO 9
<211> LENGTH: 19
<212> TYPE: DNA
<213> ORGANISM: Artificial Sequence
<220> FEATURE:
<223> OTHER INFORMATION: probe 5R6G labeled at 5'- and 3'- terminal
      amine

<400> SEQUENCE: 9
caagcttccc gttctcagc                                                    19
```

<210> SEQ ID NO 10
<211> LENGTH: 19
<212> TYPE: DNA
<213> ORGANISM: Artificial Sequence
<220> FEATURE:
<223> OTHER INFORMATION: probe 5CR110 labeled at 5'- terminal amines

<400> SEQUENCE: 10
caagcttccc gttctcagc                                            19

<210> SEQ ID NO 11
<211> LENGTH: 19
<212> TYPE: DNA
<213> ORGANISM: Artificial Sequence
<220> FEATURE:
<223> OTHER INFORMATION: probe 5CR110 labeled at 3'- terminal amines

<400> SEQUENCE: 11
caagcttccc gttctcagc                                            19

<210> SEQ ID NO 12
<211> LENGTH: 32
<212> TYPE: DNA
<213> ORGANISM: Artificial sequence
<220> FEATURE:
<223> OTHER INFORMATION: probe 6CR110 labeled at 5'- and 3'- terminal
      amines

<400> SEQUENCE: 12
ccaagcggct gagaacggga agcttggctt gg                             32

<210> SEQ ID NO 13
<211> LENGTH: 32
<212> TYPE: DNA
<213> ORGANISM: Artificial sequence
<220> FEATURE:
<223> OTHER INFORMATION: probe 6TAMRA labeled at 5'- and 3'- terminal
      amines

<400> SEQUENCE: 13
ccaagcggct gagaacggga agcttggctt gg                             32

<210> SEQ ID NO 14
<211> LENGTH: 32
<212> TYPE: DNA
<213> ORGANISM: Artificial Sequence
<220> FEATURE:
<223> OTHER INFORMATION: probe 6ROX labeled at 5'- and 3'- terminal
      amines

<400> SEQUENCE: 14
ccaagcggct gagaacggga agcttggctt gg                             32

<210> SEQ ID NO 15
<211> LENGTH: 19
<212> TYPE: DNA
<213> ORGANISM: Artificial Sequence
<220> FEATURE:
<223> OTHER INFORMATION: primer 5CR110 Labeled at 5'-end amine and  #18
      dT

<400> SEQUENCE: 15
gaaggtgaag gtcggagtc                                            19

<210> SEQ ID NO 16
<211> LENGTH: 18
<212> TYPE: DNA

```
<213> ORGANISM: Artificial Sequence
<220> FEATURE:
<223> OTHER INFORMATION: primer 5CR110 Labeled at 5'- terminal amine and
      #17 base of dT

<400> SEQUENCE: 16
aaggtgaagg tcggagtc                                                      18

<210> SEQ ID NO 17
<211> LENGTH: 20
<212> TYPE: DNA
<213> ORGANISM: Artificial Sequence
<220> FEATURE:
<223> OTHER INFORMATION: primer 5CR110 labeled at 5'- terminal amine and
      #17 base of dT

<400> SEQUENCE: 17
gaagatggtg atgggatttc                                                    20

<210> SEQ ID NO 18
<211> LENGTH: 19
<212> TYPE: DNA
<213> ORGANISM: Artificial Sequence
<220> FEATURE:
<223> OTHER INFORMATION: primer 5CR110 labeled at 5'- terminal amine

<400> SEQUENCE: 18
gaaggtgaag gtcggagtc                                                     19

<210> SEQ ID NO 19
<211> LENGTH: 18
<212> TYPE: DNA
<213> ORGANISM: Artificial Sequence
<220> FEATURE:
<223> OTHER INFORMATION: primer 5CR110 labeled at #17 dT

<400> SEQUENCE: 19
aaggtgaagg tcggagtc                                                      18

<210> SEQ ID NO 20
<211> LENGTH: 19
<212> TYPE: DNA
<213> ORGANISM: Artificial Sequence
<220> FEATURE:
<223> OTHER INFORMATION: primer 5CR110 Labeled at #18 dT

<400> SEQUENCE: 20
gaaggtgaag gtcggagtc                                                     19

<210> SEQ ID NO 21
<211> LENGTH: 19
<212> TYPE: DNA
<213> ORGANISM: Artificial Sequence
<220> FEATURE:
<223> OTHER INFORMATION: probe 6CR110 labeled at 5'- and 3'- terminal
      amines

<400> SEQUENCE: 21
caagcttccc gttctcagc                                                     19

<210> SEQ ID NO 22
<211> LENGTH: 19
<212> TYPE: DNA
<213> ORGANISM: Artificial Sequence
<220> FEATURE:
<223> OTHER INFORMATION: probe 6TAMRA labeled at 5'- and 3'- terminal
      amines
```

```
<400> SEQUENCE: 22
caagcttccc gttctcagc                                              19

<210> SEQ ID NO 23
<211> LENGTH: 19
<212> TYPE: DNA
<213> ORGANISM: Artificial Sequence
<220> FEATURE:
<223> OTHER INFORMATION: probe 6ROX labeled at 5'- and 3'- terminal
      amines

<400> SEQUENCE: 23
caagcttccc gttctcagc                                              19

<210> SEQ ID NO 24
<211> LENGTH: 226
<212> TYPE: DNA
<213> ORGANISM: Homo sapiens

<400> SEQUENCE: 24
gaaggtgaag gtcggagtca acggatttgg tcgtattggg cgcctggtca ccagggctgc   60
ttttaactct ggtaaagtgg atattgttgc catcaatgac cccttcattg acctcaacta  120
catggtttac atgttccaat atgattccac ccatggcaaa ttccatggca ccgtcaaggc  180
tgagaacggg aagcttgtca tcaatggaaa tcccatcacc atcttc                 226

<210> SEQ ID NO 25
<211> LENGTH: 121
<212> TYPE: DNA
<213> ORGANISM: Homo sapiens

<400> SEQUENCE: 25
tcaagaggtg ccacgtctcc acacatcagc acaactacgc agcgcctccc tccactcgga   60
aggactatcc tgctgccaag agggtcaagt tggacagtgt cagagtcctg agacagatca  120
g                                                                  121

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
ccacggacca tgaccatga                                               19

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
tcttgagctg cggacggt                                                18

<210> SEQ ID NO 28
<211> LENGTH: 20
<212> TYPE: DNA
<213> ORGANISM: Artificial Sequence
<220> FEATURE:
<223> OTHER INFORMATION: probe 6CR110 labeled at 5'- and 3'- terminal
```

```
                              amines

<400> SEQUENCE: 28
ccaaagcatc cgggatggcc                                                    20

<210> SEQ ID NO 29
<211> LENGTH: 20
<212> TYPE: DNA
<213> ORGANISM: Artificial Sequence
<220> FEATURE:
<223> OTHER INFORMATION: probe 5-R6G labeled at 5'- and 3'- terminal
      amines

<400> SEQUENCE: 29
ccaaagcatc tgggatggcc                                                    20

<210> SEQ ID NO 30
<211> LENGTH: 106
<212> TYPE: DNA
<213> ORGANISM: Homo sapiens

<400> SEQUENCE: 30
ccacggacca tgaccatgac cctccacacc aaagcatccg ggatggccct actgcatcag        60
atccaaggga acgagctgga gcccctgaac cgtccgcagc tcaaga                      106

<210> SEQ ID NO 31
<211> LENGTH: 106
<212> TYPE: DNA
<213> ORGANISM: Homo sapiens

<400> SEQUENCE: 31
ccacggacca tgaccatgac cctccacacc aaagcatctg ggatggccct actgcatcag        60
atccaaggga acgagctgga gcccctgaac cgtccgcagc tcaaga                      106

<210> SEQ ID NO 32
<211> LENGTH: 109
<212> TYPE: DNA
<213> ORGANISM: Hepatitus C virus

<400> SEQUENCE: 32
gcacgaatcc taaacctcaa agaaaaacca aacgtaacac caaccgccgc ccacaggacg        60
tcaagttccc gggcggtggt cagatcgttg gtggagttta cctgttgcc                   109

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
gcacgaatcc taaacctcaa aa                                                 22

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
ggcaacaagt aaactccacc aa                                                 22
```

<210> SEQ ID NO 35
<211> LENGTH: 21
<212> TYPE: DNA
<213> ORGANISM: Artificial Sequence
<220> FEATURE:
<223> OTHER INFORMATION: probe 6ROX labeled at 5'- and 3'- terminal
      amines

<400> SEQUENCE: 35
atctgaccac cgcccgggaa c                                          21

<210> SEQ ID NO 36
<211> LENGTH: 23
<212> TYPE: DNA
<213> ORGANISM: Artificial Sequence
<220> FEATURE:
<223> OTHER INFORMATION: probe non-sulfonated Cy-5 labeled at 5'- and
      3'- terminal amines

<400> SEQUENCE: 36
cagcacaact acgcagcgcc tcc                                        23

US 7,667,024 B2

OLIGONUCLEOTIDES LABELED WITH A PLURALITY OF FLUOROPHORES

PRIORITY CLAIM

This application claims the benefit of U.S. Provisional Patent Application Ser. No. 60/523,263 filed on Nov. 19, 2003, which is incorporated herein in its entirety.

BACKGROUND

The present invention relates in general to oligonucleotides labeled with a plurality of spectrally identical or similar dyes and optionally one or more quencher dyes, as well as methods of creating labeled oligonucleotides and various uses of the labeled oligonucleotides as primers or probes for highly sensitive nucleic acid detection, including real-time polymerase chain reaction (PCR).

Nucleic acid polymers such as DNA and RNA are essential to the transmission of genetic information from one generation to the next and in the routine functioning of all living organisms. Accordingly these molecules are the object of intense study and a number of techniques have been developed to study of these molecules. These methods include but are not limited to methods for identifying the presence of a specific polynucleotide sequences in a given sample and methods designed to measure the number of specific nucleic acid molecules originally present in a given sample.

Practical uses for these techniques include identifying specific species and relationships between various species based upon similarities in oligonucleotide sequences. Other uses include diagnosing disease by identifying specific sequences in a given sample as indicative of a given pathology. Still other uses, too numerous to mention, include identifying individuals with a predisposition for developing a specific pathology as well as assessing the efficacy of proposed treatment regimes based on the presence of specific polynucleotides in a given patient's genome.

One of the most widely used and powerful techniques for the study and manipulation of oligonucleotides is the polymerase chain reaction (PCR). PCR is a primer extension reaction that provides a method for amplifying specific nucleic acids in vitro. This technique was first described in 1987. PCR can produce million fold copies of a DNA template in a single enzymatic reaction mixture within a matter of hours, enabling researchers to determine the size and sequence of target DNA. This DNA amplification technique has been widely used for cloning and other molecular biological manipulations. Further discussion of PCR is provided in Mullis et al., *Methods Enzymol.* (1987); and Saiki et al., *Science* (1985).

In PCR the particular stretch of DNA to be amplified is referred to as the 'target sequence'. The target sequence is replicated by first binding a complimentary 'primer' to a single stranded portion of the target polynucleotide. One PCR based technique that is particularly useful is Quantitative PCR (qPCR). Briefly, the mechanism of qPCR is based on the fact that PCR amplifies a target DNA in an exponential manner. By running a PCR reaction and measuring the total number of DNA copies at given points during the course of the amplification reaction, one can retroactively calculate the amount of starting DNA material.

Various methods have been developed for determining the amount of PCR product made without having to stop the PCR run or even to sample the reaction during a given PCR run. One such method follows the course of the PCR run in real time by measuring the amount of product at each cycle of DNA synthesis. This process is referred to as real time PCR (RT-PCR). Because of its great sensitivity and because measurements can be made with the sample still in the PCR thermocylcer, various fluorescence-based assays that monitor the formation of PCR products have been developed. A number of instruments and methods have been developed for real-time PCR (RT-PCR). A real-time PCR instrument is typically a fluorometer built upon a thermocycler. Commercially available real-time PCR instruments include Prism7700 by ABI, LightCycler by Roche, Opticon by MJ Research, iCycler IQ by BioRad, and MX4000 by Stratagene.

An oligonucleotide used to identify a given sequence of nucleic acid by hybridizing to it, but that does not serve to amplify the sequence may be referred to as a 'probe'. Probes also find utility in PCR reactions where they are used to signal polynucleotide amplification.

Given the importance of oligonucleotide and the myriad of ways in which these molecules can impact human, animal and plant life there is a need for ever more efficient methods for the study and manipulation of oligonucleotide. Including new techniques for efficiently producing labeled oligonucleotide. One object of the present invention is to provide labeled oligonucleotide and efficient methods for making and using the same.

SUMMARY

The present invention provides a methods for labeling oligonucleotides that find utility in assays such as those designed to identify the presence of a given polynucleotide in a sample or to amplify the amount of a given oligonucleotide or polynucleotide in a given sample. It provides methods for using these types of labeled oligonucleotides.

One embodiment includes oligonucleotides labeled with at least two photometric molecules that have excitation wavelengths that are within 15 nm of one another. In some embodiments the labeled oligonucleotides produce relatively little spectral signal until at least two of the photometric molecules are permanently separated from each other as a result of oligonucleotide cleavage.

One embodiment is an oligonucleotide labeled with two spectrally similar or identical photometric molecules that are fluorescent. The detectable emission from the fluorescent molecules increases when at least two of the molecules are permanently separated from one another as a result of -oligonucleotide cleavage. In another embodiment the florescence signal produced by the at least two fluorescent molecules attached to the oligonucleotide increases when the oligonucleotide hybridizes to a target oligonucleotide sequence.

One embodiment is an oligonucleotide labeled with at least two photometric molecules in which the oligonucleotide sequence is substantially devoid of secondary structure, such as hairpin loops and stem-loop structures.

One embodiment includes an oligonucleotide labeled with photometric molecules that have identical or similar spectral properties and are attached at the 5' and 3' ends, respectively of the oligonucleotide. In one variation of this embodiment one dye is attached at the 5' terminal backbone phosphate and the other dye attached at the 3' terminal backbone phosphate.

In one embodiment the oligonucleotide is suitable for use as primer comprising at least two spectrally identical or similar fluorescent dyes and optionally one or more fluorescence quencher dyes. In one embodiment the oligonucleotide is suitable for use as a labeled primer. In another embodiment the fluorescent molecules may be attached to the bases of nucleosides, or to a combination of the 5' terminal backbone phosphate and the bases.

In one embodiment an oligonucleotide is labeled with at least two spectrally identical or similar fluorescent dyes. The oligonucleotide may be a primer for use in nucleic acid amplification reactions including, for example, spectrally similar or identical fluorescent dyes attached to the 5' terminal phosphate backbone and the base of a nucleoside, for example, a thymidine nucleotide.

One embodiment includes methods for producing oligonucleotides that are labeled with at least two photometric molecules in which the photometric molecules are spectrally similar or identical. Labeled oligonucleotides produced using some of these methods produce more detectable signal when at least two of the at least two photometric molecules are permanently separated from one another.

Yet another embodiment includes methods for utilizing oligonucleotides labeled with at least two photometric molecules that have excitation wavelengths that are within 15 nm or one another's.

Still other embodiments includes uses for oligonucleotides labeled according to embodiments of the invention. These uses include, but are not limited to, assays to analyze biological samples comprising nucleic acid sequence in a variety of contexts. One exemplary application includes, fluorescence in situ hybridization (FISH), wherein oligonucleotide labeled in accordance with the invention can be used for localizing and determining the relative abundance of a target nucleic acid sequences with biological importance in, for examples, live cells, fixed tissue or a chromosome sample.

Other embodiments include using oligonucleotides labeled with a plurality of dyes in solution-based or chip-based array detection systems and quantification of differential expression of genes linked with disease in basic research and the diagnosis of disease.

Still other embodiments includes methods and kits suitable for making oligonucleotides labeled according to embodiments of the invention. These kits may be used in the detection of amplified oligonucleotide sequences, which includes iso-thermo amplifications, ligase chain reactions and the like.

Various embodiments are suitable for use with PCR to detect biomolecules other than nucleic acids by using an oligonucleotide-antibody conjugate wherein the antibody is specific for the biomolecules to be detected.

Further forms, embodiments, objects, functions and aspects from the present invention shall become apparent from the description contained herein.

BRIEF DESCRIPTION OF THE FIGURES AND TABLES

Figure 3A:
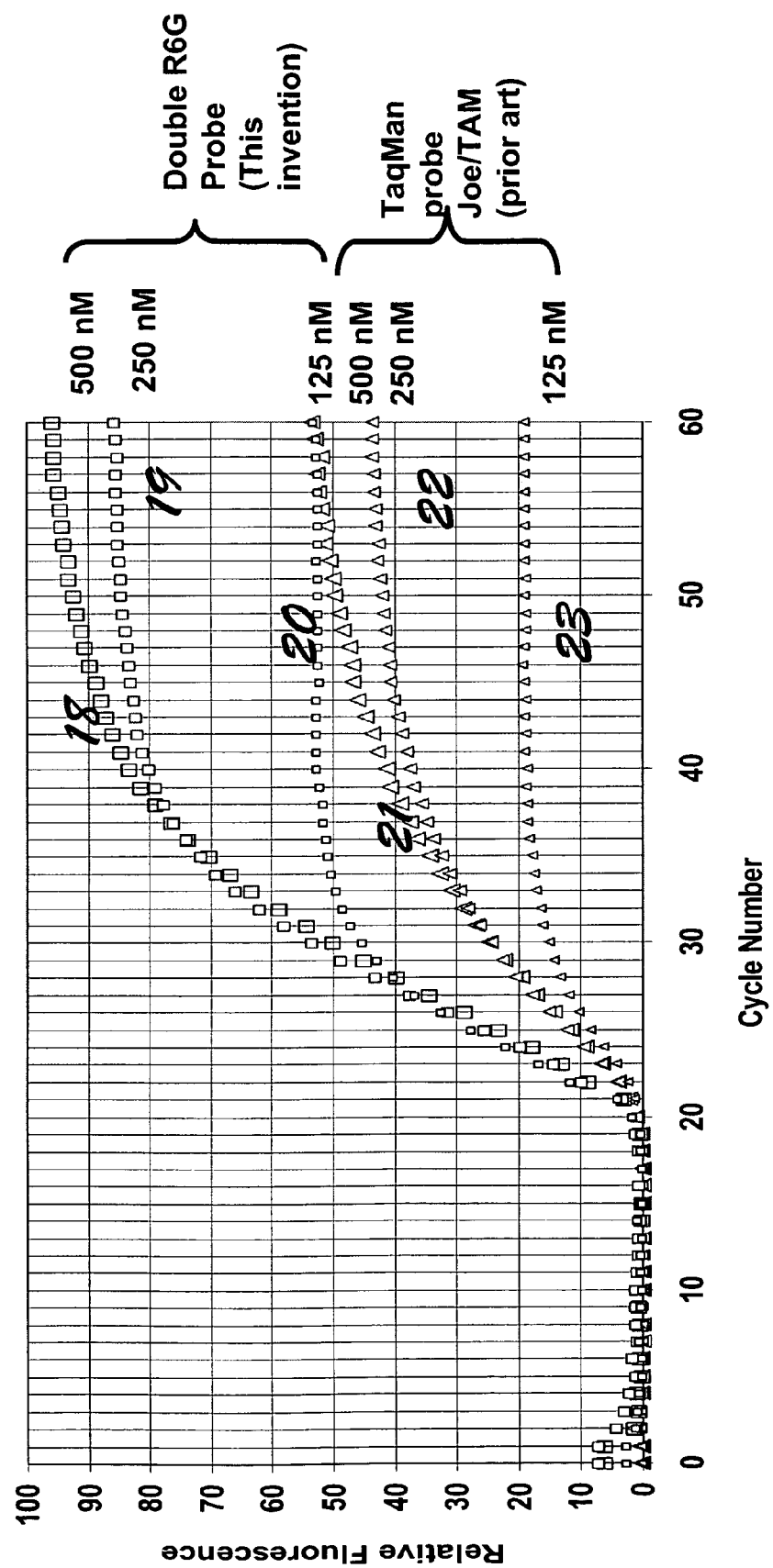
FIG. 3A illustrates data collected by comparing a TaqMan probe with a probe made in conformity with one embodiment of the invention. The TaqMan probe was labeled with JOE at 5' terminus and TAMRA at 3' terminus; the probe of the present invention has the same oligonucleotide sequences as the TaqMan probe but it was labeled with R6G at both 5' and 3' termini. (Example 4)
Figure 3B:
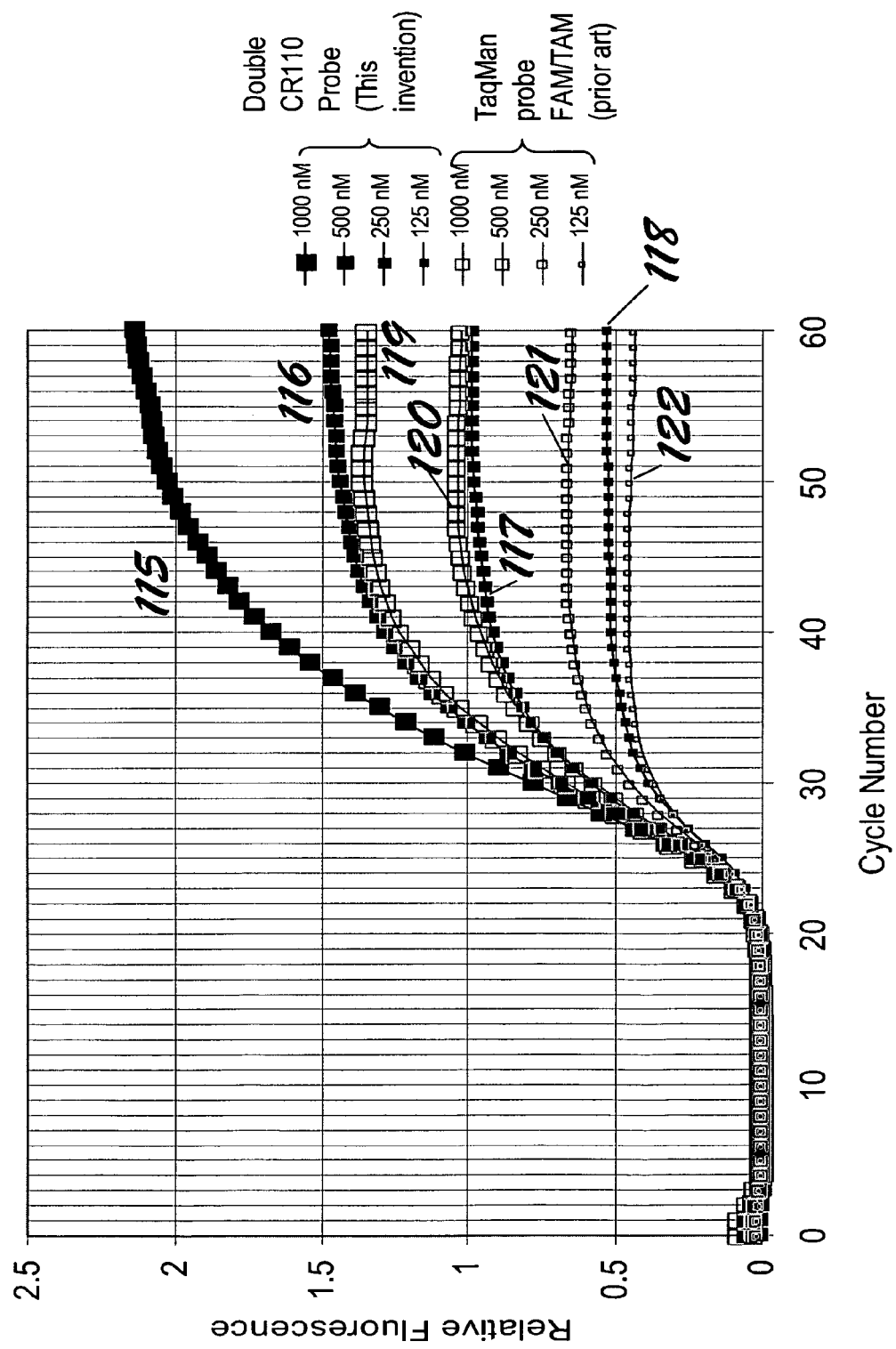

FIG. 3B shows the result of a comparison of a TaqMan probe with a probe made in conformity with one embodiment of the present invention. The TaqMan probe was labeled with FAM at 5' terminus and TAMRA at 3' terminus; the probe of the present invention has the same oligonucleotide sequences as the TaqMan probe but it was labeled with 6-CR110 at both the 5' and 3' termini. (Example 4)

Figure 3C:
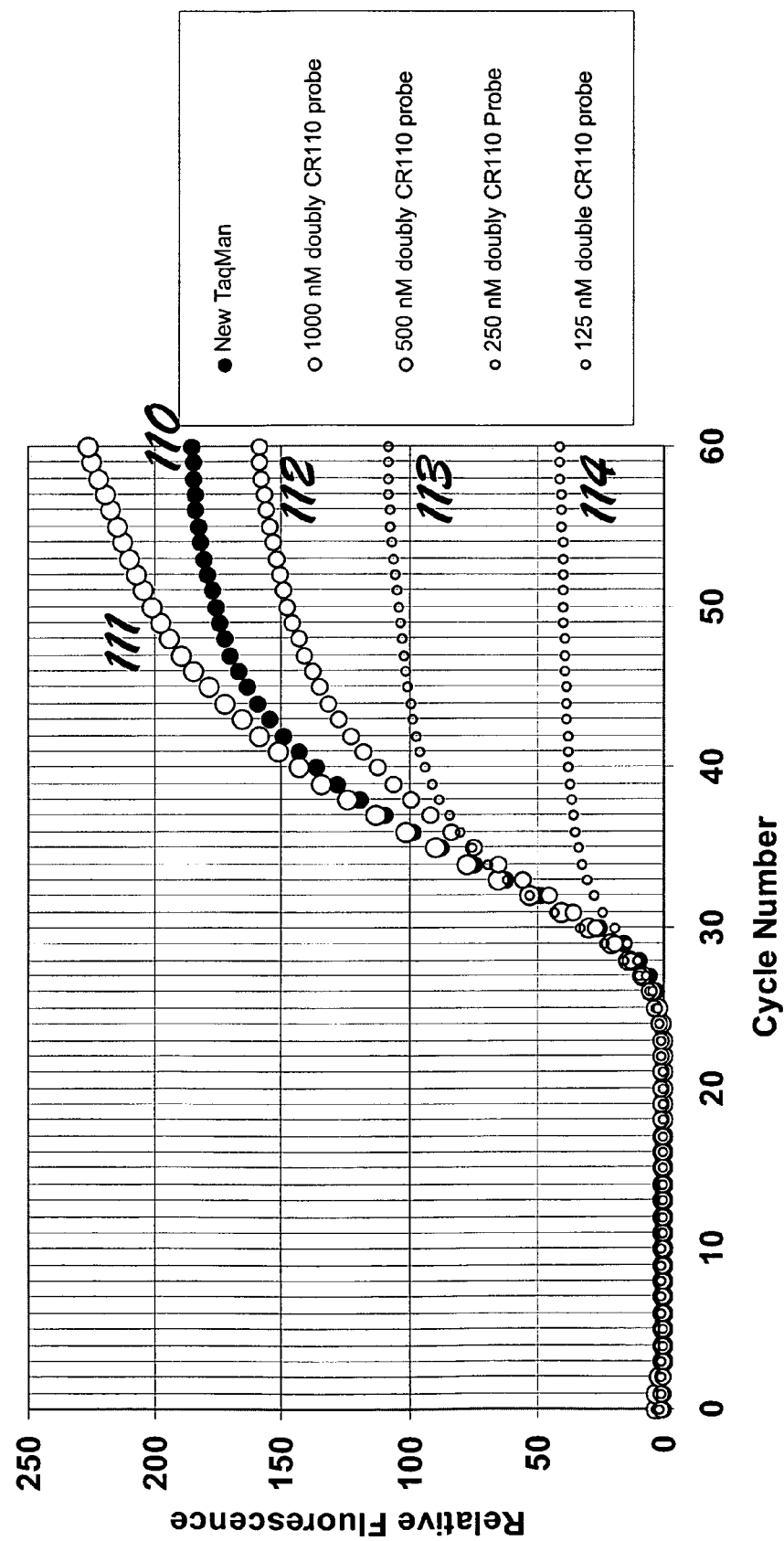

FIG. 3C shows the result of a comparison of a TaqMan probe with a probe made in conformity with one embodiment of the present invention. The TaqMan probe from ABI with an undisclosed sequence had a FAM at 5' end, a MGB and a quencher at the 3' end; the probe of the present invention was labeled with 6CR110 at both the 5' and 3' termini. (Example 4)

Figure 4A:
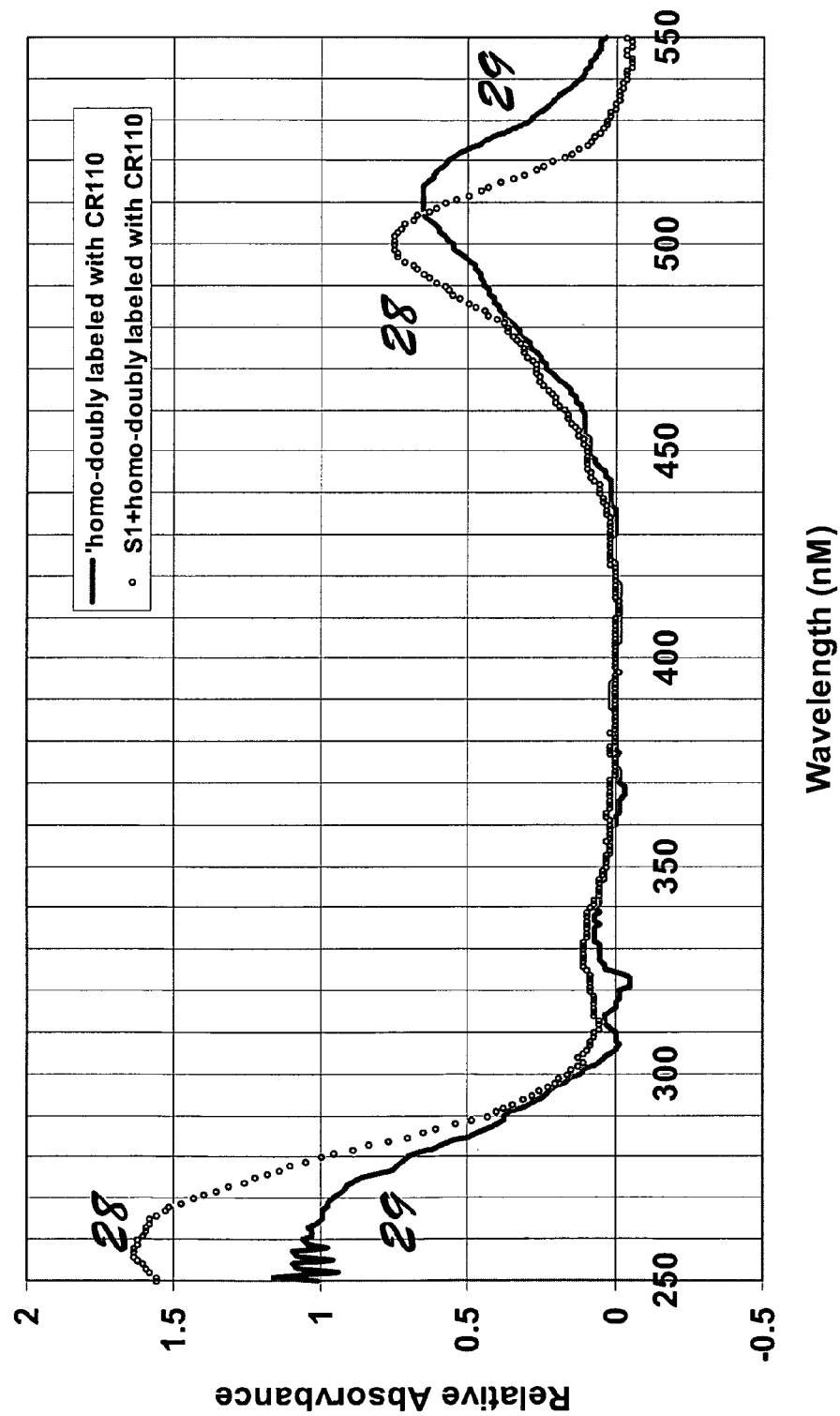

FIG. 4A shows the absorption spectra of a GAPDH probe labeled with two molecules of 5-CR110 at the termini both before and after S1 digestion (SEQ ID No. 3, Example 5).

Figure 4B:
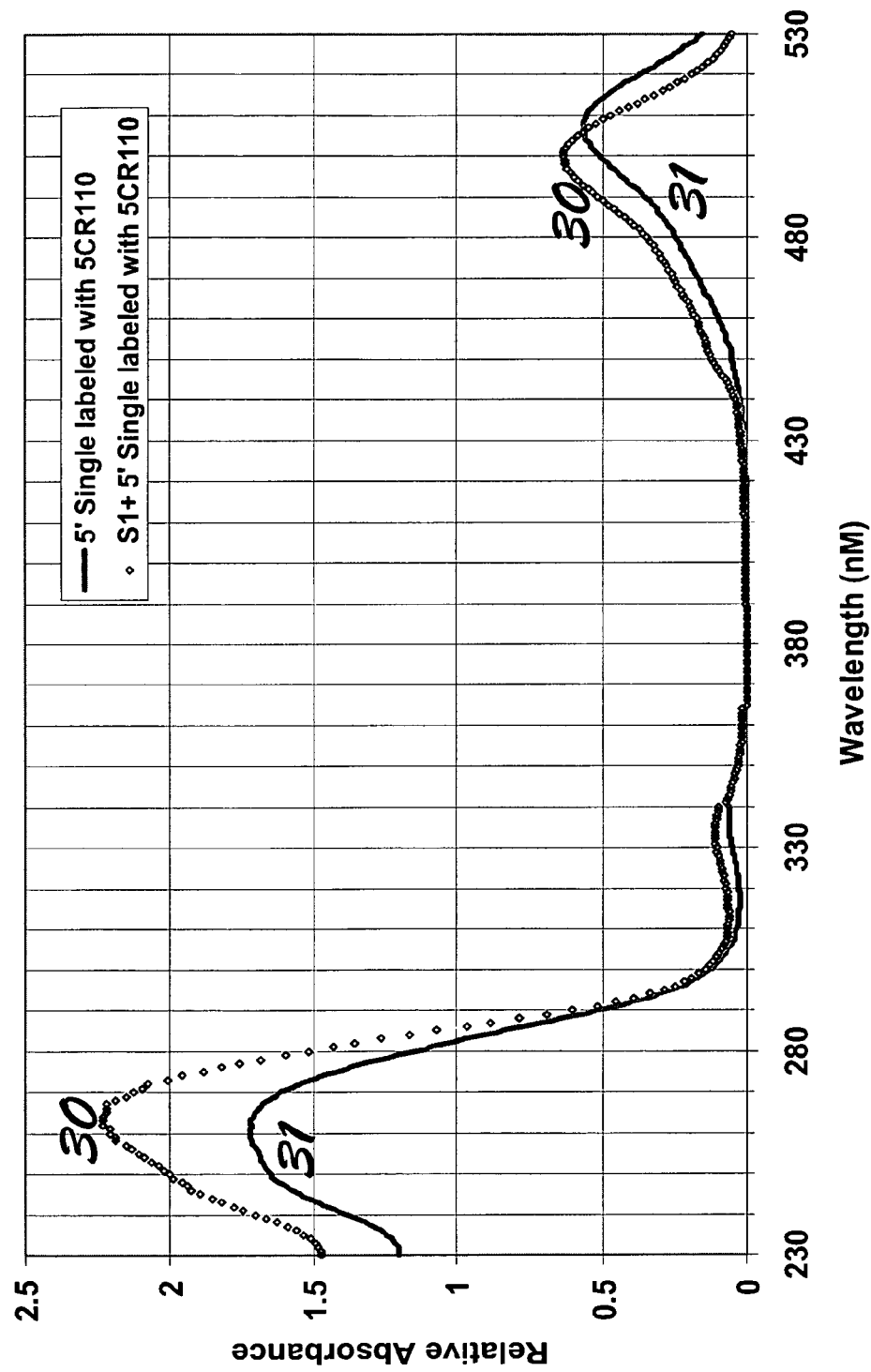

FIG. 4B shows the absorption spectra of a GAPDH probe labeled with one 5-CR110 at the 5' terminus (SEQ ID No. 10) both before and after S1 digestion. (Example 5)

Figure 4C:
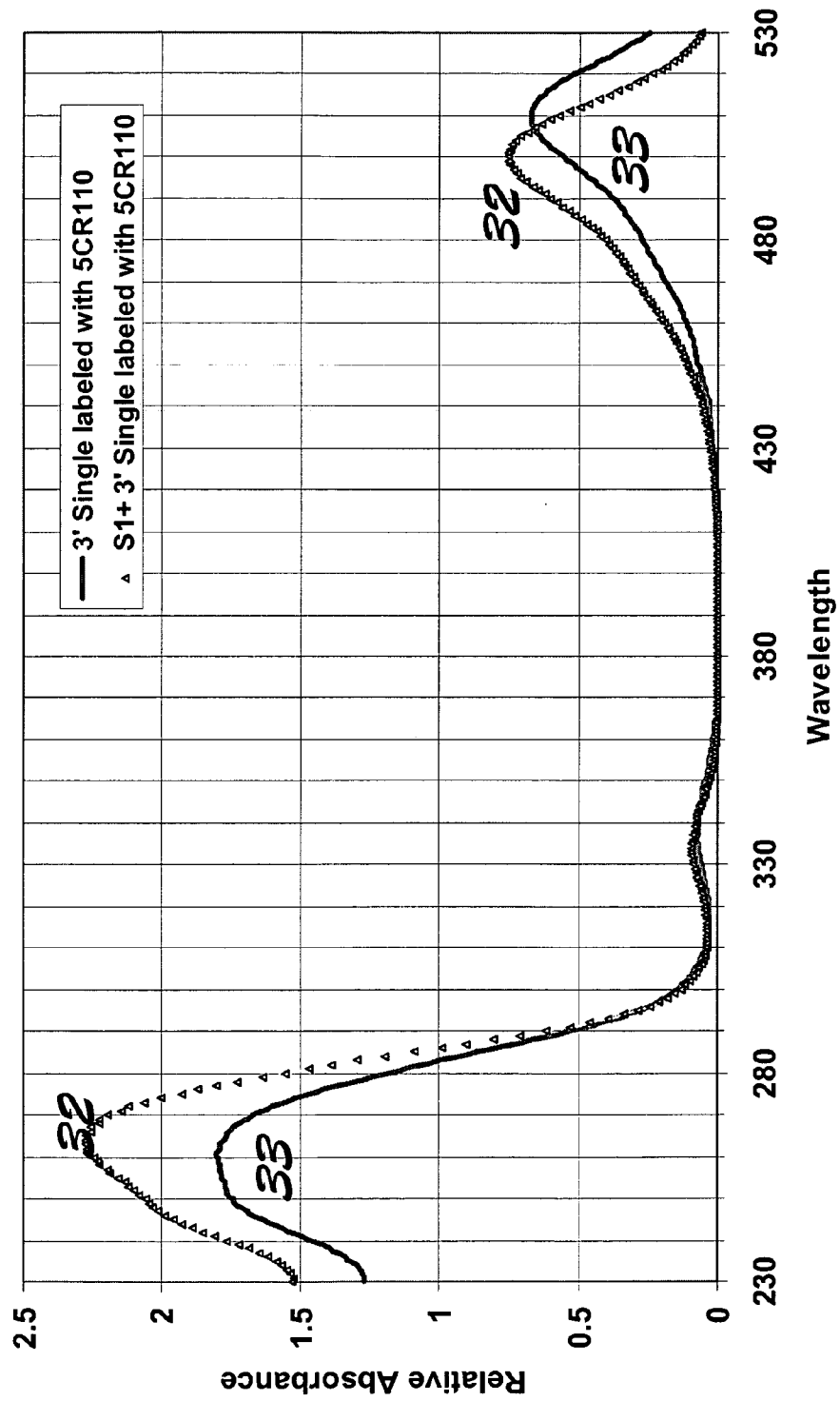

FIG. 4C shows the absorption spectra of a GAPDH probe labeled with one 5-CR110 at the 3' terminus (SEQ ID No. 11) both before and after S1 digestion. (Example 5)

Figure 4D:
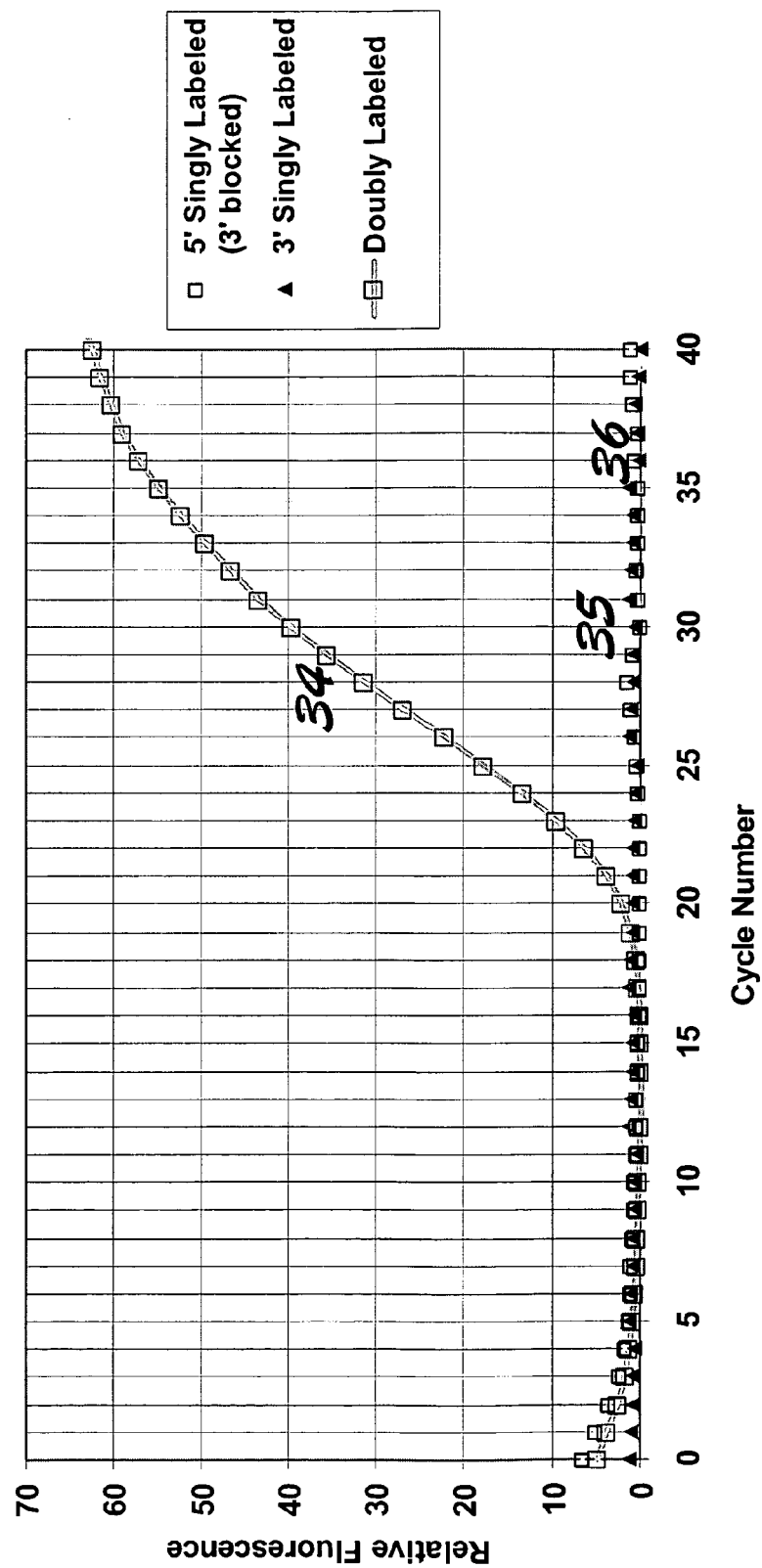

FIG. 4D shows the amplification plots collected using the three probes used in 4A, 4B and 4C. (Example 6)

Figure 5A:
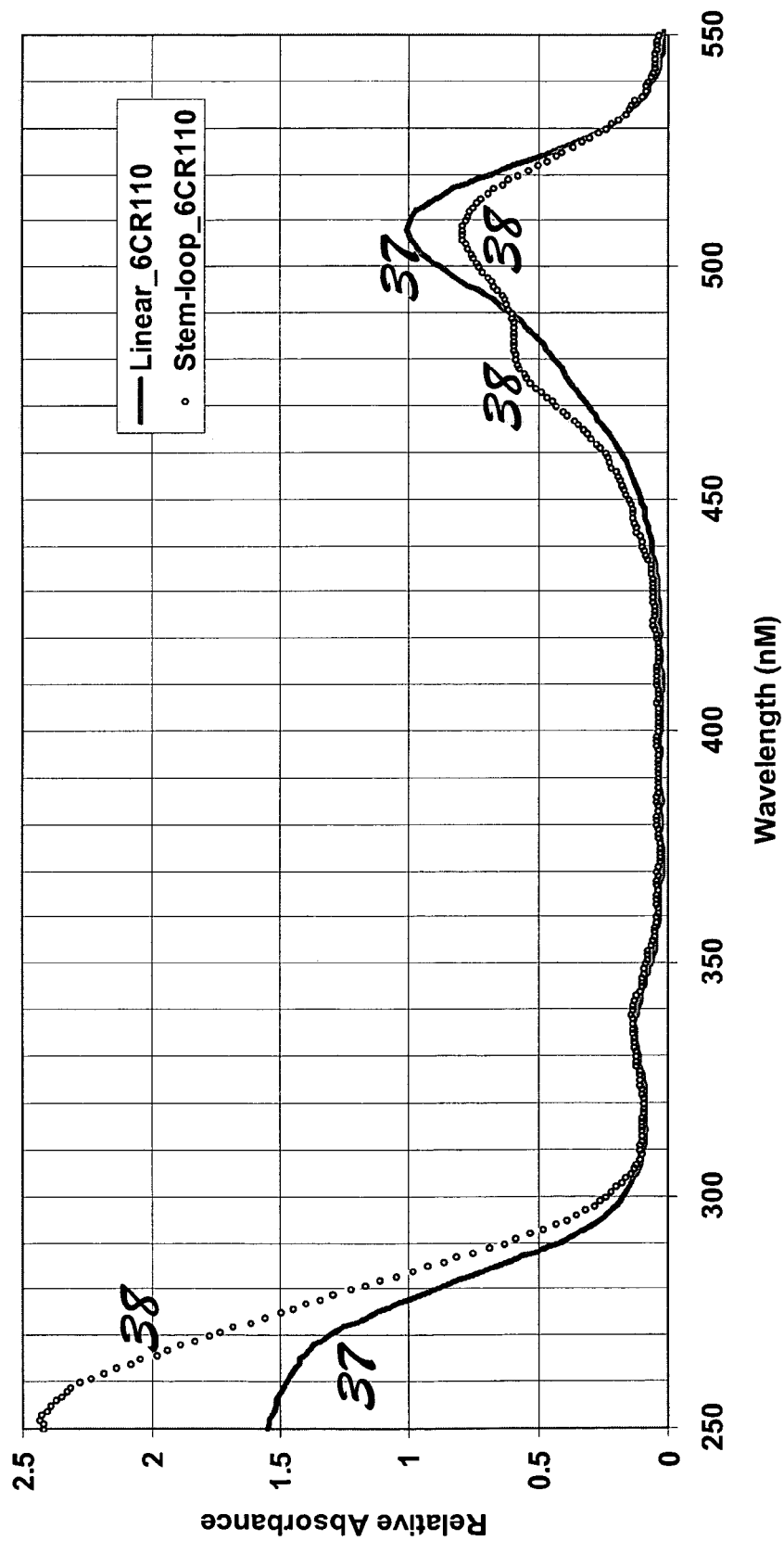

FIG. 5A shows the absorption spectra of linear and stem-looped GAPDH probes labeled with two 6-CR110. This figure illustrates that stem-loop structures facilitate 6-CR110-dimer formation. (Example 7)

Figure 5C:
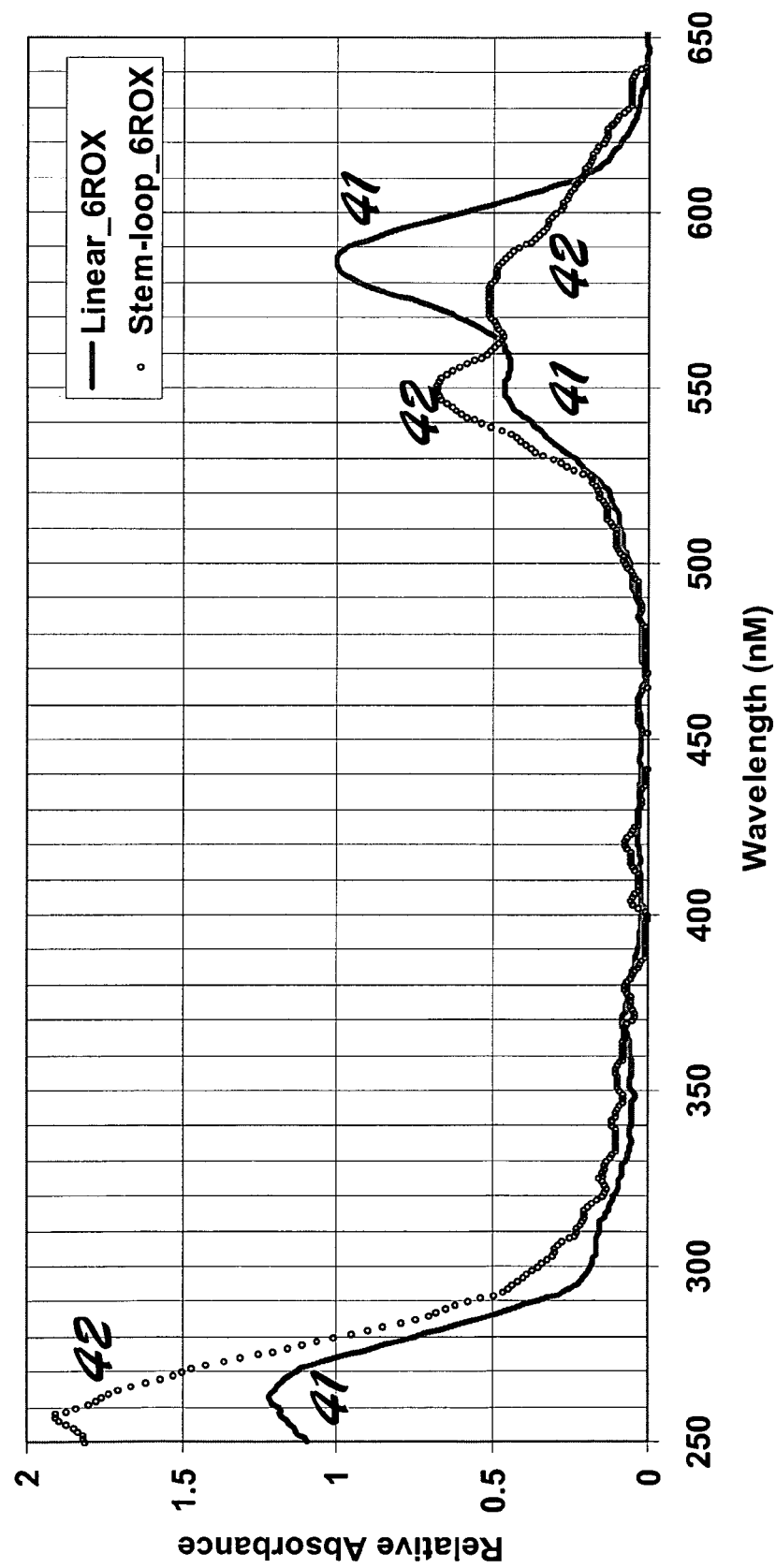
Figure 5B:
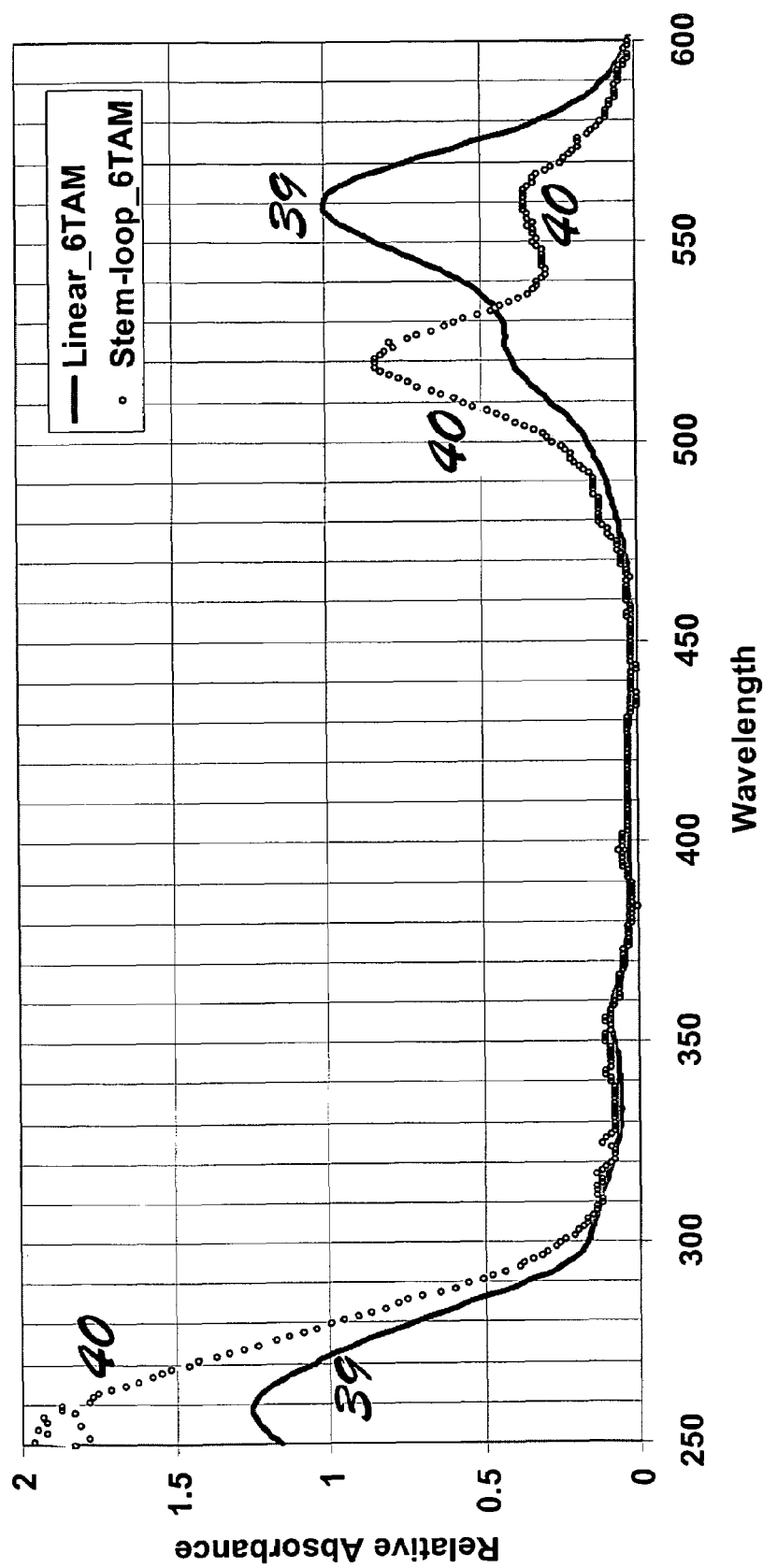

FIG. 5B shows the absorption spectra of linear and stem-looped GAPDH probes labeled with two molecules of 6-TAMRA. These data illustrate that a stem-loop structure strongly promotes 6-TAMRA-dimer formation. (Example 7)

FIG. 5C shows absorption spectra of a linear probe and stem-loop probe for GAPDH probes labeled with two molecules of 6-ROX. The data depicted in this figure illustrates that a stem-loop structure strongly promotes 6-ROX-dimer formation. (Example 7)

Figure 6A:
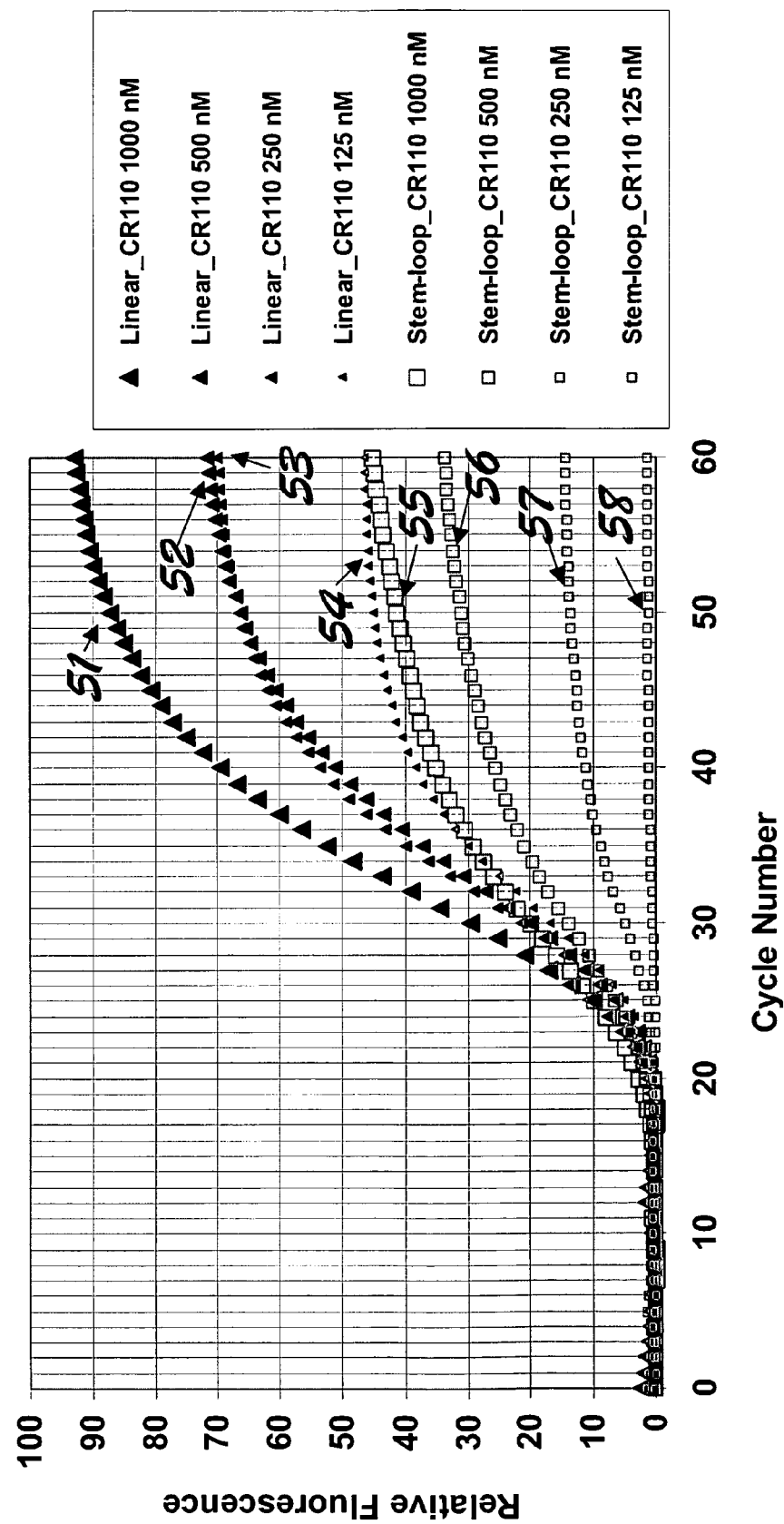

FIG. 6A depicts the result of comparing the performance of a doubly 6-CR110-labeled linear probe and a stem-loop probe in real time PCR at various probe concentrations. This figure illustrates that the linear probe generates a significantly stronger signal than the probe that forms a stem-loop structure. (Example 8)

Figure 6B:
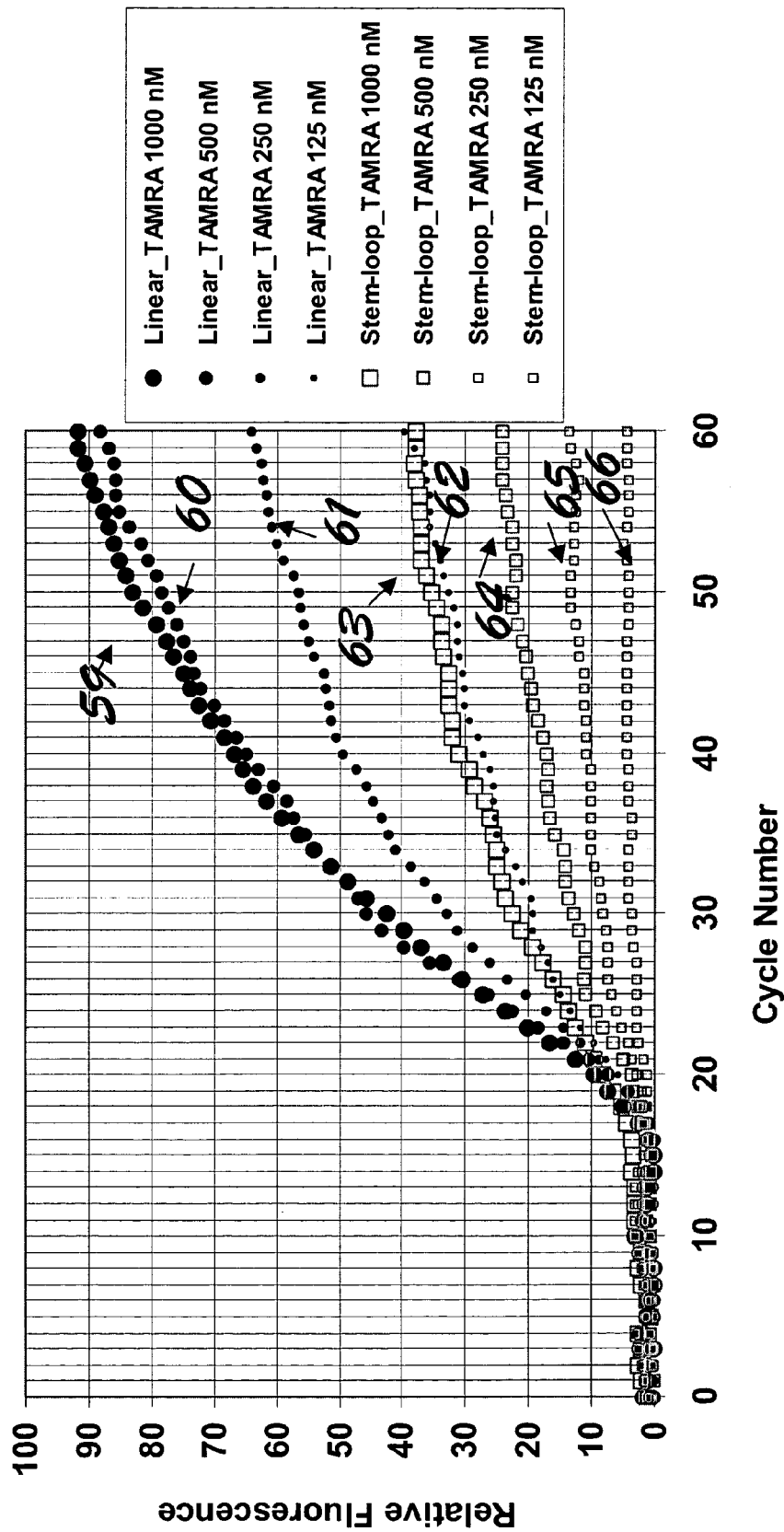

FIG. 6B illustrates a comparison of the performance of a doubly 6-TAMRA-labeled linear probe and a stem-loop probe in real time PCR measured at various probe concentrations. This figure illustrates that the linear probe generates a significantly stronger signal than the probe that forms a stem-loop structure. (Example 8)

Figure 6C:
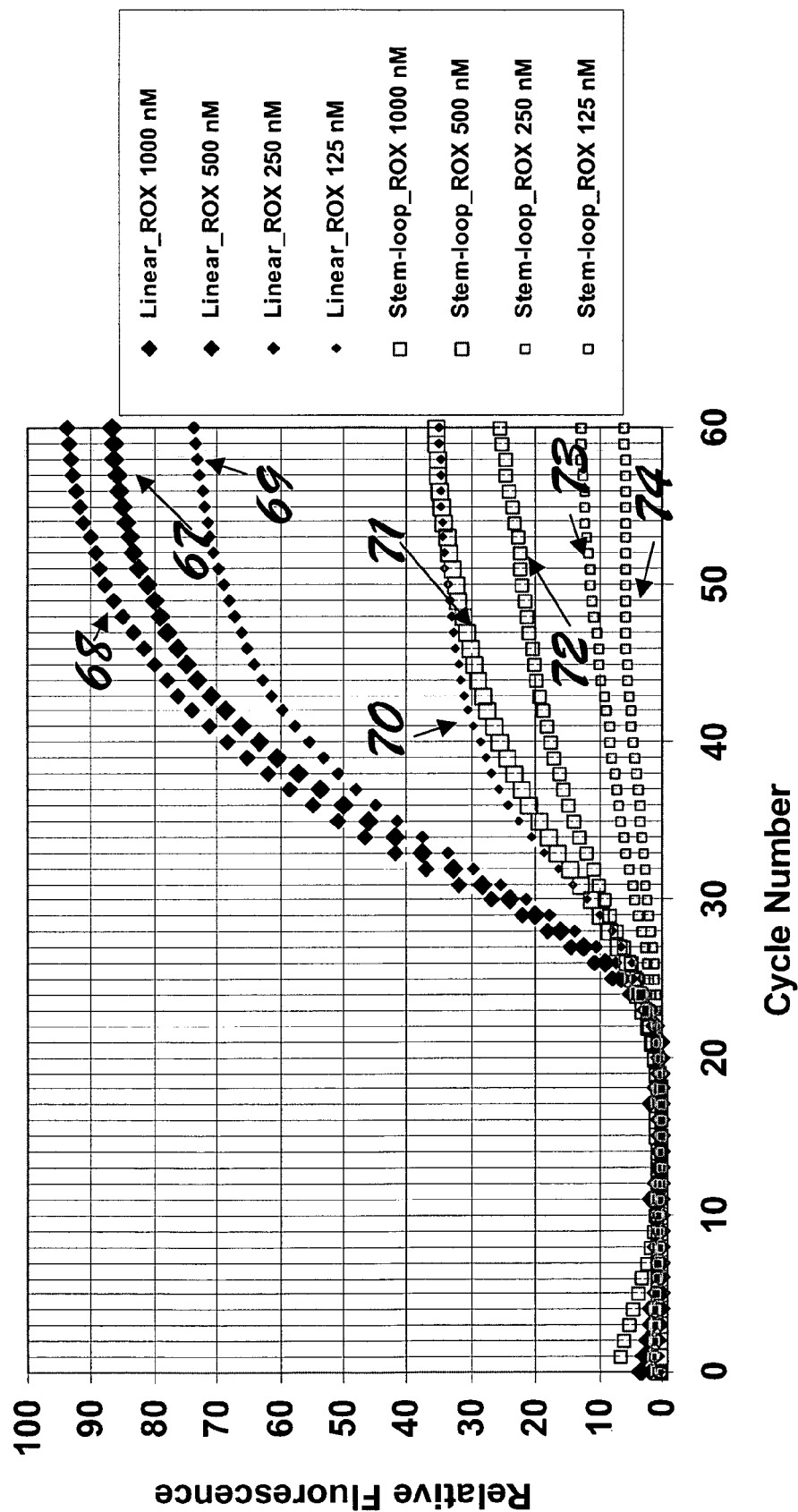

FIG. 6C depicts a comparison of the performance of doubly a 6-ROX-labeled linear and a stem-loop probe in real time PCR with various probe concentrations. This figure illustrates that the linear probe generates a significantly stronger signal than the probe that forms a stem-loop structure. (Example 8)

Figure 7:
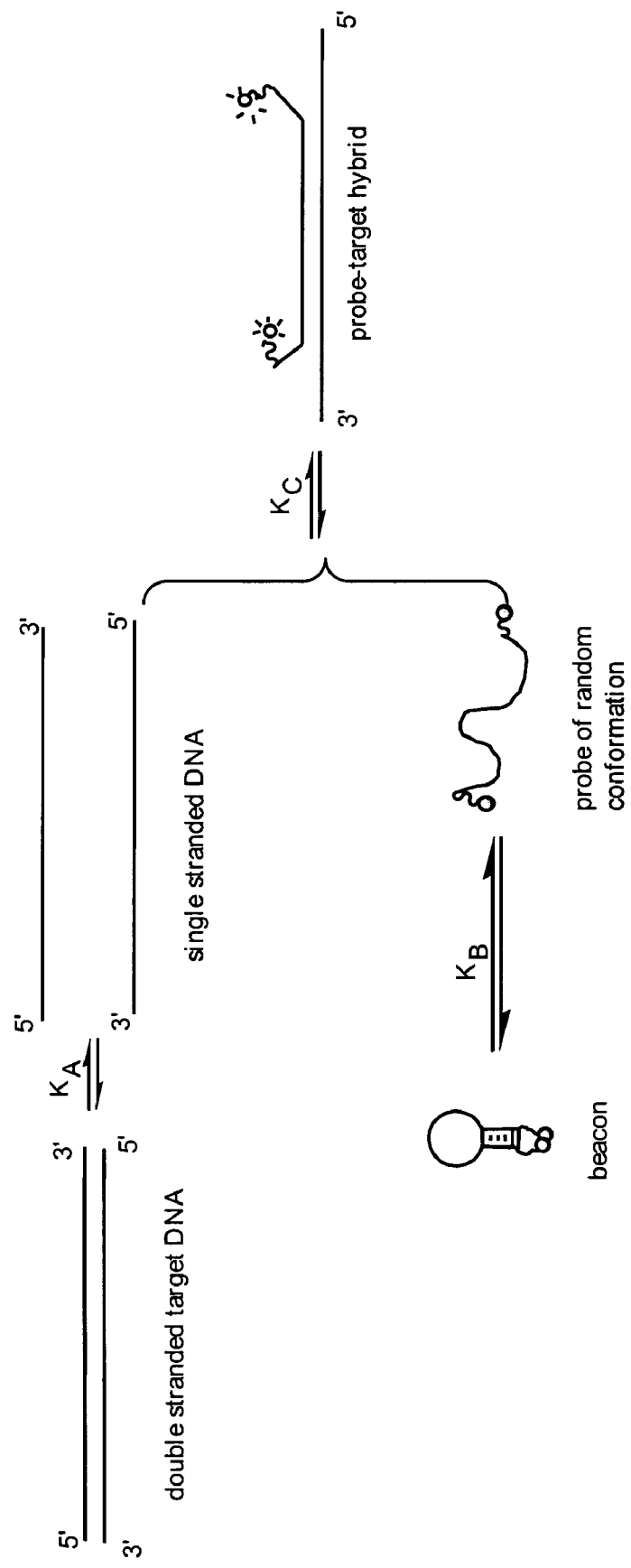

FIG. 7 illustrates the chemical equilibria involved in nucleic acid detection using a beacon probe. (Example 8)

Figure 8A:
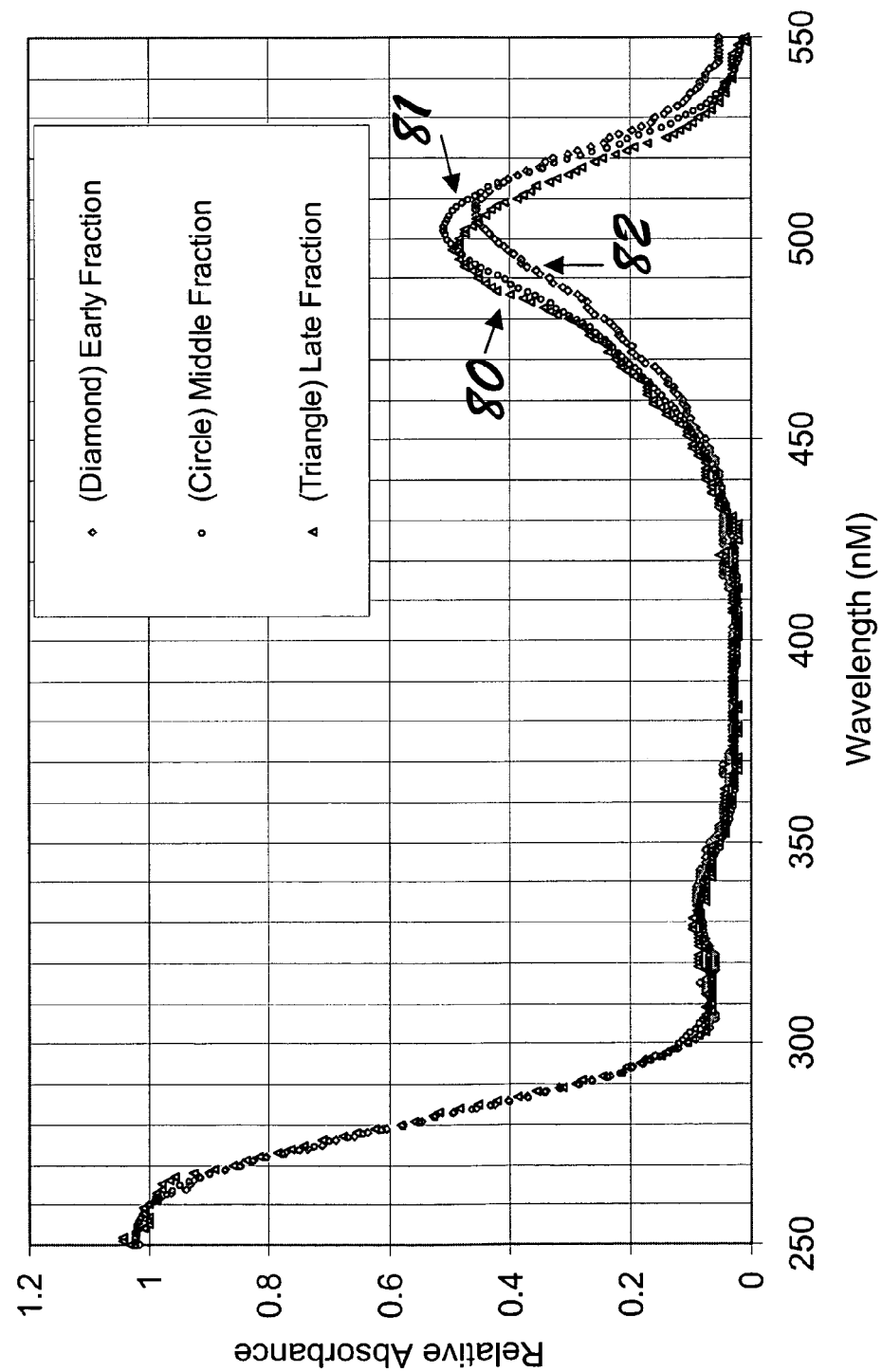

FIG. 8A depicts the spectra of three probes labeled with a combination of FAM/FAM, FAM/CR110 and CR110/CR110 dye pairs, respectively (Example 9).

Figure 8B:
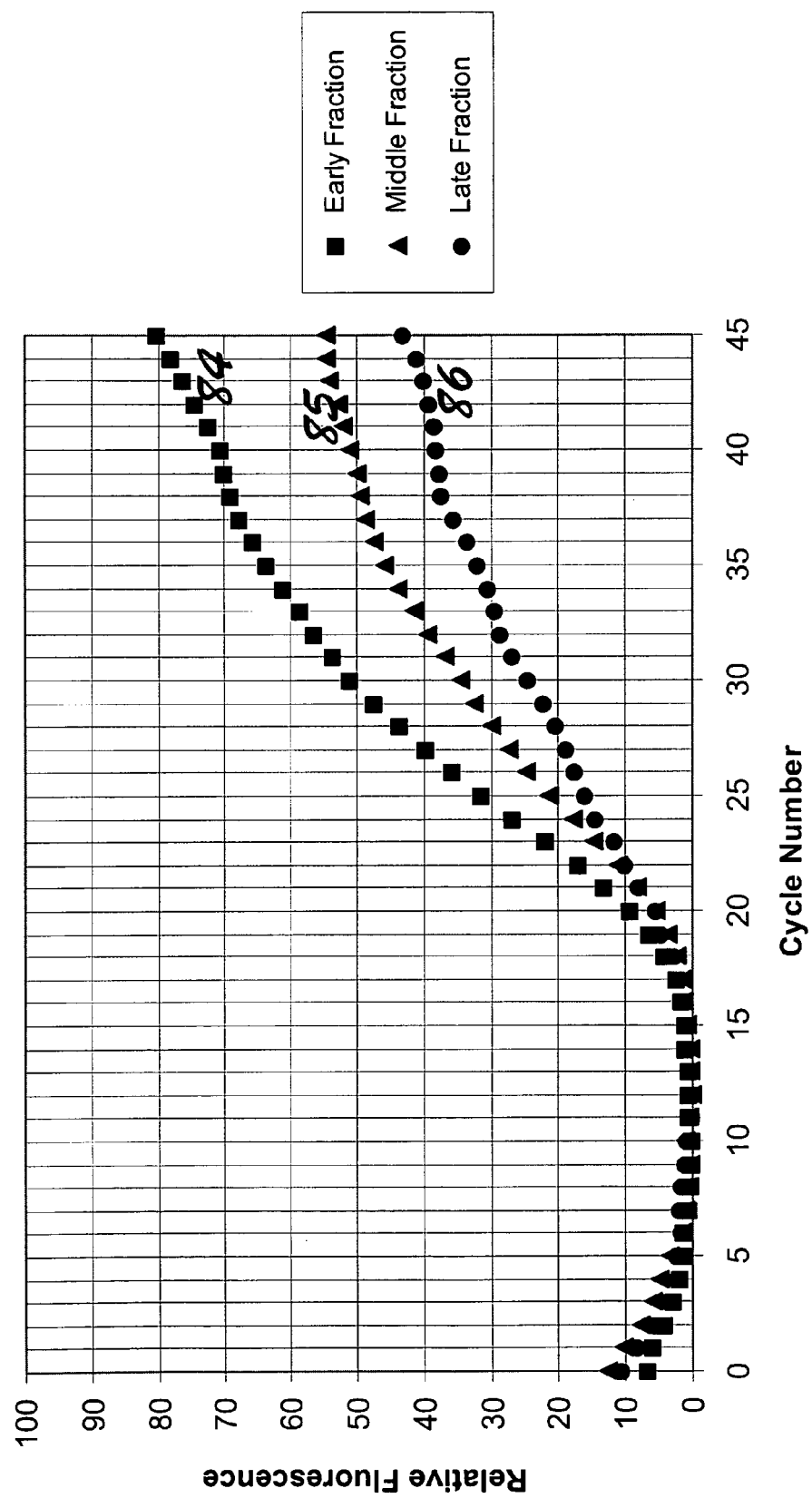

FIG. 8B illustrates amplification plots of the GAPDH gene detected with the probes depicted in FIG. 8A. (Example 9)

Figure 9A:
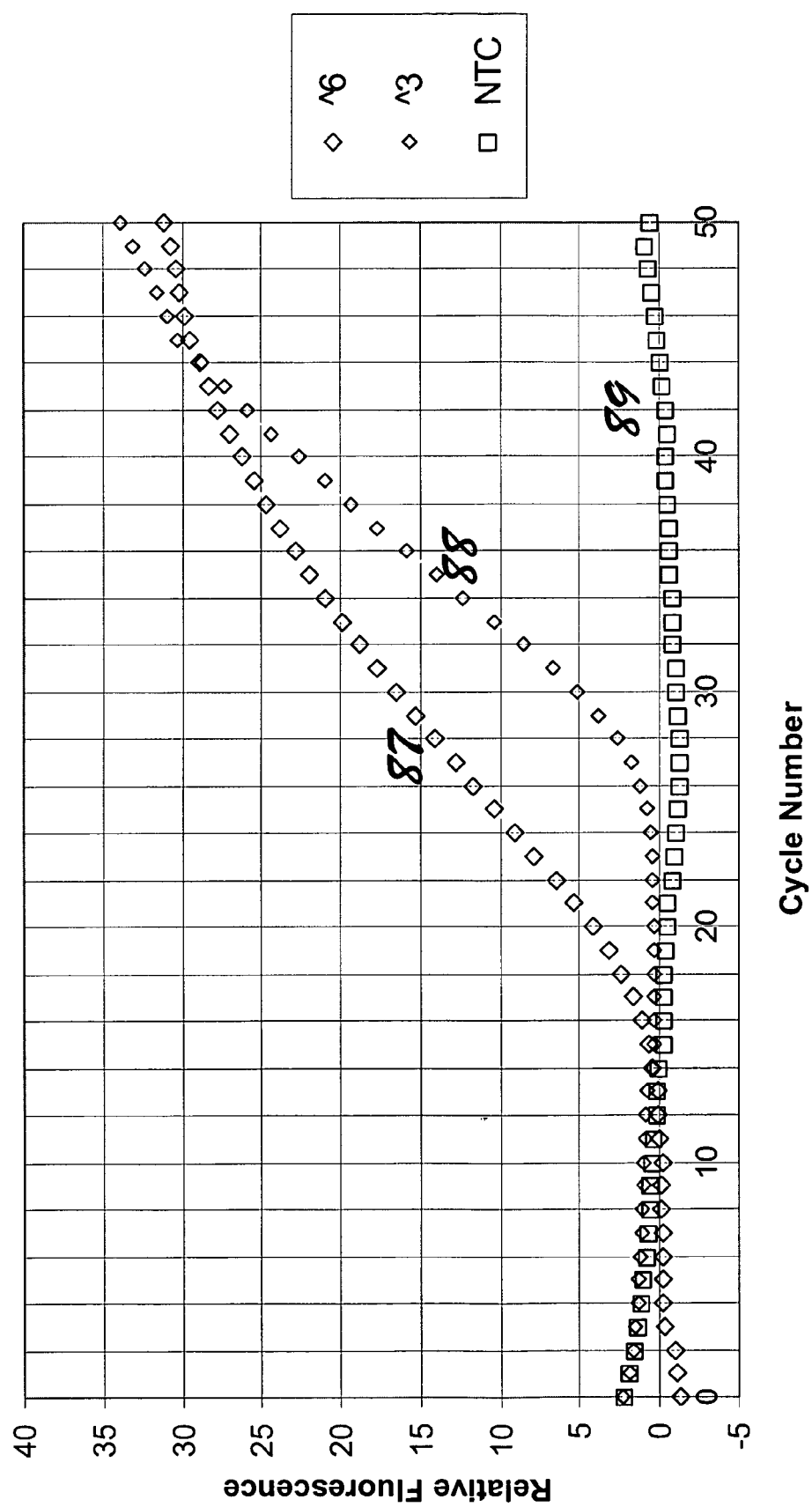

FIG. 9A illustrates data collected from amplifying the GAPDH gene by PCR and detected the product with doubly 5-CR110-labeled forward primer of GAPDH (SEQ ID No. 15). (Example 10)

Figure 9B:
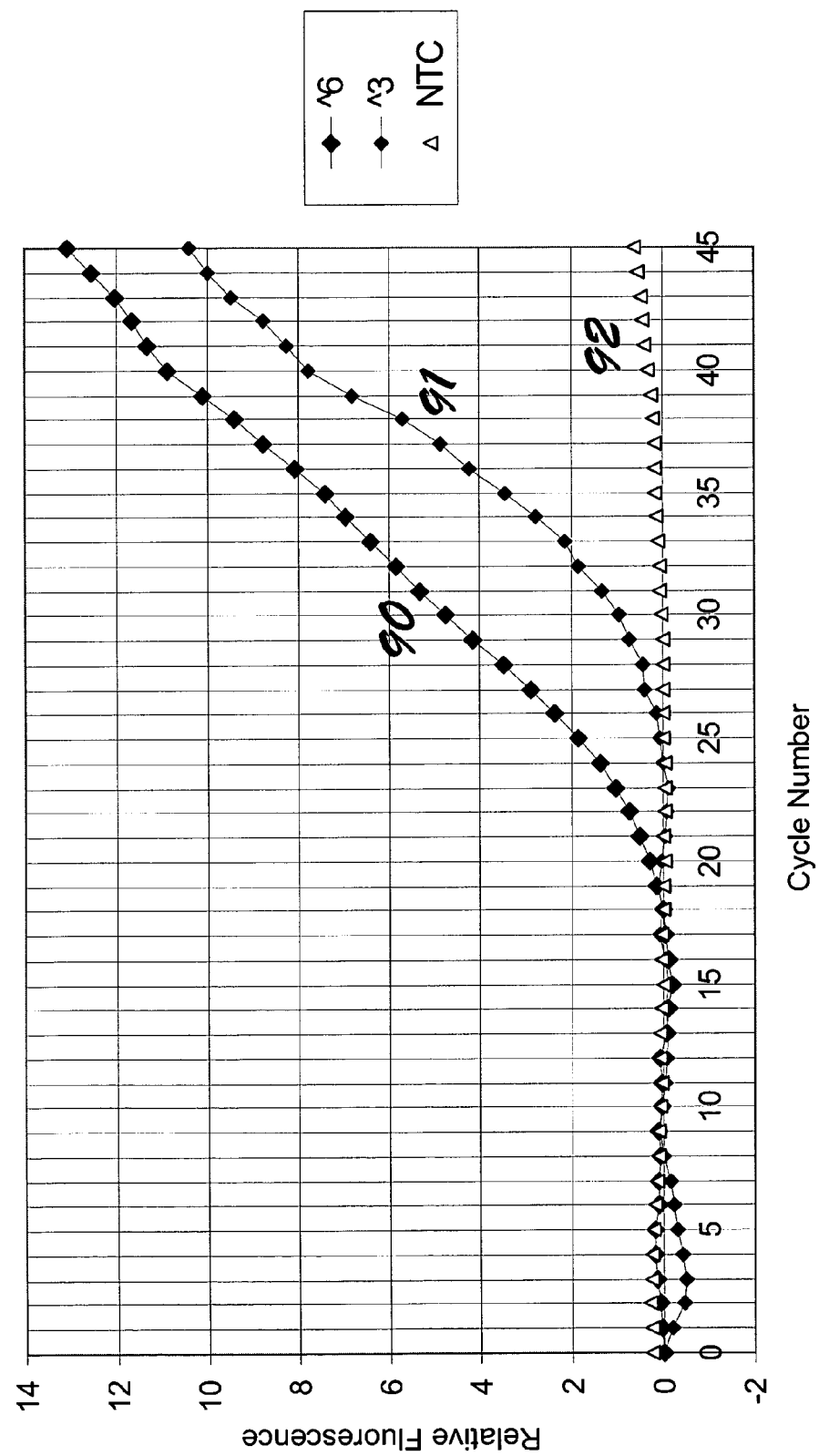

FIG. 9B illustrates data collected from amplifying the GAPDH gene by PCR and detected the product with doubly 5-CR110-labeled forward primer of GAPDH (SEQ ID No. 16). (Example 10)

Figure 9C:
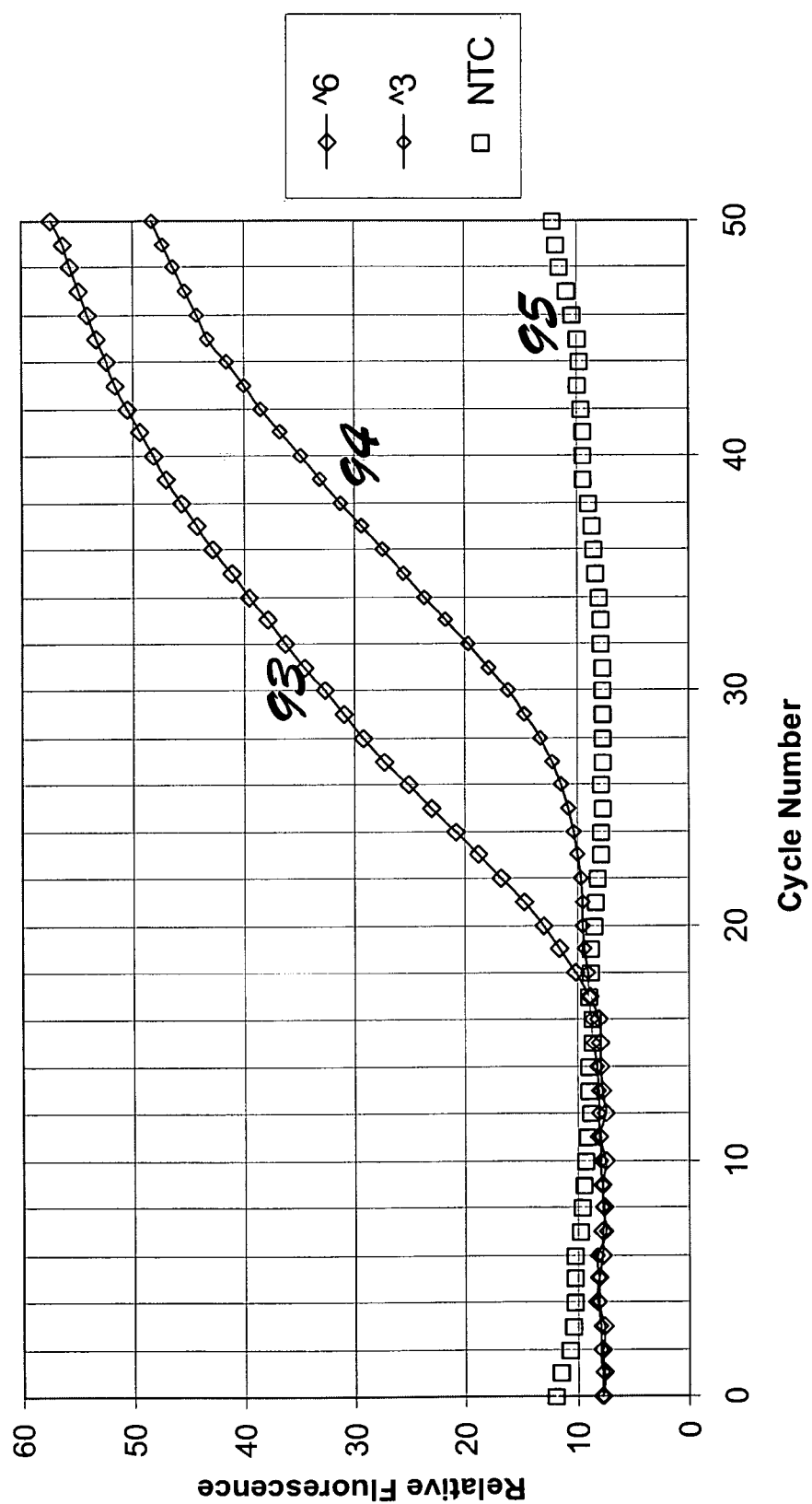

FIG. 9C illustrates data collected from amplifying the GAPDH gene by PCR and detected the product with 5-CR110-labeled reverse primer (SEQ ID No. 17). (Example 10)

Figure 9D:
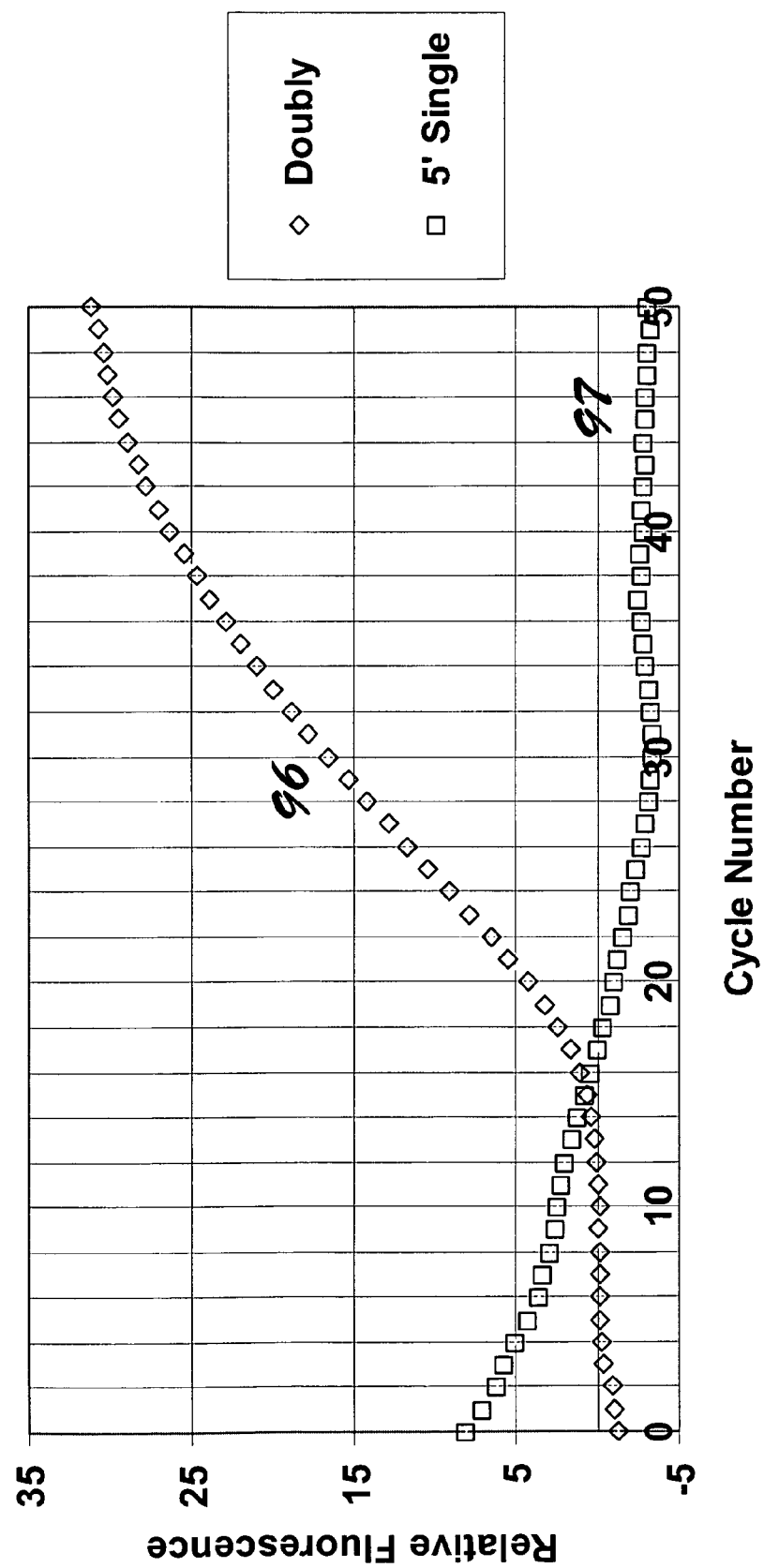

FIG. 9D illustrates data collected from amplifying the GAPDH gene by PCR and detected the product with doubly 5-CR110-labeled forward primer (SEQ ID No. 15) and the same forward primer singly labeled with 5-CR110 at 5' end (SEQ ID No. 18). This graph demonstrates that only the doubly labeled oligonucleotide functions as a fluorogenic primer. (Example 10)

Figure 9E:
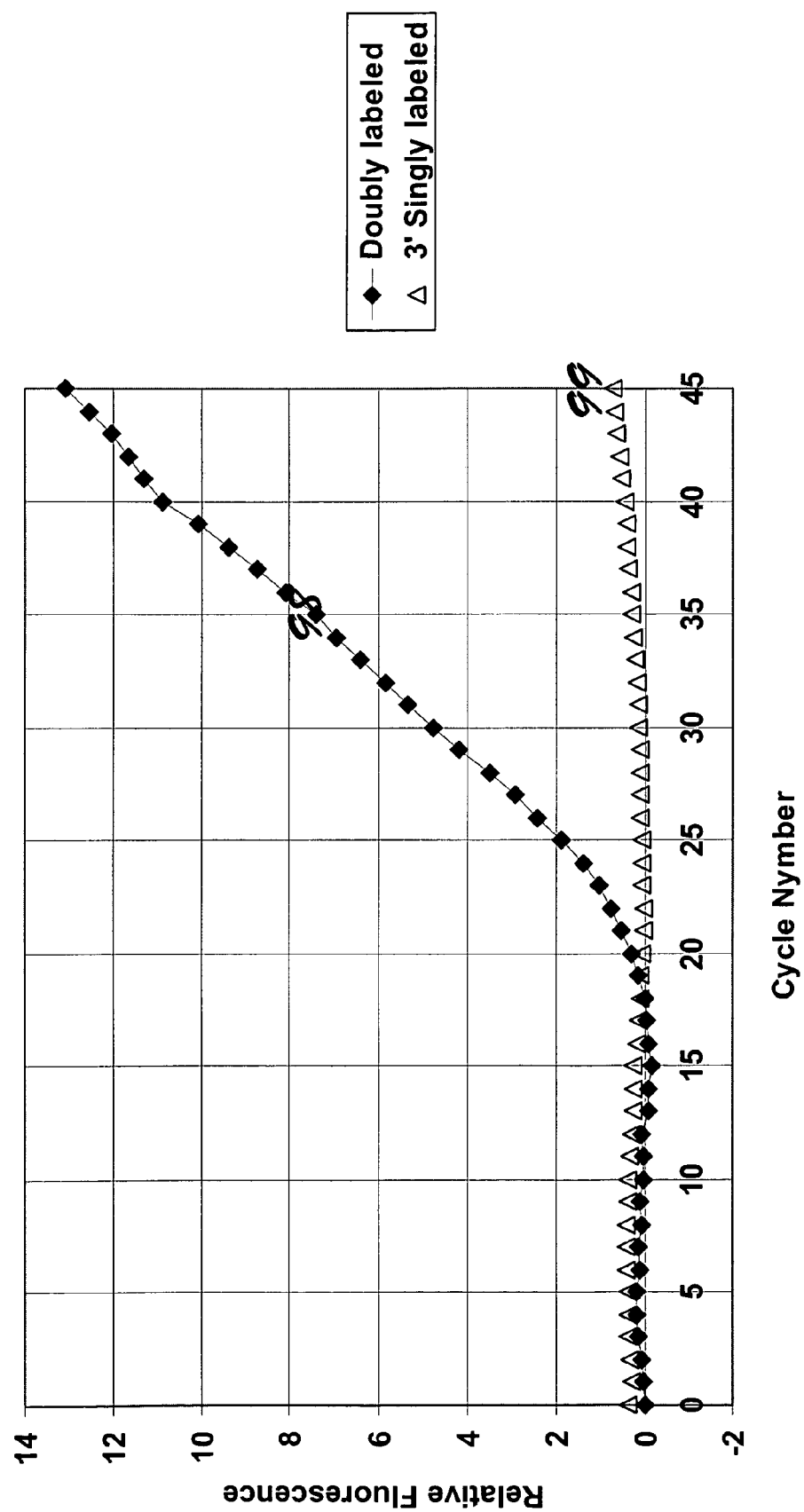

FIG. 9E is a comparison of data collected by amplifying the GAPDH gene by PCR and detecting the product with a doubly 5-CR110-labeled forward primer (SEQ ID No 16) and the same forward primer singly labeled at 3' end (SEQ No 19). This graph demonstrates that only a doubly labeled primer functions as a fluorogenic primer for PCR detection. (Example 10)

Figure 9F:
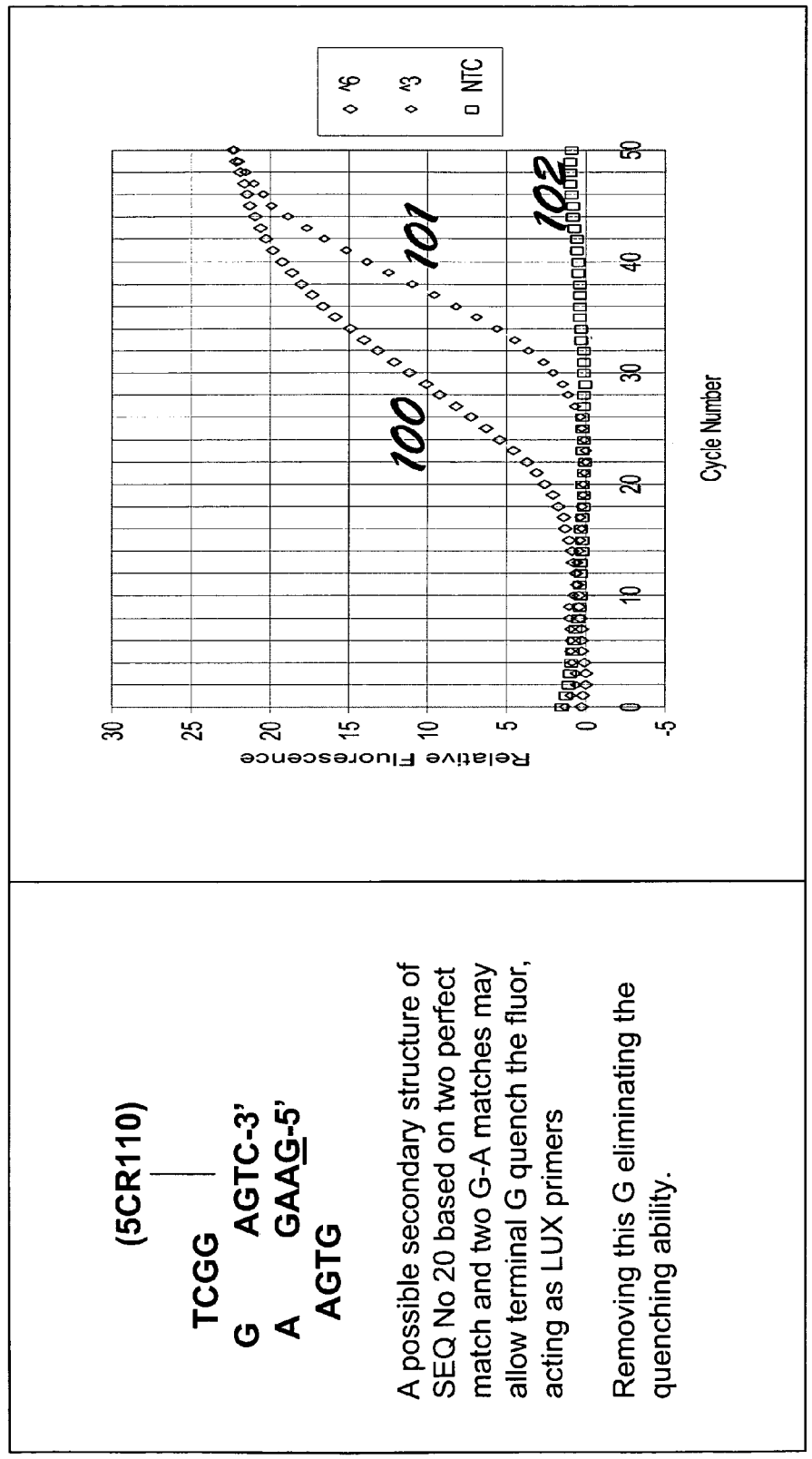

FIG. 9F illustrates a possible secondary structure that may allow a 5' G to act as a quencher as in a LUX primer. This figure also illustrates that fluorogenic primers of some embodiments of the present invention may work in accordance with a mechanism different from that which is responsible for the functioning of the LUX primers. (Example 10)

Figure 10:
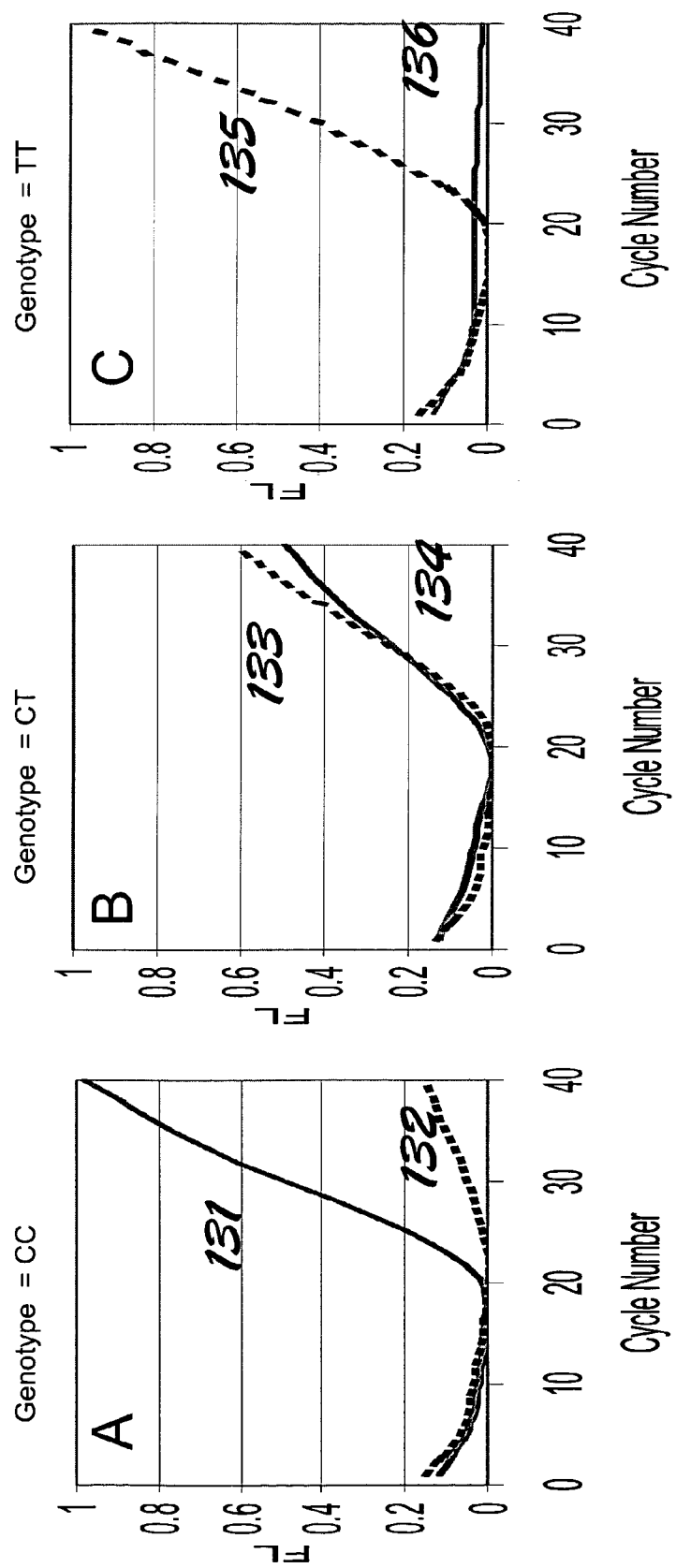

FIG. 10 illustrates SNP typing of model estrogen receptors. (Example 11)

Figure 11:
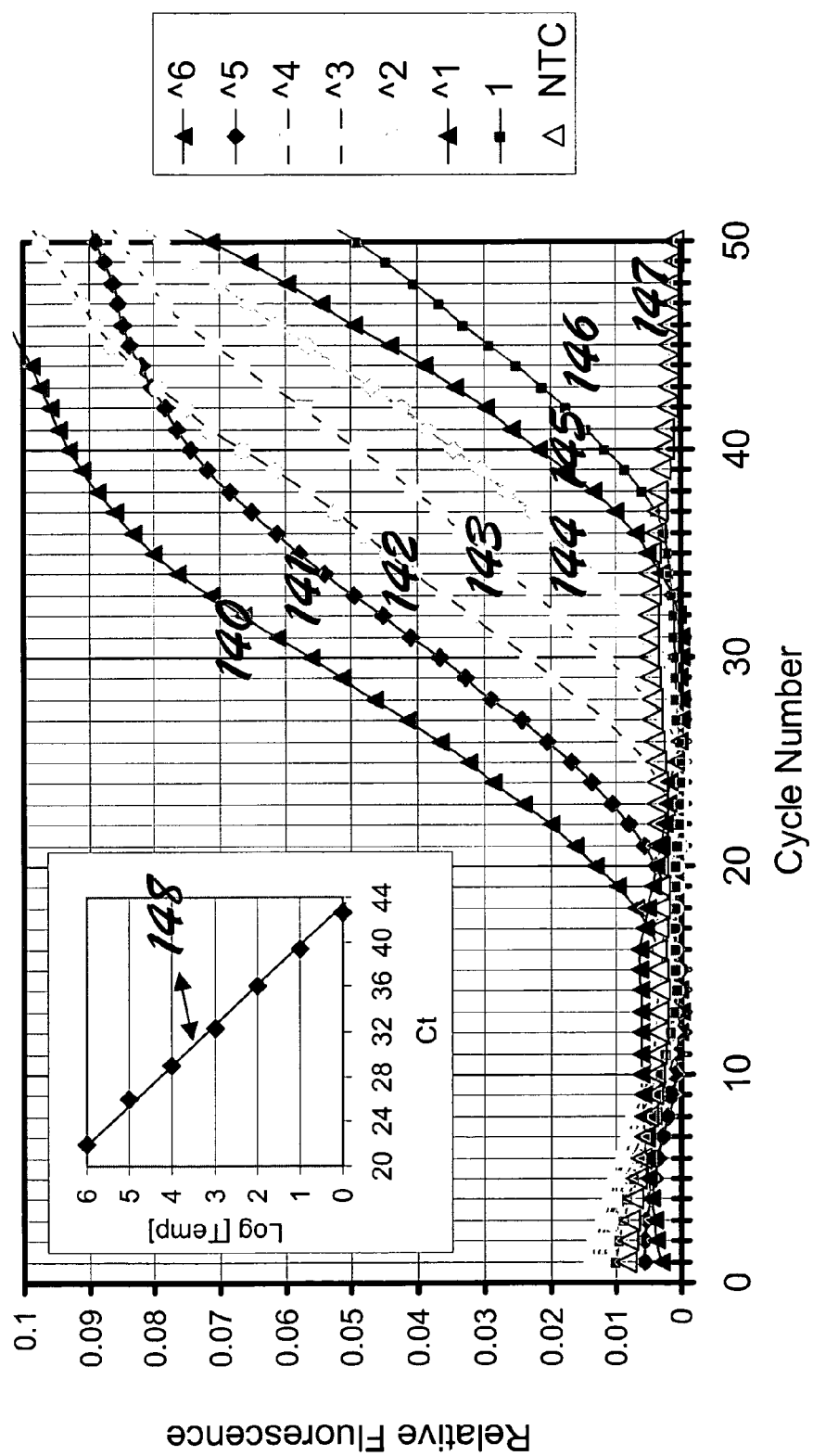

FIG. 11 illustrates data that was collected by amplifying the HCV gene by PCR and detecting the products using a doubly ROX-labeled probe (SEQ ID No. 33). As illustrated in the figure the signal was enhanced by treating the product with an enzyme, which exhibits an exo-minus activity, such as Taq DNA polymerase. (Example 12)

TABLE 1. A concise listing of some of the sequences referred to throughout the text as well as the structures of some of linking molecules suitable for practicing some embodiments.

TABLE 2. A partial listing of reactive groups including some electrophilic and nucleophilic groups that can be used in some embodiments to attach labeling molecules and quenching molecules to oligonucleotides.

SEQUENCE LISTING. An attached set of pages listing some of the sequences used in greater detail.

DETAILED DESCRIPTION

For the purposes of promoting an understanding of the principles of the invention, reference will now be made to the embodiments described herein and specific language will be used to describe the same. It will, nevertheless, be understood that no limitation of the scope of the invention is thereby intended. Any alterations and further modifications in the described devices, systems, and treatment methods, and any further applications of the principles of the invention as described herein, are contemplated as would normally occur to one skilled in the art to which the invention relates. While aspects of the invention may be discussed in terms of specific or general theories or principles, the invention is in no way bound by these theories or principles. Such discussion is purely illustrative and in no way limiting.

Because nucleic acid polymers play an essential role in modern medicine and the life sciences, a wide variety of reagents, including fluorescent dyes have been developed for use in processes for detecting, sequencing and measuring nucleic acid polymers. Similarly, a wide variety of methods have been developed for using these dyes to create ever more sensitive nucleic acid assays. One area that has generated intense study is the development of extremely sensitive assays for measuring the accumulation of nucleic acid polymers produced by PCR.

DNA amplification via PCR may be quite complex as the process is affected by many factors. One factor that effects PCR is the gradual depletion of starting components such as dNTP, primers, the effective concentration of $Mg^{2+}$ that occurs as the reaction progresses. Another factor is the inhibitory effect of the accumulating end product. During the PCR process these various components interact with each other in an interrelated dynamic fashion. Typically DNA amplification comprises three sequential phases: the exponential phase, the linear phase and the plateau phase. Each phase is different and may exhibit a different amplification efficiency than the other two. As a practical matter only data collected during the exponential phase can be used to reliably estimate the initial concentration of target oligonucleotide.

One method for monitoring PCR in real time that often uses fluorescent molecules is known commercially as the TaqMan assay. TaqMan assays exploit the 5'-exonuclease activity of the Taq polymerase to monitoring DNA amplification in real time. Further discussion of this well known assay is provided by Holland et al., *Proc. Natl. Acad. Sci. USA* (1991); Lee et al., *Nucleic Acids Res*. (1993); and U.S. Pat. Nos. 5,210,015; 5,538,848; 6,258,569 and 5,691,146). The TaqMan assay detects the accumulated PCR product via hybridization and subsequent cleavage of a fluorogenic probe (the "TaqMan" probe) during the amplification reaction. The probe is an oligonucleotide whose sequence is complementary to the target DNA to be detected. The probe is labeled with a single fluorescent reporter dye and a single fluorescence quencher. The reporter and quencher dyes are attached to the oligonucleotide with a separation of typically about 15 to about 60 nucleotides for optimal fluorescence quenching and 5'-exonuclease activity. The dye can be attached to either the nucleotide bases or the backbone of the oligonucleotide or a combination thereof. Typically, one of the reporter/donor labels is attached to the 3' terminal backbone phosphate and the other attached to the 5' terminal backbone phosphate. The quencher can be either a non-fluorescent dye or a fluorescent dye of appropriate wavelengths. In both cases, quenching of the fluorophore bound to the probe occurs via fluorescence resonance energy transfer (FRET).

In order to briefly discuss how to select a fluorophore/quencher pair and design a TaqMan probe that will exhibit optimal performance, it is useful to review some basic photophysics. Firstly, when a dye receives a photon of sufficient energy from an external source, it is electronically excited to the singlet excited state. The excited state exists for a finite time, during which period the electronic energy is partially dissipated into vibrational and rotational modes of the molecule. Consequently, when the dye emits the photon, the energy of the photon is lower and thus the wavelength of the photon emitted by the molecule is longer than the wavelength of the photon absorbed by the molecule. This energy or wavelength difference between excitation, or absorption, and emission is called the Stokes shift and is common among fluorescent dyes. Secondly, FRET-based quenching is governed by Förster's resonance energy transfer theory, which states that the efficiency of photo energy transfer is positively related to the overlap of emission spectrum of the donor and absorption spectrum of the acceptor. Further discussions of this is provided in Förster, *Ann. Phys.* (1948); and Stryer et al., *Proc. Natl. Acad. Sci.* (1967). The combination of the Stokes shift and the spectral overlap requirement necessitates that the fluorescent donor and acceptor be different dyes. This is true even if the donor and quencher molecules are both fluorescent dyes.

In fact, a quencher molecule that is also a fluorescent dye should ideally be selected to have a wavelength of emission that is significantly longer than the emission wavelength of the donor (reporter) dye. Using this combination ensures a dark background. An additional gain in sensitivity can be achieved by using a filter that selectively blocks all or most of the signal emitted by the quencher molecule. For optimal performance then, quenchers are preferably chosen from molecules that are themselves completely non-fluorescent. Indeed, achieving a low or zero background for TaqMan assays has been the focus of considerable research effort. To this end, many non-fluorescent quencher molecules have been developed. Well known commercially available non-fluorescent quenchers include, for example, Black Hole Quencher (BHQ) dyes from Biosearch, which are non-fluorescent azo dyes and Eclipse Dark Quencher (DQ) from Epoch (Eurogentec catalog number OL-0273-DQ02), and IOWA Black (IWB) from Integrated DNA Technologies. Further discussion of these molecules is provided by Johansson, M. K, et al, *J. Am. Chem., Soc.*, (2002). These and similar non-fluorescent quenchers improve the sensitivity of TaqMan probes by suppressing background fluorescence, thereby increasing the signal gain following enzymatic cleavage of the probe. Examples of popular donor/acceptor (fluorophore/quencher pairs used in TaqMan probe design include FAM/TAMRA, VIC/BHQ1, HEX/BHQ2, and TET/DHQ and the like.

In addition to the spectral overlap requirement stated above, a second parameter critical to FRET-based fluorescence quenching is the distance between the donor and acceptor. FRET is dependent on the inverse sixth power of the intermolecular separation.

Prior to hybridization with a target nucleic acid, a typical TaqMan probe assumes a random conformation, wherein the donor and quencher are able to move close enough to one another for efficient FRET to occur. Because of their proximity to one another and their spectral characteristic the reporter molecule, is quenched and therefor the probe, is non-fluorescent. Upon hybridization with the segment of a target DNA being amplified, the probe is stretched and consequently becomes fluorescent because the increased distance between the donor and quencher makes FRET energy transfer impossible. Alternatively, and often preferably, the probe is digested during amplification by, for example, using a polymerase that has 5'-exonucleas activity. Digestion completely frees the donor dye from being in proximity to the quencher, thereby further reducing quenching and further enhancing the fluorescence signal from the donor dye. As more DNA copies are made during the PCR amplification, more probes are hybridized and then cleaved, which in turn increases the fluorescence signal. A variation of this scheme is the use of a two-enzyme system. In this system one enzyme is responsible for polymerizing the oligonucleotide and the second enzyme is responsible for cleaving the reporter dye from the PCR product. One such commercially available product that exploits this strategy is the Full Velocity kit available from Stratagene.

Another variation of probe design that exploits FRET to create probes with good signal to noise ratios is described in U.S. Pat. No. 6,492,346. This variation employs a minor groove binding molecule (MGB) covalently linked to the 3'-end, 5'-end, or any other position within the oligonucleotide probe. Probes containing a MGB may have a shorter nucleotide sequence than probes that do not use MGBs and still exhibit very efficient fluorescence quenching. In addition, probes labeled with a MGB tend to have improved specificity, efficiency and enhanced discrimination against mismatches relative to probes labeled by certain other labeling molecules that do not selectively bind to the minor groove.

Still another method of detecting amplification products uses the so-called "molecular beacon probe" which is the subject of U.S. Pat. Nos. 5,925,517; and 5,118,801 and 5,312,728. Molecular beacon probes have stem-loop structures including a central target-recognition sequence (loop region) that is flanked by a pair of complimentary 3' and 5' terminal sequences that hybridize to each other to form a stem structure. A fluorescence donor dye and quencher molecule are attached to the 3' and 5' terminals, respectively. In the absence of a complementary target sequence the beacon probe stays in its closed conformation, and the fluorescence of the donor dye is quenched by the quencher dye via FRET. Upon hybridization with a target sequence, the beacon probe stretches to an open conformation, thereby separating the donor dye and quencher, and increasing the fluorescence signal of the donor dye. As additional copies of a target DNA are generated during the course of a PCR reaction, more beacon probes adopt the open conformation by hybridizing to the target DNA and the fluorescence signal rises accordingly. Further discussion of this technique is provided by Tyagi et al., *Nature Biotechnol.* (1996). Unlike TaqMan probes, which are "consumed" via enzymatic cleavage of the probes during PCR, molecular beacon probes remain chemically unchanged throughout the DNA amplification process; only the conformation of the beacon probes changes from the closed form (stem-loop) to the open form.

The two conformations of the beacon probes—open and closed—exist in a dynamic equilibrium with one another. During PCR the equilibrium depends on three competing hybridization reactions between each pair of complementary strands. The three equilibria are between: 1) the two complementary strands of the target DNA; 2) the complementary 3' and 5' ends (stem) of the probe; and 3) the target-recognition sequence of the probe (loop) and the target sequence. Only the third hybridization reaction favors the open beacon conformation and thus only one produces a detectable fluorescence signal. Both the first and second hybridization reactions favor the closed beacon conformation and in turn reduce the fluorescence signal. Because of the competing hybridization interactions (1 and 2), a molecular beacon probe is inherently less sensitive in nucleic acid detection than a TaqMan probe labeled even when both are labeled with the same or similar donor/quencher dye pair. However, a beacon probe hybridized to a target sequence can also be cleaved from the oligo as is a TaqMan, probe if an enzyme with 5'-exonuclease activity is used in the reaction. In this instance, a beacon probe has become a de facto TaqMan probe.

Still another method is disclosed in U.S. Pat. No. 6,174,670, this method uses an energy transfer system in which energy transfer occurs between two hybridization probes. For example, the first probe is labeled at the 3' end with a fluorescence donor dye, while the second probe is labeled at the 5' end with a acceptor dye. The acceptor molecule on the second primer emits energy at a longer wavelength than the donor dye on the first primer. When employed in PCR, the two probes hybridize to one of the two complementary strands of a target DNA in a head to toe arrangement. Because of how the two donor and acceptor dyes are positioned FRET occurs between these two molecules. Accordingly, by measuring the fluorescence emission of the acceptor dye, one can relate the fluorescence intensity to the amount of a target DNA being generated as the PCR progresses.

Yet another method of detecting amplification products is disclosed in U.S. Pat. No. 6,635,427. This method uses an internal guanosine (G) nucleotide as a quencher (acceptor) for a single reporter dye attached to an oligonucleotide probe. In the absence of a target sequence, the guanosine nucleotide, which is usually strategically positioned near to the position of the reporter dye, quenches the fluorescence of the reporter dye. Upon hybridization with the target sequence, quenching by guanosine is reduced, leading to an increase in the fluorescence signal.

PCR can also be monitored by using of fluorogenic primers that become fluorescent upon incorporation into the amplification products. One such method that uses a beacon-like hairpin primer labeled with a donor/quencher dye pair is known commercially as Ampliphore, and is disclosed in U.S. Pat. No. 5,866,336 Patent. Prior to hybridizing to its target DNA sequence, the primer exists in the closed hairpin conformation, which quenches the fluorescence of the donor dye via FRET. Once hybridized to the target DNA sequence and incorporated into the amplification product, the primer assumes an extended open conformation and the primer becomes fluorescent because FRET is diminished. In order to achieve the required specificity of a primer as well as to maintain the necessary hairpin structure, a beacon-like primer is usually quite long. The length of the probe imposes restrictions on primer design and adds to the cost of synthesizing the primer.

Another method of monitoring PCR uses a primer known commercially as the LUX primer. Further discussion of this technique is provided by Nazarenko et al., published in *Nucleic Acid Research* (2002); and -Marras et al., *Nucleic Acid Research* (2002). LUX primers are labeled with a single fluorescent dye (donor molecules) positioned strategically near an internal guanosine (G) nucleotide that acts to quench the fluorescence of the dye. The labeled primer in its free form is non-fluorescent or weakly fluorescent due to the interaction between the dye and the G nucleotide that is near to it. When the primer is extended and the G nucleotide is internalized in double stranded DNA, fluorescence quenching is reduced or eliminated and the fluorescent signal from the donor molecule increases. LUX primers have the advantage of being relatively simple in design. One problem with the LUX system is that it requires the presence of a G nucleotide near the dye attachment site (usually thymidine) this restricts choices in primer design. Furthermore, the fluorescence quenching by G only works well with a very few dyes of selected wavelength. The restriction on primer sequence and, especially, the incompatibility with longer wavelength dyes make it difficult to develop a set of LUX primers for use in multiplex PCR.

More recently, BD Biosciences developed a fluorescence-based primer kit known commercially as DNAzyme for use in RT-PCR. This method employs a combination of a fluorogenic oligonucleotide and primers and is disclosed in US Patent Application Publication No. 2001/0001063. In addition to the normal initiation sequence for the extension reaction, one of the primer sequences encodes an enzyme that cleaves the fluorogenic oligonucleotide during primer extension. The result, as with the TaqMan assay, is in an increase in the fluorescence signal. The fluorogenic oligonucleotide used in the primer kit is similar in design to a typical TaqMan® probe except that the former does not have a sequence complimentary to the target sequence and as a result this technique lacks the specificity of TaqMan based assays. Furthermore, because of the need to code for the requisite enzyme, the DNAzyme primer can be easily over 50 nucleotides long. The need for a longer nucleotide increases the cost of manufacturing the primer.

One major advantage of fluorogenic probes over fluorogenic primers is that fluorescence signal detected from probes derives only from hybridization between probe and target. Non-specific amplification of signal due to mis-priming or primer-dimer artifacts, as sometimes occurs with primers and does not generate useful signals, does not generally occur with probes. Fluorogenic probes can be labeled with different, distinguishable reporter dyes. By using several probes each labeled with a unique reporter dye, amplifications of multiple targets with distinct sequences can be detected in a single PCR reaction. This method is commonly referred to as multiplex PCR. The development of fluorogenic probes has also made it possible to eliminate post-PCR processing, thereby eliminating the possibility of cross-contamination, which is a critical factor for clinical diagnostics and forensic applications.

One disadvantage of fluorogenic probes is their cost. A fluorogenic oligonucleotide is at least 10 times more expensive than the corresponding unlabeled oligonucleotide. Furthermore, probe design is relatively complex and one often needs to consider many factors such as the length of probe, annealing temperature and proper spectral matching of quencher to fluorophore when constructing a suitable probe.

Compared with fluorogenic oligonucleotide probes, particularly TaqMan probes, fluorogenic primers tend to generate a weaker signal because they are not cleaved during PCR to allow permanent separation of the reporter dye from the quencher. Additionally, non-specific PCR products resulting from mis-priming and primer dimer formation also contribute to increasing noise in the assay. For these reasons, fluorogenic probes are generally preferred over fluorogenic primers for use in real time quantitative PCR.

Numerous methods have been developed for labeling oligonucleotides. Typically a fluorescent donor dye and a quencher are attached to the oligonucleotides in a stepwise fashion. These processes often involve expensive reagents and complex protection/de-protection steps and the yields are often quite low. Moreover, the choice of dyes and quenchers as well as the order in which they are attached to the oligonucleotides are limited and inflexible, in part, because not all dyes can tolerate the harsh chemical conditions of oligonucleotide syntheses.

Typically, a dye is incorporated into an oligonucleotide via one of two methods: 1) by using a dye-modified nucleoside or deoxynucleoside phosphoramidite during automated synthesis; or 2) in a post-synthesis labeling by reacting an amine- or thiol-modified nucleotide or deoxynucleotide with an amine- or thiol-reactive dye. For example, an oligonucleotide labeled with a FAM/TAMRA dye pair at the 3' and 5' termini is typically synthesized by starting with a TAMRA-labeled modifier attached to CPG solid support, followed by successive buildup of the remaining oligonucleotide. The donor dye FAM is attached to the oligo at the last coupling step via standard phosphoramidite chemistry. This approach has two drawbacks: first, dye-labeled phosphoramidite is costly; second, it diminishes the quenching ability of TAMRA because rhodamine dyes in general, and TARMA, in particular are unstable under the standard oligonucleotide synthesis condition. To address this problem, it is a common practice to avoid starting with TAMRA linked to CPG support. One approach is to start the synthesis with a protected 3'-amino-modifier linked CPG and the donor dye FAM is attached to the 5'-end as usual at the last step of the automated synthesis via standard phosphoramidite chemistry. Following subsequent oligonucleotide cleavage from the solid support and a 3'-amine de-protection step, the amine-modified oligonucleotide is reacted with a TAMRA succinimidyl ester. To ensure the performance of the probe or primer, purification steps using either HPLC or polyacrylamide gel electrophoresis are necessary both before and after to the second dye attachment reaction. The limitations and inflexibility imposed by the designs of the probes and primers as well as the nature of the labeling chemistry make these fluorogenic oligonucleotides very expensive to manufacture.

Figure 1:
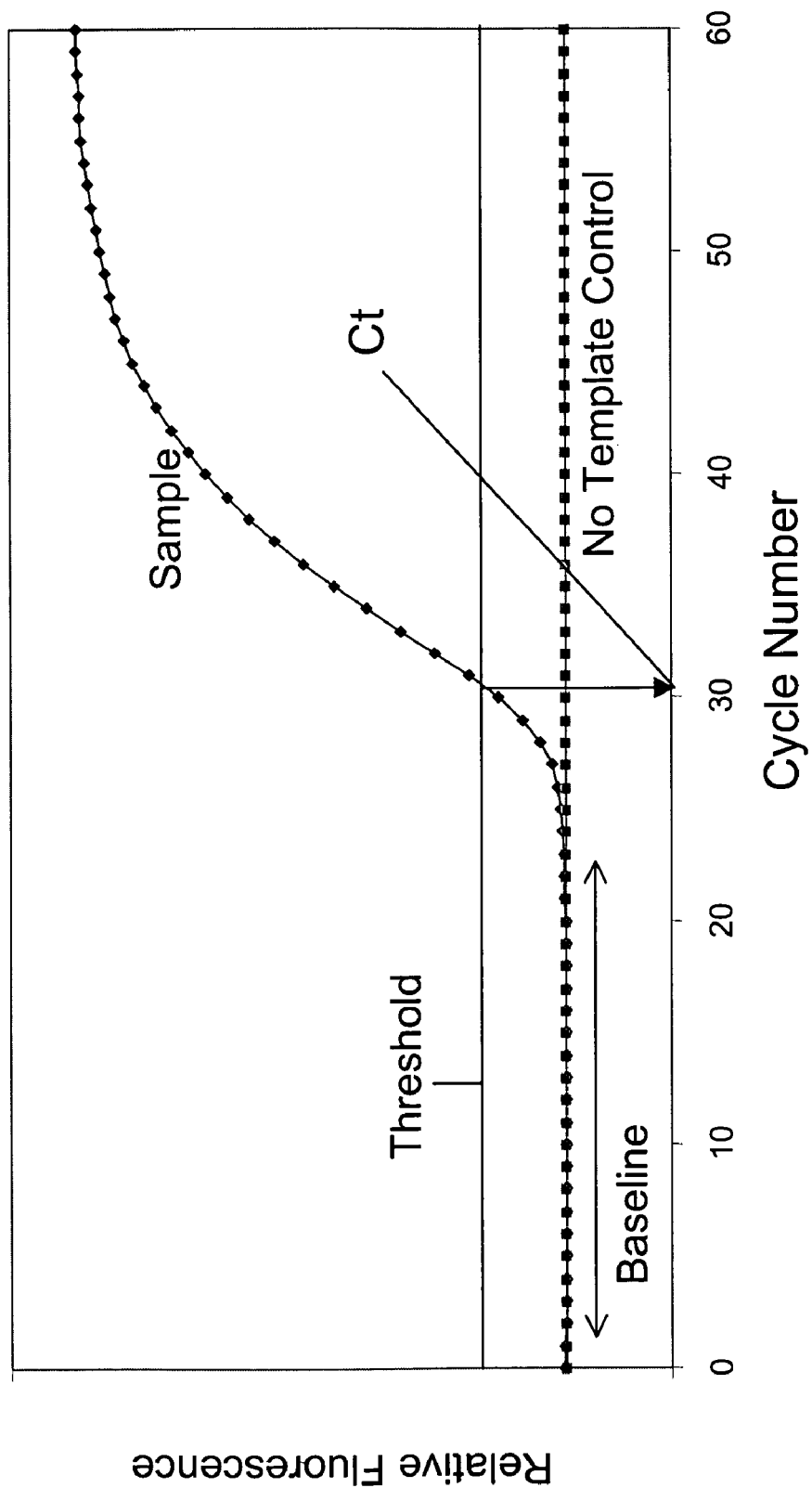
FIG. 1 is a schematic amplification plot for a typical real time PCR run that illustrates some of the parameters associated with real time PCR.

An increasing important type of PCR assay that makes use of labeled oligonucleotides is real-time PCR. One important parameter for a real-time PCR monitoring is the so-called threshold cycle point, or Ct value. The Ct value is the theoretical number of reaction cycles needed for the fluorescent signal of the PCR product to reach a pre-set value above the baseline. The higher the concentration of a target DNA in the sample, the smaller the Ct value will be. FIG. 1 shows a representative amplification plot and defines the terms used in the quantification analysis. An amplification plot is the plot of fluorescence signal versus cycle number. In the initial cycles of PCR, there is little change in fluorescence signal. This relatively "flat region" defines the baseline for the amplification plot. An increase in fluorescence above the baseline indicates the detection of accumulated PCR product. The logarithm of initial target copy number is reversibly correlated to Ct value in a linear fashion, and this relationship forms the mathematical basis for real-time quantitative PCR.

DEFINITIONS OF SOME OF THE TERMS USED HEREIN

The terms "oligonucleotide" and "oligo" are used interchangeably and refer to a sequence of nucleic acids, 2'-deoxynucleic acids, peptide nucleic acids (PNA), locked nucleic acid (LNA) and other unnatural nucleic acids which include pyrazolo pyrimidine. In general oligonucleotides are of a length suitable for use as primers or probes. Most oligonucleotides are polynucleotides generally less than 100 nucleotides long, many are less than 50 nucleotides long and a number of oligonucleotides are comprised of 25 or fewer nucleotides. For a more thorough discussion of the term the reader is directed to the following references Kutyavin, I., et al., *N. A. R.* 30, 2002:4952-4959; and He J. & Seela F., *N. A. R.* 30, 2002:5485-5496 and references therein.

"Primer" refers to an oligonucleotide that is capable of acting as a starting point to extend along a complementary strand. Primers usually are used as a set in PCR, one forward and one reverse. The forward primer contains a sequence complementary to a region of one strand of target nucleic acid and guides the synthesis along this strand. Similarly the reverse primer contains a sequence complementary to the opposite stand of the target nucleic and guides the synthesis along the opposite strand of target nucleic acid.

"Probe" refers to a labeled oligonucleotide containing a sequence complementary to a region of the target nucleic acid, wherein the labeled oligonucleotide anneals to the target sequence and generates a signal indicating the presence of the region of the target. The probe is generally blocked at the 3' terminus and is not extended into products.

The term "photometric labeling molecule" refers to molecules that generate a detectable change signal due to change in the molecule's physical or chemical environment and used to label another molecule. The change may be in the amount of light absorbed or in the wavelength of light absorbed. Photometric molecules include, for example, fluorescent dye molecules that absorb light at one length and emit light at another wavelength. In the case of photometric labeling molecules that are fluorescent dyes the molecules may also exhibit a change in the amount of light emitted or in the wavelength of the light emitted.

The term 'reactive groups' refers to chemical moieties that may be useful in attaching various labeling groups including fluoropores and quenching molecules to oligonucleotides. The choice of reactive group used to attach the dye to an oligo typically depends on the functional group on the oligo to be labeled.

The bond formation reaction between a reactive group of, for example, a dye molecule and a functional group of a oligo is typically a reaction between a nucleophile and an electrophile. Accordingly, a reactive group can be either a nucleophile or a electrophile, and correspondingly a functional group can be either an electrophile or a nucleophile. A non-exhaustive list of pairs of electrophile/nucleophile can be found in Table 2. For a further discussion of reactive pairs the reader is directed to U.S. Pat. No. 6,130,101.

Typical functional groups present on an oligo include, but are not limited to, amines, thiols, alcohols, phenols, aldehydes, ketone, hydrazines, hydroxylamines, disubstituted amines, halides, or carboxylic acids. More typical functional groups on an oligo are amines, thiols, alcohols, aldehydes or a ketones.

Common reactive groups attached to a dye molecules include, but are not limited to: acrylamide, an activated ester of a carboxylic acid, an acyl azide, an acyl nitrile, an aldehyde, an alkyl halide, an amine, an anhydride, an aniline, an arylhalyde, an azide, an aziridine, a carboxylic acid, a haloacetamide, a halotriazine, a hydrazine, a hydrazide, an imido ester, an isocyanate, an isothiocyanate, a maleimide, a phosphoramidite, a sulfonyl halide or a thiol. Other reactive groups include succinimidyl ester, an amine, a haloacetamide, a hydrazine, an isothiocyanate, maleimide, or a phosphoramidite. When the functional groups present on the oligonucleotide are amines one commonly used reactive group on the dye used to attach the dye to the oligonucleotide is a succinimidyl ester.

Some of the abbreviations used for various reagents including dyes are as follows: 5-CR110 refers to 5-carboxyrhodamine110; 6-CR110 refers to 6-carboxyrhodamine110; 5-FAM refers to 5-carboxyfluorescein; 6-FAM refers to 6-carboxyfluorescein; 5-R6G refers to 5-rhodamine 6G; 5-ROX refers to 5-carboxy-X-rhodamine; 6-ROX refers to 6-carboxy-X-rhodamine; 5-TAMRA refers to 5-carboxytetramethylrhodamine; 6-TAMRA refers to 6-carboxytetramethyl-rhodamine; JOE refers to 2',7'-dimethoxy-4',5'-dichloro-6-carboxyfluorescein The term "spectrally similar dyes", for the purpose of the present invention, refers to fluorescent dyes that may or may not have similar chemical structures but possess similar excitation and/or excitation spectral properties. The emission spectra of the dyes, however, may or may not be similar. An example of one such pair is 5-FAM and 5-CR110. 5-FAM has absorption/emission wavelengths at 495/519 nm while 5-CR110 has absorption/emission at 502/524 nm. For the purpose of the present invention, absorption or excitation wavelengths having a difference within 15 nm are considered to be similar.

The term "spectrally identical dyes" refers to fluorescent dyes that may or may not have the same chemical structures but have either emission profiles or excitation or both emission and excitation profiles that are spectrally indistinguishable.

The term "same dyes" refers to fluorescent dyes that are both chemically and spectrally identical.

The term "reporter dye" or "fluorescent reporter dye" refers to a fluorescent dye whose fluorescence is monitored during an assay. When a quencher dye is also used to label the same biomolecule, a reporter dye may be referred to as a donor dye and the quencher dye may sometimes be referred to as an acceptor, acceptor dye or acceptor molecule.

As used herein, the terms "quench" or "quenches" or "quenching" or "quenched" refer to reducing the signal produced by a molecule, it includes, but is not limited to, reducing the signal produced to zero or to below a detectable limit. Hence, a given molecule can be "quenched" by, for example, another molecule and still produce a detectable signal albeit the size of the signal produced by the quenched molecule will be smaller when the molecule is quenched than when the molecule is not quenched.

The term "quencher" or "quencher dye" or "quencher molecule" refers to a dye or an equivalent molecule, such as nucleoside guanosine (G) or 2'-deoxyguanosine (dG), which is capable of reducing the fluorescence of a fluorescent reporter dye or donor dye. A quencher dye may be a fluorescent dye or non-fluorescent dye. When the quencher is a fluorescent dye, its fluorescence wavelength is typically substantially different from that of the reporter dye and the quencher fluorescence is usually not monitored during an assay.

Some embodiments of the present invention disclose methods for constructing fluorogenic oligonucleotides and their uses as primers and probes for the purpose of nucleic acid detection, particularly nucleic acid detection in real-time qPCR. Compared with existing technologies, fluorogenic oligonucleotides of some embodiments are significantly easier to manufacture and substantially more sensitive than many commercially available technologies. Furthermore, unlike conventional fluorogenic oligonucleotides, such as the TaqMan probes, whose choice of a reporter dye is limited by the availability of the accompanying quencher dye, oligonucleotides of various embodiments of the present invention can accommodate fluorescent dyes of virtually any wavelength. This flexibility in dye selection facilitates syntheses of fluorogenic primers or probes of different fluorescent wavelengths and allows multiplex detection in a single-tube format.

Some embodiments are probes that are single-stranded oligonucleotides labeled with a plurality of spectrally identical or similar fluorescent dyes. The probes may be further labeled with one or more quenchers. In the absence of a target sequence, the probes assume a random coiled conformation, and are either non-fluorescent or only weakly fluorescent. Generally, an oligonucleotide with a random coiled conformation is substantially free of secondary structure that serves to bring the two termini of the oligonucleotide in proximity with one another. In contrast, an example of oligonucleotide probes having a secondary structure is the so-called molecular beacon probe.

In the presence of a target sequence, probes of various embodiments readily hybridize to the target sequence. In the presence of specific reagents or enzymes with 5'exonuclease activity the dye molecules are subsequently cleaved from the oligonucleotide. Cleavage results in permanent separation of the dye molecules resulting in a large increase in fluorescence.

Maximal fluorescent increase is dependent on the cleavability of the phosphate backbone linking each neighboring dye pair by the 5'-exonuclease or an equivalent nuclease. When the dye attachment sites are too close to each other, hybridization of the oligonucleotide to the target and 5'-exonuclease activity may be hindered. On the other hand, when the dye attachment sites are too far away from each other, background fluorescence may be high. Thus, to achieve minimal fluorescence background in the absence of a target sequence and optimal 5'-exonuclease activity following probe/target hybridization, each neighboring pair of dye attachment sites should be separated by 3 to 60 nucleotides, preferably by 12 to 35 nucleotides, and most preferably by 15 to 25 nucleotides.

Useful enzymes for use with these embodiments include Taq polymerase or a stand-alone exonuclease, or any other enzyme that can cut between the two labeling molecules. In some embodiments, permanently separating the labeling molecules substantially increased fluorescent emission.

In contrast to the multiple labeling molecules incorporated into oligos labeled according to the invention, fluorogenic probes such as the TaqMan probes disclosed in U.S. Pat. No. 5,538,848, Molecular Beacons disclosed in U.S. Pat. No. 5,925,517 and the Hyb probes disclosed in U.S. Pat. No. 6,174,670 include only single fluorescent reporter. As a result, the maximum fluorescent signal that currently available probes can generate is the signal produced by a single fluorophore. On the other hand, probes of various embodiments of the present invention include at least two dyes. Accordingly, hybridization with a target sequence and cleavage of the probes of the present invention results in the generation of signal from multiple fluorescent dyes. Accordingly, probes of various embodiments of the present invention are capable of generating fluorescent signal many times stronger than the signals generated by probes made in accordance with the currently available methods.

FIG. 3A illustrates the result of comparing the kinetic fluorescence measurements of a typical MCG gene amplification reaction detected with a TagMan probe (JOE as the fluorophore and TAMRA as the quencher) and the same reaction detected with a probe made in accordance with one embodiment of the present invention. The probe made in accordance with one embodiment of the instant invention was labeled with two R6G dyes at the two termini (See Example 4). The same sequence was used in both assays.

As the data in FIG. 3A illustrate the fluorescence signal from the doubly labeled probe is twice that of the signal measured using the TaqMan probe. It is a surprising observation that an oligonucleotide labeled with two or more identical or spectrally similar fluorophores is sufficiently quenched (without forming dye aggregates) that separation of the fluorophores from one another by cleavage of the probe generates a signal high enough above background to be useful in tracking the amplification of DNA. Because this observation with oligonucleotides was so unexpected, we looked for an explanation to techniques that use fluorescent dyes to measure the level of another biopolymer polypeptides.

Proteins are sometimes labeled with antibodies tagged with fluorescent dyes. In these assays it is common to attach two or more identical fluorophores to a single polypeptide. The additional of each dye molecule increases the overall fluorescence of the labeled proteins, although the fluorescence increase over the number of dyes may not be linear due to fluorescence quenching related to physical touching of the dyes. In protein labeling experiments significant fluorescence quenching occurs, only when an excess number of dye molecules are attached to the protein. In such cases, the quenching is often a result of the physical interaction among the dye molecules namely dye aggregation. Further discussion of this technique is provided in Haugland, RP *Handbook of Fluorescent Probes and Research Products* 9$^{th}$ edition, pp. 20-74 and references therein.

In contrast to relatively highly structured polypeptides, oligonucleotides lacking complimentary internal sequences are expected to assume unstructured, unpacked, extended structures. This conformation is generally referred to as random coil and is characterized by a lack of readily definable internal secondary structure. Oligonucleotides are believed to adopt the random coil conformation in order to minimize inter molecular electrostatic repulsion due to the highly negatively charged phosphate backbone of the molecule. Consequently, the dyes used to label, for the example, the termini of an oligonucleotide with a substantially random coil shape are not expected to interact with one-another and should not be expected to demonstrate fluorescence signal quenching. Therefore, based on what is widely known about protein labeling and oligonucleotide structure, one would have expected that oligonucleotides of various embodiments of the present invention would exhibit too little fluorescence quenching to be useful in detecting the presence of or level of oligonucleotide in a given sample. Based on what is taught in the art it was expected that the background fluorescence of these molecules would be so high that they could not be used to monitor real-time PCR. Indeed, researchers have gone to great length to design elaborate oligo structures that position labeling fluorophores so as to facilitate fluorophore aggregation to quench fluorescence. For example, both U.S. Pat. Nos. 6,150,097 and 6,037,137 mentioned the possibility of designing a real-time PCR probe based on Molecular Beacon structure that brings two reporter fluorophores into physical contact with one another.

Another unexpected observation gleaned from using one embodiment of the present invention is that oligonucleotide secondary structure that promotes dye aggregation is both unnecessary and undesirable. We observed that aggregation of identical reporter dyes is not only unnecessary, but in many instances detrimental to the performance of real-time PCR probes. Probes of one embodiment of the present invention, that have the simplest structure, are oftentimes much more sensitive than probes made in accordance with methods disclosed in much of the prior art. Additionally, probes that are designed to have complex internal secondary structure are generally more difficult to design and manufacture than are probes that are substantially devoid of internal secondary structure.

It has been widely reported that certain fluorescent or non-fluorescent dyes tend to form ground state complexes. These complexes are likely to form, in aqueous solvents at high concentrations or when the molecules are within close proximity to one another. Further discussion of this is provided by West et al., *J Phys Chem* (1965); Rohatgi et al., *J Phys Chem* (1966); Rohatgi et al., *Chem Phys Lett* (1971); and Khairutdinov et al., *J Phys Chem*. (1997).

The formation of either a homodimer between two identical dyes, or heterodimer between two different dyes leads to a distinct change in the absorption spectrum of the dyes. This is believed to be the result of coupling of the excited state energies of the dyes. A particular type of dimer called an H-dimer that forms between two fluorescent dyes or between a fluorescent dye and a non-fluorescent dye is characterized by a blue shift in the absorption maximum of the dyes and fluorescence quenching. Fluorescence quenching due to H-dimer formation has been exploited to construct fluorogenic peptidase substrates. Further discussion of this subject is provided by Packard et al., *Proc. Natl. Acad. Sci.* (1996); Geoghegan et al., *Bioconjugate Chem* (2000); Tyagi et al., *Nat. Biotechno.* (1998); Bernacchi et al., *Nucleic Acids Res.* (2001); Marras et al., *Nucleic Acids Res.* (2002); Johansson et al, *J. Am. Chem. Soc.* (2002); U.S. Pat. No. 6,037,1376 and 150,097.

In all of the aforementioned references, the labeled peptides or oligonucleotides are constructed in a manner designed to ensure that the molecules are physically close enough to one another so that signal from the donor dye is quenched prior to enzymatic cleavage. This is apparently the case with peptidase substrates, and with molecular beacon probes before they hybridize to their target sequences. For example, the fluorogenic peptides disclosed in U.S. Pat. No. 6,037,137, require so-called, "conformation determining regions" that introduce bends into the peptides so that the dye pair are held in close proximity for efficient "contact fluorescence quenching". Similarly, U.S. Pat. Nos. 6,150,097 and 6,037,137 disclose molecular beacons having a fluorescent reporter dye attached to one terminal and a quencher dye attached to the other terminal. Alternatively these probes have one reporter dye attached to one terminal and an identical reporter dye attached to the other terminal, wherein the dye pair is in physical contact to effect fluorescence quenching. In a variation of this method one group reportedly achieved contact quenching by labeling a linear oligonucleotide with a fluorophore and a highly hydrophobic quencher that favors formation of a heterodimer with the fluorophore. See Johansson, et al, *J. Am. Chem. Soc.* (2002).

In contrast to these approaches, oligonucleotide probes of some embodiments of the present invention are substantially devoid of clearly definable secondary structure or other conformation determining structures that result in the probes assuming a particular rigid conformation. Furthermore, it is not necessary to form a dimer or other structures that facilitate physical "touching" between the dyes in the probes of many embodiments of the present invention comprising two or more fluorescent reporter dyes.

The absence of proximal quenching between the dye pair of various embodiments is demonstrated by a lack of significant alteration in the absorption profile of the doubly labeled probe before and after enzymatic digestion. See, for example, Traces 29 vs. 28 in FIG. 4A and further discussion in Example 5. The small overall wavelength shift from Trace 28 to Trace 29, is different from a change in the shape or profile of the spectrum, and is caused by a difference in the micro environment that the dye experiences. This is referred to as the "solvent effect". The solvent effect is confirmed by the nearly superimposable spectra of the probe doubly labeled with CR110 (Trace 29) and another oligonucleotide of the same sequence labeled with a single CR110 at either 5' (Trace 31 in FIG. 4B) or at 3' (Trace 33 in FIG. 4C). In this instance the dyes experience a similar solvent effect. Once again, the similarity in the absorption spectra between the doubly labeled probe and the two singly labeled oligonucleotides indicates that there is substantially no dye aggregation in the doubly labeled probe.

To illustrate the spectral change upon dimer formation, we synthesized three molecular beacon probes with loop sequences that are identical to that of the linear probe. One beacon probe was labeled with two 5-CR110 dyes at the 3' and 5' terminals (SEQ ID No 12), another beacon probes was labeled with two 5-TAMRA dyes at the 3' and 5' termini (SEQ ID No 13). And still another beacon probe was labeled with two 5-ROX dyes at the 3' and 5' termini (SEQ ID No 14). As shown in FIGS. 5A, 5B and 5C and further detailed in Example 7. The absorption spectra of all beacon probes (Trace 38, 40, and 42) have been altered significantly from those of linear probes (Traces 37, 39, and 41), with each forming a new shorter wavelength peak characteristic of H-dimer formation. For a more thorough discussion of this please see Blackman et al., *Biochemistry* (2002); Packard et al., *Proc. Natl. Acad. Sci.* (1996). Upon S1 nuclease digestion, the spectra changed back to that of free dye. Although the fluorescence of beacon probe labeled with two reporter dyes is well quenched as a result of dye dimer formation, the probe has relatively low sensitivity for nucleic acid detection. FIGS. 6A, 6B, and 6C compares the kinetic fluorescence measurements between the molecular beacons and the linear probe each labeled with two identical dyes of 5-CR110, 5-TAMRA, 5-ROX, respectively according to various embodiments of the present invention.

As the data indicate, the probes made according to various embodiments of the present invention are often times 2-10 times more sensitive than the corresponding beacon probes. The significantly weaker sensitivity of the beacon probes may be explained in terms of competing equilibria that exist during the PCR detection process. As illustrated in FIG. 7, (details in Example 8), there are three competing equilibria these are between: 1) single stranded target DNA and double stranded target DNA ($K_A$); 2) beacon in the open conformation and beacon in the closed conformation ($K_B$); and 3) the probe-target hybridization product and the two reactants, single stranded target DNA and beacon in random conformation ($K_C$).

Formation of the probe-target hybrid separates the two dyes, and as a result, fluorescent signal is generated. Clearly, the higher the concentrations of the single stranded target DNA and greater the amount of probe in the random coil conformation, the more the equilibrium $K_c$ will shift toward the formation of the probe-target hybrid product, thereby increasing the fluorescent signal. However, at a given PCR cycle number and therefore at a given concentration of the single stranded target DNA, the amount of hybrid formation is proportional to the concentration of the probe in random conformation, which is in equilibrium with the beacon in the closed conformation. Therefore, the very existence of the closed beacon conformation reduces the concentration of the probe in random conformation that can form the hybrid product and this reduces the strength of the fluorescent signal. Additionally, juxtaposing a pair of dyes at the probe terminals to form a dimer is likely to increase the melting temperature of the stem-loop structure, further stabilizing the closed conformation and making formation of the fluorescent probe-target hybrid even more unfavorable. The fluorescent signal of a beacon probe can be improved if an enzyme with 5'-exonuclease activity is used in the reaction; following probe-target hybrid formation, 5'-exonuclease cleaves the probe and generates irreversibly stable fluorescent signal. Still, the equilibrium between the closed and random conformations of the beacon slows down the rate at which the fluorescent product is formed. Within the time frame of each PCR cycle, typically 10-30 seconds, only a fraction of thermodynamically allowable amount of cleaved product is formed, resulting in a relatively weak signal as shown in FIGS. 6A, 6B and 6C (details in Example 8). On the other hand, homo-doubly labeled probes according to various embodiments of the present invention stay in an open random conformation, and therefore can readily form fluorescent probe-target hybrids. Cleavage of the hybridized probe by 5'-exonuclease further enhances the signal because it produces an irreversibly de-quenched stable fluorescent product.

A major distinction between probes of some of the embodiments of the present invention and probes such as the TaqMan probe is that probes of many embodiments of the present invention have two or more reporter dyes while TaqMan probes have only a single reporter dye and a single quencher. Although the quencher itself can also be a fluorescent dye, such as TAMRA in the FAM/TAMRA donor/quencher pair, only the emission of the donor dye FAM is detected and only its fluorescence signal is correlated to the amount of DNA produced. In TaqMan assays the fluorescence of the quencher is either ignored or not even detected. Real-time PCR detection using TaqMan probes relies upon FRET-based fluorescence quenching of the donor fluorophore to lower the background signal in the assay. Prior to hybridization to a target DNA and/or hydrolytic cleavage of the probe by 5-exonuclease activities, the fluorescence of the donor is quenched and thus no signal or very weak signal is detected. Following probe hybridization and/or enzymatic cleavage of the probe, the fluorescence of the donor is released and thus a positive signal corresponding to an increase to the amount of DNA produced is detected.

Because the maximum signal that can be generated using a TaqMan is produced by a single donor molecule the net signal gain, (the ultimate performance) of a TaqMan probe is largely determined by the efficiency of fluorescence quenching before and the fluorescence yield of the fluorophore after probe cleavage. Therefore, ideally in the TaqMan assay, the quencher should completely quench the fluorescence of the donor until the reporter is cleaved from the oligonucleotide. Complete quenching is usually required to ensure that the real-time PCR assay starts with a dark background. As discussed earlier, in accordance with to the well-known principles of FRET, the efficiency of FRET-based quenching is positively related to the overlap of the emission spectrum of the donor molecule and absorption spectrum of the acceptor (quencher) molecule. For a more thorough discussion of FRET the reader is directed to references such as Förster, *Ann. Phys.* (1948); Stryer et al., and *Proc. Natl. Acad. Sci.* (1967).

Furthermore considering that the fluorescence emission wavelength of a dye is always longer than its absorption wavelength (as defined by its Stokes shift) the best quencher molecule for a given dye molecule will necessarily be a different dye. This is so because the absorption spectra of the quencher must match with the emission spectra of the donor. In fact, the larger the Stokes shift of the donor dye is, the better the donor dye is because the donor can then be excited at its absorption maximum without having it interfere with its emission. This is the rationale for a second method used to increase signal output. Given the principles of FRET-based quenching, the advantage of having a donor dye with a large Stokes shift, and the need to have maximal FRET-based quenching, one would have necessarily choose a quencher with an emission wavelength substantially different the emission wavelength of the donor dye.

In sum based on the basic principles of FRET and its wide spread use in the construction of oligonucleotide including primers and probes the current art appears to teach away from various embodiments of the present invention.

Accordingly, the embodiments of the invention are nonobvious in view of the cited art as illustrated by the results obtained with probes that were either homo-doubly labeled with FAM or sulfonated Cy5. FAM and Cy5 are two of the most widely used reporter dyes. However, neither of these dyes produced homo-doubly labeled probes, which exhibited significant signal changes, and low background fluorescence (Data not shown). In practice, in order to increase the sensitivity of TaqMan probes, most commercial effort has been focused on the development of more efficient quenchers particularly quenchers based on non-fluorescent dyes. Examples of highly efficient commercially available non-fluorescent quenchers include azo dye-based BHQ quenchers from Bio-Search, Inc., polynitro cyanine dyes from Amersham, Inc. and the rhodamine-based YSQ dyes from Molecular Probes.

Probes labeled with two reporter dyes according to various embodiments do not have to be designed so as to position the dye molecules in close physical proximity to one another. However, aggregation is more likely to occur among probes that are labeled with multiple dye molecules and optional quencher molecules than among the same oligonucleotide sequences labeled with a single reporter and quencher molecule. Accordingly, at least some of the oligonucleotides, labeled with at least two signaling dyes (and optionally with one or more quencher molecules) according to various embodiments of the invention may exhibit low background fluorescence and high signal output upon permanent separation of the dyes as result of the probe cleavage, because of the large number of signaling molecules per oligonucleotide.

Preferably, in some embodiments, oligonucleotides are labeled with a plurality of spectrally identical or similar fluorescent dyes. A mixture of fluorescent reporter dyes may be used for labeling a particular probe as long as the dyes have similar absorption or excitation spectra so that they can all be efficiently excited with a single excitation light. For example, a probe of the present invention may comprise both Cy3 (Glen Research, Sterling, Va.) and TAMRA (Biotium, Inc. Hayward, Calif.), both of which have similar spectra and can be efficiently excited at 540 nm. As another example, a particular probe may comprise both CR110, and FAM, both of which also have similar spectra and can be well excited by the 488 nm argon laser line. Although probes labeled with mixed dyes are relatively more difficult to synthesize, in certain cases it can be advantageous if such mixed dyes promote fluorescence quenching prior to hybridization with a target sequence. For example, a probe of the present invention can be labeled with a mixture of one dye with a net negative charge and another dye of similar spectrum but with a net positive charge. A mixture of dyes with opposite charges may promote fluorescence quenching. Methods of adding charges to dyes are well known to anyone skilled in the art. For example, negative charges can be added to dyes by sulfonation, while positive charges can be created on dyes by adding secondary, tertiary, or quaternized amines to dyes. For a more thorough discussion of these molecules the reader is directed to see Mujumdar et al., 1993, *Bioconjugate Chem.*

More preferably, probes of some embodiments of the present invention are oligonucleotides labeled with a plurality of identical fluorescent dye molecules. Oligonucleotide probes thereof have the advantage of being easily and economically manufactured because dyes can be conjugated to the oligonucleotide in a single step. Extensive research efforts were made in the 80's to develop efficient techniques for labeling nucleic acids. These techniques have been well documented. For a more thorough discussion of this subject the reader is directed to the following references: Connolly et al., *Nucleic Acids Res.* (1985); Dreyer et al., *Proc. Natl. Acad. Sci.* (1985); Nelson et al., *Nucleic Acids Res.* (1989); Sproat et al., *Nucleic Acids Res.* (1987) and Zuckerman et al., *Nucleic Acids Res.* (1987).

Probes of existing technologies having a reporter/quencher dye pair require separate labeling steps and expensive reagents. For example, the first label, dye or quencher, is typically attached to an oligonucleotide, either by starting the oligonucleotide synthesis with a protected dye linked to a CPG solid support, or by incorporating the dye during the oligonucleotide synthesis by using a dye-labeled nucleoside (or 2'-deoxynucleoside) phosphoramidite. The second quencher or dye molecule is attached to the oligonucleotide by using a dye- or quencher-labeled nucleoside phosphoramidite during the standard oligo synthesis. Alternatively and more typically, the second dye or quencher molecules is attached to the oligo by first incorporating an amino group into the oligo during the oligo synthesis and then reacting a succinimidyl ester dye or quencher with the amine-modified oligo. In contrast to this multi-step labeling procedure, probes of one embodiment of the present invention comprising multiple identical dyes. Labeling with a single dye requires only a single dye-labeling step, typically by mixing in a buffer for 1~2 hours a reactive form of the dye with an oligonucleotide containing a desired number of a reactive groups capable of reacting with the dye. Typically, reactive groups are first incorporated into an oligonucleotide via standard phosphoramidite chemistry using commercially available reagents.

Most preferably, probes of some embodiments of the present invention are oligonucleotides labeled with two identical fluorescent dyes whose fluorescence is quenched without formation of dye aggregates. And preferably, the dyes are attached to the 3'- and 5'-terminals of the oligonucleotides, respectively. In one embodiment of the invention, one dye is attached to the 3' terminal backbone phosphate via a flexible aliphatic linker, and another identical dye attached to the 5' terminal backbone phosphate via another flexible aliphatic linker. The flexible linkers are C2 to C30 linear or branched, saturated or unsaturated hydrocarbon chains, optionally substituted by heteroatoms, aryls, lower alkyls, lower hydroxylalkyls and lower alkoxys. Preferably, the linkers are C4 to C12 linear or branched, saturated hydrocarbon chains optionally substituted by heteroatoms, lower alkyls and lower hydroxylalkyls.

In another embodiment of invention, probes labeled with a plurality of reporter dyes and quenchers further comprise a nucleic acid binding group. Examples of nucleic acid binding groups include minor grove binders (MGB), nucleic acid interculators, and polyamines. In cases in which an nucleic acid binding group is incorporating into probes of various embodiments of the present invention, the oligonucleotide sequence of the probes can be me made shorter and still produce a useful signal. Shorter probes translate into lowering manufacturing costs. Methods of incorporating a nucleic acid binding group into an oligonucleotide probe or primer have been well documented see, for example, U.S. Pats. Nos. 5,801,155; 6,472,153; 6,486,308; 6,492,346 and numerous publications such as Afonina et al, *N. A. R.* (1997); Kumar, et al., *N. A. R.* (1998) and Kutyavin, et al, *N. A. R.* (2000). Preferably, the nucleic acid binding group is a minor grove binder (MGB). And preferably, probes comprising a nucleic acid binding group are labeled with two or more identical reporter dyes. More preferably, probes comprising a nucleic acid binding group are labeled with two identical dyes that may or may not physically touch each other.

In still another embodiment of the invention, oligonucleotide probes comprise a plurality of fluorescent reporter dyes, in which at least some of the reporter dyes are attached to a G nucleotide or near to a G nucleotide located within the labeled oligonucleotide. In this arrangement the fluorescence of the dye or dye molecules nearest to the G nucleotides are quenched before the oligo hybridizes to its complementary sequence.

In one embodiment of the invention, the primer is a single stranded linear oligonucleotide comprising a plurality of spectrally identical or similar fluorescent reporter dyes. In the absence of a target sequence, said primer assumes a random coiled conformation and is non-fluorescent or weakly fluorescent. An oligonucleotide primer in the random coiled conformation is substantially devoid of internal secondary structure. Oligonucleotides substantially devoid of internal secondary structure do not readily from secondary structures such as of stem-loops, hairpins and the like.

Once primers labeled with photometric molecules such as fluorescent molecules are incorporated into the amplification product the fluorophores are further separated from each other due to the more extended conformation of the amplification product and therefore the fluorescence signal from the photometric molecule increases. When a primer is made in accordance with the embodiments of the present invention the primer includes at least two fluorophores per primer. Accordingly, primers made in accordance with the present invention can be used to assay for complimentary oligonucleotides with greater sensitivity than assays that use primers labeled with only a single signaling molecule.

Upon hybridization with a target sequence and subsequent incorporation into the amplification product, the fluorescence of some of the primers made in accordance with embodiments of the present invention increases. Accordingly, one advantage of primers of some embodiments of the present invention is that multiple dye molecules present on the oligos produce signal when they hybridize to their targets. As there are at least two signaling molecules per oligonucleotide the signal they produce is greater than the signal produced by a primer that has only a single dye molecule attached to it. This helps to make some of the primer made in accordance with the methods of the present invention more sensitive nucleic acid detectors than primers of existing technologies that include only a single signaling molecule.

The dye molecules are typically attached to the bases of nucleotides or to a combination of the 5' terminal backbone phosphate and the bases of an oligonucleotide via an aliphatic linker. The dye attachment sites are spaced in a manner to achieve maximal fluorescence quenching before hybridization and maximal fluorescence following hybridization and incorporation into the amplification product. Typically, the optimal spacing between any two adjacent pair of fluorescently labeled nucleotides or between the 5' terminal and an adjacent fluorescently labeled nucleotide is 10 to 50 nucleotides; Preferably, the spacing is about 15 to 30 nucleotides; Most preferably, the spacing is about 15 to 25 nucleotides.

In one embodiment is a primer labeled with two spectrally identical or similar fluorescent dyes. Typically, one dye is attached at or near the 5' ends via a linker and another dye attached at or near the 3' ends via another linker. Preferably, one dye is attached to the 5' terminal backbone phosphate via a linker and, with proper spacing, another dye to the base of a nucleotide, such as a T via another linker. Typically, linker molecules are C2 to C12 linear or branched, saturated hydrocarbon chains optionally substituted by heteroatoms, aryls, lower alkyls and lower hydroxylalkyls. The two dye molecules may be separated by about 15 to about 25 bases.

In one embodiment, the primer is a linear oligonucleotide labeled with two identical dyes with one dye attached to the 5' terminal backbone phosphate via a linker and another dye attached to the base of a nucleotide T at or near the 3' end via another linker. Said linkers are C4 to C12 linear or branched saturated hydrocarbon chains optionally substituted by heteroatoms, lower alkyls and lower hydroxylalkyls. Fluorogenic primers labeled with two identical dyes according to the present invention are significantly easier to manufacture than primers of existing technologies. This is especially true when a donor dye and a quencher molecule need to be attached in separate steps using expensive reagents, or wherein a long, low-yielding nucleotide needs to be synthesized to form a required hairpin structure.

Similarly, primers made in accordance with various embodiments of the present invention are less expensive to manufacture than primers made by many of the currently used methods. In contrast to the multi-step labeling procedure required to synthesize primers that include labeling molecules with different chemistries, primers comprising two identical dyes require only a single dye-labeling step. Typically labeled oligonucleotides of various embodiments of the present invention can be made by mixing a reactive form of the dye with a primer containing two reactive groups capable of reacting with the dye in a suitable buffer for 1~2 hours. Reactive groups are first incorporated into the oligo via standard phosphoramidite chemistry using commercially available reagents.

A major advantage of the fluorogenic oligonucleotides according to various embodiments of the present invention is the freedom to use fluorescent dyes of virtually any class and any wavelengths without having to match up a report dye with a particular quencher. This may be so because some embodiments appear not to rely on classic FRET-based fluorescence quenching to produce an assay with a useable signal. Examples of suitable classes of fluorescent dyes useful in the present invention include, but are not limited to, coumarins, xanthene dyes, cyanines, pyrenes, styryl dyes, BODIPY dyes, stilbenes and derivatives thereof; the widely used rhodamines, fluoresceins and rhodols belong to the class of xanthene dyes. Preferable dyes include neutral dye molecules and dye molecules that have a delocalized positive or negative charge. Neutral dyes are dyes that do not bear any charge or dyes that bear an equal number of positive charges and negative charges, neutral dyes of latter type are also referred to as zwiterionic dyes. Examples of neutral dyes include, but are not limited to, BODIPY dyes, rhodamines, zwiterionic cyanine dyes, and derivatives thereof as shown in the following representative structures:

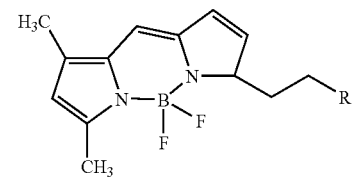

BODIPY

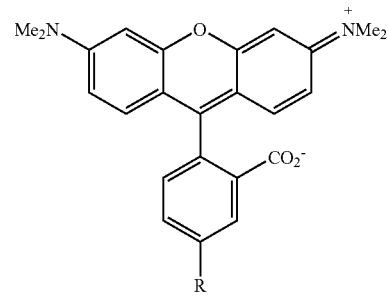

Tetramethylrhodamine

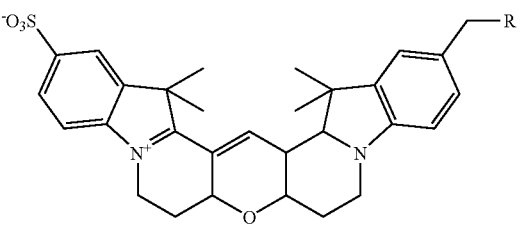

Cy3B wherein R is a reactive group.

Examples of dyes having a delocalized positive charge include, but are not limited to, rosamines, cyanines, and derivatives thereof as shown in the following representative structures:

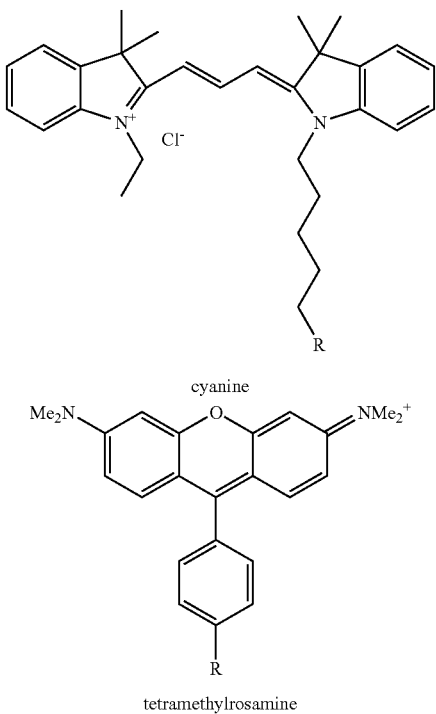

cyanine tetramethylrosamine wherein R is a reactive group.

Examples of dyes having a delocalized negative charge include, but are not limited to, fluorescein and resorufin derivatives as in the following representative structures:

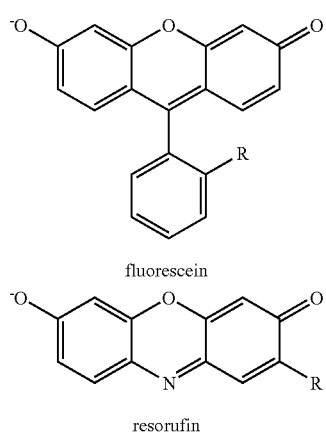

fluorescein resorufin wherein R is a reactive group.

Alternatively, oligonucleotides of some embodiments are labeled with a combination of negatively charges dyes and positively charged dyes wherein the numbers of negatively charged dyes and positively charged dyes are in proximately 1:1 ratio. Examples of negatively charged dyes include fluorescein derivatives and sulfonated dyes such as those described in U.S. Pat. Nos. 5,696,157; 6,130,101; 5,268,486; and 6,133,445, and in U.S. patent applications UA2002006479A1 and UA20020077487A1. Examples of positively charged dyes include the abovementioned rosamine dyes and cyanine dyes as well as dyes modified with a tertiary or quaternary amines using standard chemistry.

In another embodiment of the present invention, suitable dyes for synthesizing said oligonucleotides include energy transfer dyes such as those described in U.S. Pat. Nos. 5,800,996; 6,479,303B1; and 6,545,164B1 as well as International Publication WO 00/13026. Combinations of probes or primers labeled with different energy transfer dyes and non-energy transfer dyes can be used for multiplex detection in a single closed tube.

Suitable dyes include for use in various embodiments include, but are not limited to, rhodamine xanthene dyes having the following structure:

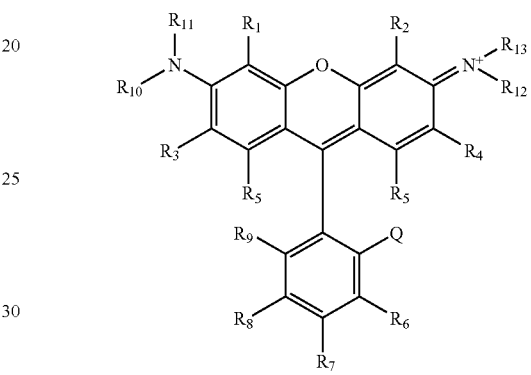

wherein $R_1$, $R_2$, $R_3$, and $R_4$ are independently H, F, Cl, C1-C18 alkyl or C2-C18 alkenyl groups; $R_5$ is H; $R_{10}$, $R_{11}$, $R_{12}$, and $R_{13}$ are independently H, C1-C18 alkyl groups, or C2 to C18 alkenyl groups optionally substituted with a reactive group; said structure further includes between 0 and 4 additional saturated or unsaturated 5 or 6 membered rings selected from the group of rings consisting of rings that include; $R_1$ in combination with $R_{11}$, $R_2$ in combination with $R_{13}$, $R_3$ in combination with $R_{10}$, and $R_4$; each said additional ring may be substituted with one or more lower alkyl groups; Q is $CO_2^-$, or $SO_3^-$, or a reactive group; $R_7$ and $R_8$ are independently H, F Cl, or a reactive group; and $R_6$ and $R_9$ are independently H, F, or Cl. Suitable reactive groups for attaching these and other dyes and quenchers to oligonucleotides include, but are not limited to electrophiles and nucleophiles as listed in Table 2 and other groups listed in the definitions section. Other means for attaching photometric molecules and quenchers include aliphatic linker groups.

Still other dyes for use in various embodiments include but are not limited to cyanine dyes with the following structure:

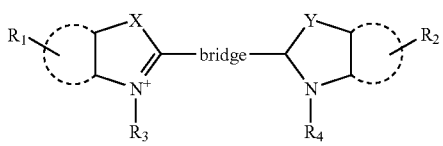

wherein, $R_1$ and $R_2$ are independently selected from the groups consisting of H, F, Cl, Br, CN, carboxylic acid group, carboxamide, sulfonate, sulfonamide, lower alkyl groups, or at least one additional fused aromatic rings, said additional fused rings include atoms independently selected from the group consisting of: C, N, O and S, a reactive group, and lower alkoxy groups substituted with H or a reactive group; $R_3$ and $R_4$ are independently lower alkyl groups substituted with either H or a reactive group; X and Y are independently selected from the group consisting of: O, S, $NR_5$ and $CR_6R_7$; $R_5$, $R_6$, and $R_7$ wherein $R_5$, $R_6$, and $R_7$, $R_5$ are independently H, C1 to C18 alkyl groups; and "bridge" is either a methane or polymethine group. Reactive groups suitable for attaching the molecule to an oligonucleotide include but are not limited to the nucleophilic and electrophilic groups listed in Table 2 and other groups listed in the definitions section. In addition to various reactive groups, suitable dyes and quenching molecules may also be attached to oligonucleotides by for example aliphatic linkers.

Alternatively, suitable dyes are energy transfer dyes wherein one of the dye pair is a rhodamine dye or cyanine dye.

EXAMPLES

Example 1

Oligonucleotide Synthesis and Labeling

Materials and Equipment

All anhydrous solvents and phosphoramidite reagents including phosphoramidites of nucleosides and protected linkers were purchased from Proligo, Boulder, Colo. or Glen Research, Sterling, Va. All unlabeled and amine-modified oligonucleotides were synthesized on an Expedite 8909 oligo synthesizer by Applied Biosciences (Foster City, Calif.).

Synthesis of Unlabeled Oligonucleotides

All unlabeled oligonucleotides (primers) were synthesized by starting with a protected nucleoside on CPG support with a glass bead pore size of 500 Å. Deprotection, coupling and oxidation steps were all carried out by following standard protocols provided by the manufacturers. Cleavage of oligonucleotides from CPG support and deprotections were carried out by incubating the CPG beads in ammonium hydroxide at 55° C. for 16-18 hours. Once removed from the solid support, the oligonucleotides were concentrated down via a SpeedVac to remove the excess ammonia, and then purified by passing the crude products through a Sephadex G-25 column or a C18 reverse phase cartridge. Final purifications, if necessary, were carried out with HPLC (See Purification below).

Synthesis of Amine-Modified Oligonucleotides

Amine-modified oligonucleotides were synthesized by using a CPG-supported amino modifier and appropriate phosphoramidite reagents containing a protected amine during the normal automated oligo synthesis.

A variety of commercially available CPG-supported amino-modifiers with different spacer arms can be used. These products allow one to introduce an amino group at the 3' end. The CPG-supported amino modifier, 3'-amino-modifier C7 CPG, was used in some of the examples listed in Table 1 and it has the following structure:

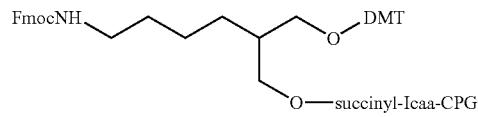

(with $L_1$ spacer)

wherein, Fmoc and DMT are protection groups for the amine and hydroxy groups, respectively, and "succinyl-Icaa" is a spacer between the solid support and the modifier. The base-labile Fmoc group was removed during ammonium treatment to remove oligos from CPG support. The reagent introduces a 7-carbon branched spacer between the amine group and the 3'-end phosphate. For reference purpose, we refer to this spacer as $L_1$. One skilled in the art can appreciate that there are many other forms of modifier reagents on a solid support that can be used to introduce an amine with a different spacer, or to introduce a different reactive group other than an amine.

Amine-containing phosphoramidite reagents include phosphoramidites of protected amino-deoxynucleosides and protected amino-modifiers. The most widely used and also least expensive phosphoramidites of protected amino-deoxynucleosides is phosphoramidite of trifluoroacetylamino-2'-deoxythymidine, or amino-modifier C6 dT, which was used for making T-modified oligonucleotides in some of the examples given Table 1. Shown below is the structure of amino-modifier C6 dT:

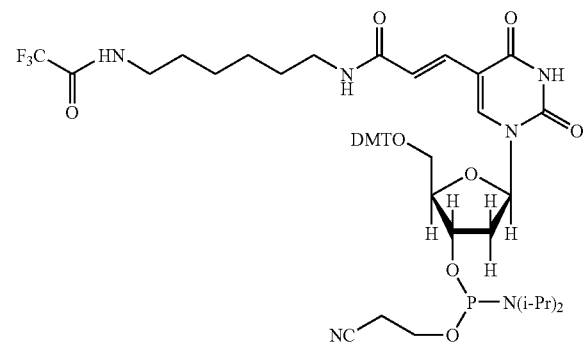

(with $L_2$ spacer)

This reagent introduces a 10-atom linear aliphatic spacer between dT and the amine group, or between dT and a dye. For reference purpose, we refer to the 10-atom spacer as $L_2$.

Alternatively, an amine can be introduced to the 5'-end by using a phosphoramidite of a protected amine at the last step of the automated synthesis. Two amino modifier reagents, 5'-amino-modifier C6-TFA and 5'-amino-modifier C12, were used for synthesizing 5'-end labeled oligonucleotides shown in this disclosure. The structures are shown below:

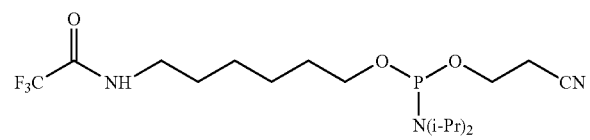

(with $L_3$ spacer)

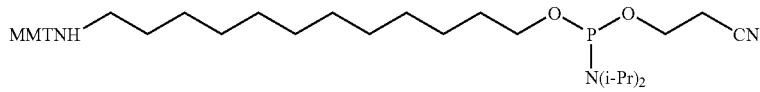

(with L₄ spacer)

For reference purpose, the linear 6-carbon spacer of 5'-amino-modifier C6-TFA is referred to as $L_3$, and similarly the linear 12-carbon spacer of 5'-amino-modifier C12 is referred to as $L_4$.

There are many other forms of modifier reagents that can be used to introduce an amine with a different spacer, or to introduce a different reactive group other than an amine.

Synthesis of Dye-Labeled Oligonucleotides

Labeling reactions were conducted by adding a solution of a succinimidyl ester dye (Biotium, Inc., Hayward, Calif.) in DMF at ~40 mg/mL to an amino oligo dissolved in 0.1 M NaHCO₃ (pH 8.5) at ~1 mg/mL and vortexing the solution at room temperature for ~2 h. The molar ratio of dye NHS ester to each amino group in the oligo was about 20-40 to 1. Unreacted dye was effectively removed by a Sephadex G-25 spin column. The crude products thus obtained were subject to further purification by HPLC (See below).

Purification of Labeled Oligonucleotides

Labeled oligonucleotides were purified by reverse phase HPLC on a Hitachi D7000 HPLC System.

Typical HPLC condition:

Column: C18 YMC ODS-A 5 um 12 nm 150×4.6 mm, or C18 Microsorb 5 um 30 nm 200×4.6.

Column temperature: 45° C.

Gradient: 10% B to 50% B in 20 min-30 min@ 1 ml/min. A: 100 mM TEAA PH7.0; B: 100% CH₃CN.

Determination of Degree of Labeling

The absorbance from 230 nm to 700 nm of purified dye labeled oligonucleotides was measured on a spectrophotometer, whereby $\lambda_{max}$ for the dye ($A_{max}$) and $A_{260}$ were determined. The concentration of the dye was determined by measuring $A_{max}$ values, while the oligonucleotide concentration was calculated based on $A_{260}$ after factoring in the absorbance of the dye at 260 nm. The ratio of dye to oligo concentrations defines the degree of labeling (DOL). In our experiments, DOL for single label is close to one (e.g. FIGS. 4B & 4C) and that for doubly labeling is close to two (e.g. FIG. 4A). Based on this calculation we conclude that the doubly or singly labeled probes or primers detailed in current invention are generally over 90 to 95% pure.

Example 2

Monitoring of MCG Gene Amplification Using Doubly Labeled Probes

Figure 2A:
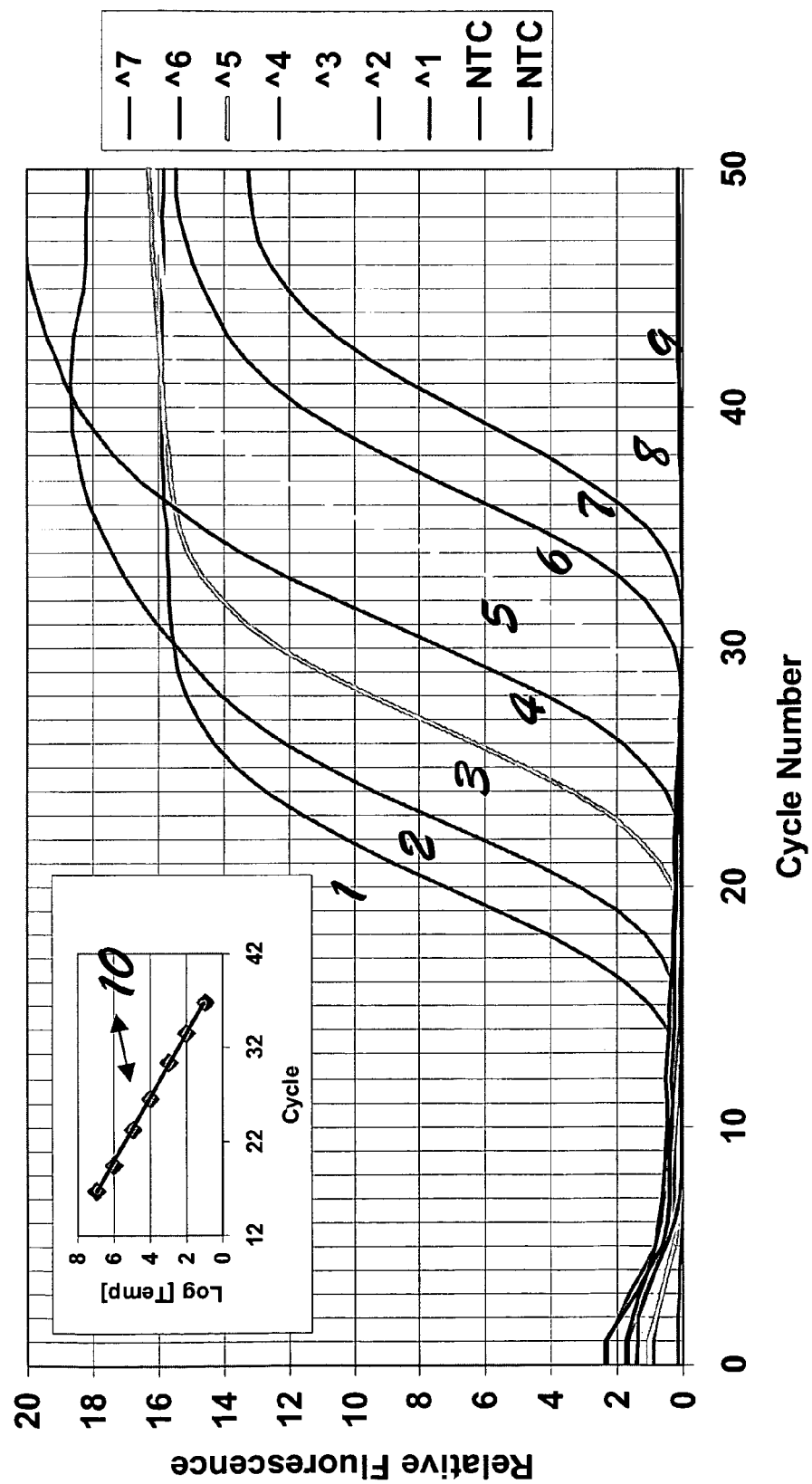
FIG. 2A shows plots of data collected when the MCG gene was amplified using PCR. These data were collected using a 6-ROX-labeled probe various at starting concentrations of plasmid DNA. (Example 2)

The first set of experiment in this example demonstrates the use of a doubly 6-ROX-labeled probe in RT-PCR detection of a MCG gene. The amplifications were performed in 20 μl reaction solution containing 10 mM Tris (pH 8.0), 50 mM KCl, 3.5 mM MgCl₂, 2 mM each of dNTP, and 1 unit of AmpliTaq Gold (ABI, Foster City, Calif.). A MCG gene fragment (SEQ ID 25) in pTOPO plasmid was amplified with 0.5 μM forward primer 5'-TCAAGAGGTGCCACGTCTCC-3' (SEQ ID No. 4), 0.5 μM reverse primer 5'-CTGATCTGTCT-CAGGACTCTGACACTGT-3' (SEQ ID No. 5). A doubly 6-ROX-labeled MCG probe, 5'-(6-ROX-L₃-CAGCACAACT ACGCAGCGCC TCC(-L₁-6-ROX)-3' (SEQ ID No. 6, see Table 1) was used for following the reaction. The thermal regimen was set at 95° C. for 7 minutes followed by 50 cycles of 15-second duration at 95° C. and 20 second duration at 60° C. Fluorescence was measured at the 60° C. step. A series of 10-fold dilutions of the template was made to create titration curves of the amplification plot. FIG. 2A shows amplification plots of aforementioned reactions starting with 10⁷ copies of template (Trace 1) down to 10¹ copies of template (Trace 7). Two NTC (no template control, Traces 8 and 9) are also shown in the figure. The insert shows that the Ct value is reversibly correlated with the logarithm of starting copy number (Trace 10).

In the second set of experiments the probe (SEQ ID No 36) was doubly labeled with non-sulfonated cyanine dyes and the experiment was carried out at two template concentrations, 100,000 copies (Trace 151) and 0 copy (Trace 152). All other reagents and conditions were the same as in the first set of experiments. This set demonstrates the use of a doubly cyanine-labeled probe in RT-PCR detection of the MCG gene.

Example 3

Figure 2B:
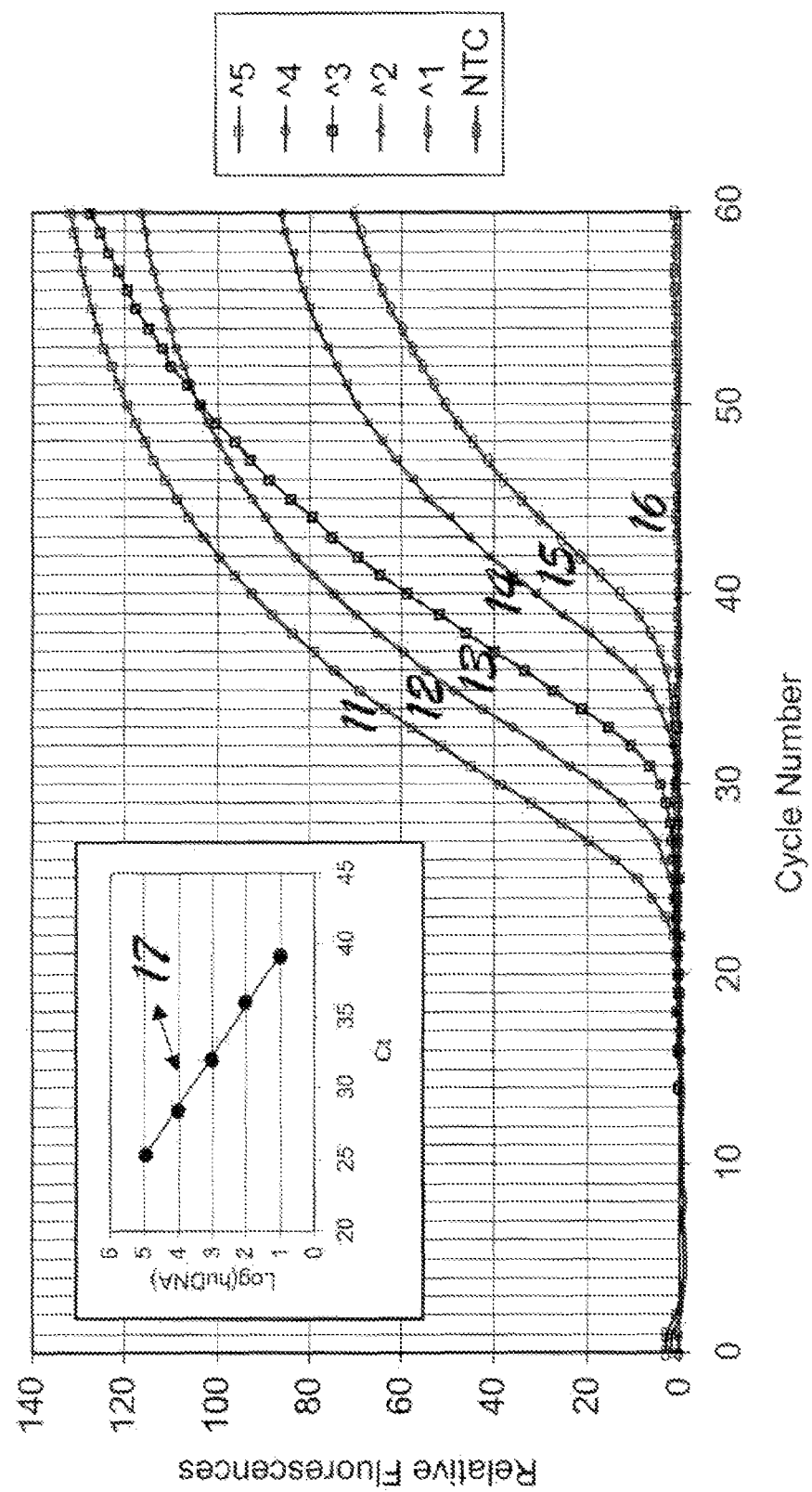
FIG. 2B shows plots of data collected when the MCG gene was amplified using PCR. These data were collected at various concentrations of human genomic DNA using a 6CR110-labeled probe. (Example 3)

Monitoring of MCG and GAPDH Gene Amplification Using a Probe Doubly Labeled with 6-CR110 from Complex Templates Amplifications of MCG gene fragment from human genomic DNA were performed as in Example 2 except (1) a 6-CR110 probe, 5'-(6CR110-L₃-)CAGCACAACT ACG-CAGCGCC TCC(-L₁-6-CR110)-3' (SEQ ID No. 7, see Table 1) and (2) a series of 10-fold dilutions of human DNA were used. FIG. 2B shows amplification plots of the reactions starting with 10⁵ copies of human DNA (Trace 11) down to 10¹ copies of human DNA (Trace 15). A NTC (Traces 16) is also shown in the figure. The insert shows that the Ct value is reversibly correlated with the logarithm of starting copy number (Trace 17).

Figure 2C:
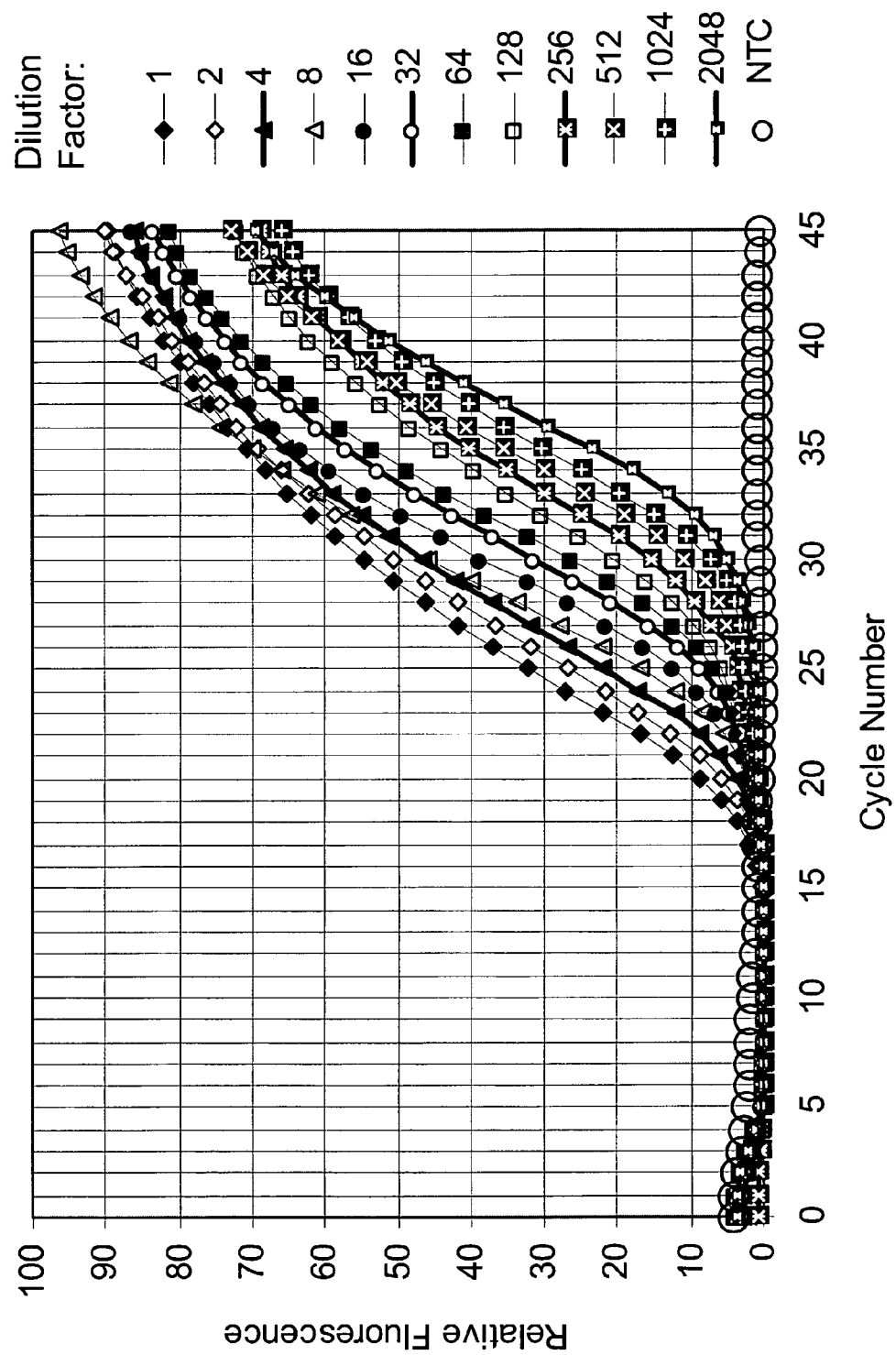
FIG. 2C shows plots of data collected with the MCG gene being amplified using PCR. These data were collected from various starting concentrations of human cDNA using a 6CR110-labeled probe. (Example 3)
Figure 2D:
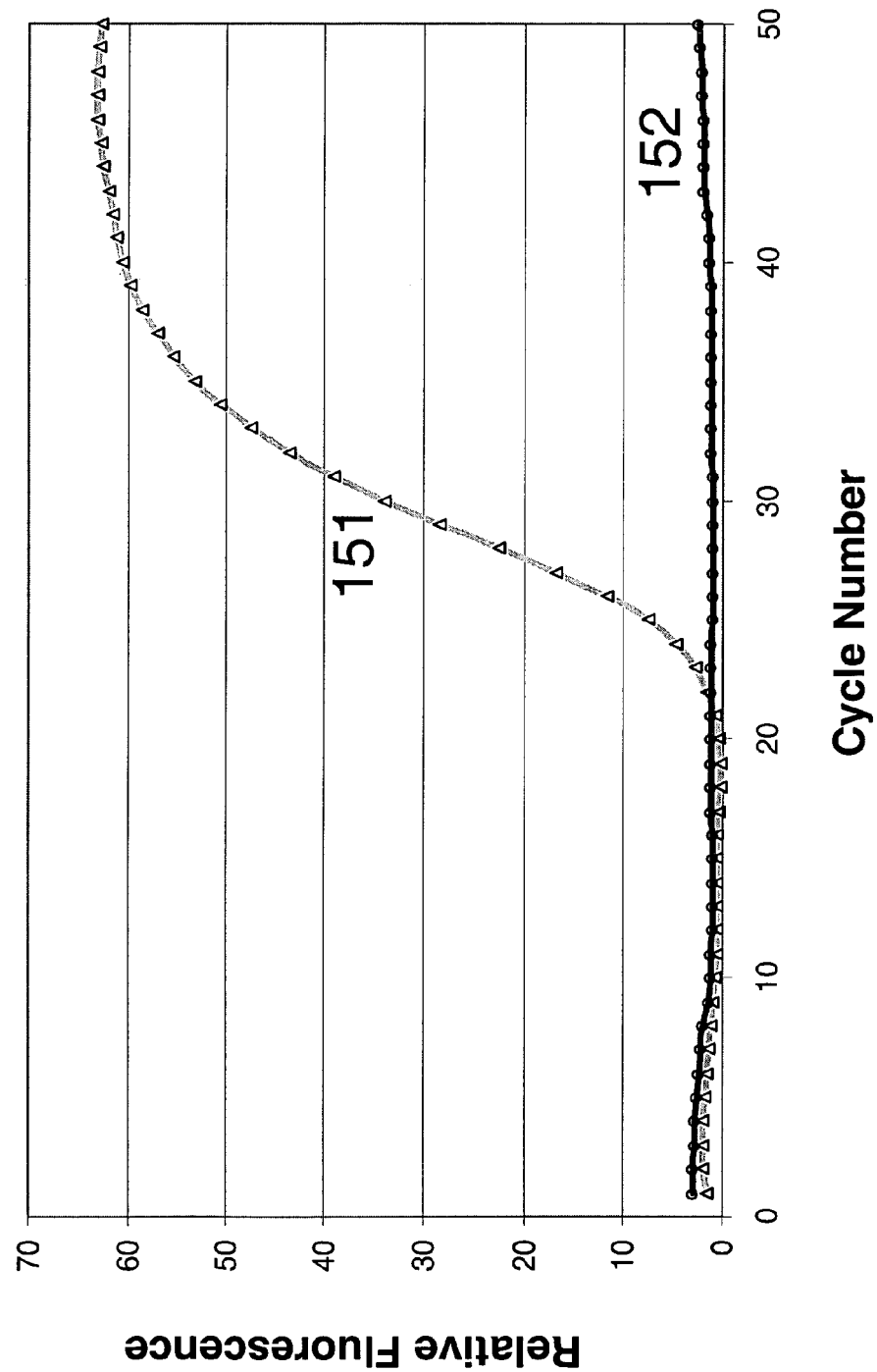
FIG. 2D shows the amplification plots of MCG gene amplified from 100,000 copies of plasmid DNA using a non-sulfonated cyanine-labeled probe. (Example 2)

Another titration (FIG. 2C) using cDNA as template was carried out as above except that GAPDH primers, 5'-GAAG-GTGAAGGTCGGAGTC-3' (SEQ ID No. 1) and 5'-GAA-GATGGTGATGGGATTTTC-3'(SEQ ID No. 2), and a GAPDH probe, 5'-(6CR110-L₃-)CAAGCTTCCCGTTCT-CAGC(-L₁-6-CR110)-3' (SEQ ID No. 21) were used. Starting with 0.2 μl of human brain cDNA (Invitrogen, Carlsbad, Calif.), a series of 2-fold dilutions were made. All PCR reactions were carried out in 10 μl volume. The thermal regimen was 95° C. (7-minutes), 45 cycles of 95° C. (15-second) and 56° C. (20-seconds).

Example 4

Comparison of a TaqMan Probe with a Doubly Labeled Probe of the Present Invention A GAPDH gene fragment was amplified from a PTOPO plasmid containing GAPDH gene fragment (SEQ ID No. 24, Table 1) with a forward primer, 5'-GAAGGTGAAGGTCG-GAGTC-3' (SEQ ID No. 1, Table 1) and a reverse primer, 5'-GAAGATGGTGATGGGATTTTC-3'(SEQ ID No. 2, Table 1). A TaqMan probe with JOE as the reporter dye and TAMRA as the quencher (5'-(6-JOE-$L_3$-)CAAGCTTC-CCGTTCTCAGC(-$L_1$-6-TAMRA)-3'; SEQ ID No. 8, See Table 1) or a probe according to the present invention doubly labeled with 5-R6G (5'-(5-R6G-$L_3$-)CAAGCTTCCCGT-TCTCAGC(-$L_1$-5-R6G)-3'; SEQ ID No. 9, See Table 1) was used for monitoring the reaction under reaction condition identical to that used in Example 2 except that the annealing/extension temperature was lowered to 56° C.

All amplification reactions were carried out with 1 million copies of the template, and concentrations of 125 nM, 250 nM and 500 nM were used for each probe, respectively. As shown in FIG. 3A, the signal strength of the probe made according to the present invention is twice as strong as that of the corresponding TaqMan probe (Trace 18 vs 21, Trace 19 vs 22 and Trace 20 vs. 23). R6G and JOE have comparable spectra as well as similar fluorescence quantum yield and extinction coefficient. Therefore, the observed performance difference between the two probes is not due to the dyes themselves but a reflection of the superior design of the probe according to the present invention.

A FAM labeled MCG TaqMan probe with FAM at the 5' end and TAMRA at 3' end was made and compared with doubly labeled CR110 probe (5'-(6CR110-$L_3$-) CAGCA-CAACT ACGCAGCGCC TCC (-$L_1$-6CR110)-3' (SEQ ID No. 7) with identical sequence in PCR. FIG. 3B shows the amplification plots of the said homo-doubly labeled CR110 probe with TaqMan probe of 1000 nM (Trace 115 vs Trace 119), 500 nM (Trace 116 vs Trace 120), 250 nM (Trace 117 vs Trace 121) and 125 nM (Trace 118 vs Trace 122) respectively. All amplifications start with one million copies of a plasmid containing MCG fragment. At saturated concentration (1000 nM), homo-doubly labeled probe outperformed said TaqMan probe in signal strength by 60%. Doubly labeled CR110 probe uses one half of TaqMan probe in concentration to get the same signal strength.

A FAM labeled cMyc TaqMan probe was currently provided by ABI in a 20× mixture of primer and probe. The probe has undisclosed sequence and comprised of a MGB at its 3' end. A comparison was made between said TaqMan probe with doubly labeled CR110 probe (5'-(6CR110-$L_3$-) CAG-CACAACT ACGCAGCGCC TCC (-$L_1$-6CR110)-3' (SEQ ID No. 7). FIG. 3C shows the amplification plots of the said TaqMan probe (Trace 110) and homo-doubly labeled CR110 probe of 1000 nM (Trace 111), 500 nM (Trace 112), 250 nM (Trace 113) and 125 nM (Trace 114). All amplifications used identical concentrations of human brain cDNA from Invitrogen. At saturated concentration (1000 nM), homo-doubly labeled probe outperformed said TaqMan probe in signal strength. Incorporation of MGB may further improve the performance of the probes in current invention.

Example 5

UV/Vis Absorption Spectra of Doubly Dye-Labeled and Singly Dye-Labeled Oligonucleotides and S1 Nuclease Digested Oligonucleotides Thereof The purpose of this experiment is to demonstrate that there is no physical touching between dyes in an oligonucleotide labeled with two reporter dyes according to the present invention. In order to demonstrate that the dyes need not touch one another we synthesized three CR110-labeled oligonucleotides of the same sequence: 1) a GAPDH probe doubly labeled at 3' and 5' (SEQ ID No. 3, Table 1); 2) a GAPDH probe sequence singly labeled at the 5' (SEQ ID No. 7, Table 1); and 3) a GAPDH probe sequence singly labeled at 3' (SEQ ID No. 8, Table 1). The two singly labeled oligonucleotides were made to serve as controls.

The spectra of the three labeled oligonucleotides in S1 buffer are shown in FIGS. 4A (trace 29), 4B (trace 31) and 4C (trace 33), respectively. To assess how the spectrum of the dye is also affected by the microenvironment surrounding the dye, the labeled oligonucleotides were digested by S1 and then spectra were taken (FIGS. 4A (Trace 28), 4B (Trace 30) and 4C (Trace 32)). Digestions were carried out by adding 20 units of S1 nuclease (Promega, Madison, Wis.) to a 100 μl reaction solution containing 250 to 500 nM probes in S1 buffer (50 mM sodium acetate (pH 4.5), 280 mM NaCl, and 4.5 mM $ZnSO_4$). S1 digestion was completed almost instantaneously after the S1 addition, as confirmed by following the UV/Vis absorption spectrum change. However, spectra were taken after 1-hour incubation at 37° C. to ensure complete digestion.

As the figures show, all three labeled oligonucleotides have nearly identical absorption spectra in the visible wavelength range, indicating that the doubly labeled probe does not have dye aggregation, which is typically characterized by a significant alteration in the shape or profile of the absorption spectrum (See Example 7). The fact that the shape of the doubly labeled probe (FIG. 4A, Trace 29) and that of the digested probe (FIG. 4A, Trace 28) are similar is further evidence for the lack of dye dimer formation. The slight overall wavelength shift from Trace 29 to Trace 28, as opposed to a change in the shape of the absorption peak, is due to a difference in the microenvironment that surrounds the dye, similar to solvent effect. As one would expect, this "solvent effect" is similar for all three labeled oligonucleotides (Trace 28 vs. Trace 29 in FIG. 4A; Trace 30 vs. Trace 31 in FIG. 4B; and Trace 32 vs. Trace 33 in FIG. 4C).

Example 6

Amplification of GAPDH Monitored with a Homo-Doubly Labeled Probe and Two Singly Labeled Control Oligonucleotides The purpose of this experiment is to demonstrate that the superior performance of the probes according to the present invention is not due to any uniqueness of the dyes employed but the novel design of the probes. We synthesized three labeled oligonucleotides all having the same GAPDH probe sequence: 1) GAPDH oligo doubly labeled with 5-CR110 at 3' and 5' ends (SEQ ID No. 3, Table 1); 2) GAPDH oligo singly labeled with 5-CR110 at 5' end (SEQ. ID No. 10, Table 1); and 3) GAPDH oligo singly labeled with 5-CR110 at 3' end (SEQ ID. No. 11, Table 1). The labeled oligonucleotides were then tested for their utilities as potential probes for the amplification of a GAPDH gene fragment using condition identical to that in Example 3.

FIG. 4D shows the kinetic profiles of GAPDH gene amplification using the 3 labeled oligonucleotides as potential probes. The doubly labeled probe gave a typical kinetic profile (Trace 34 in FIG. 4D), whereas under the same amplification condition the two singly labeled oligonucleotides failed to respond to the amplification kinetics (Traces 35 and 36 in FIG. 4D). Successful gene amplifications for all three reactions were confirmed by agarose gel electrophoresis using ethidium bromide as the stain. Therefore, the lack of response from the singly labeled oligonucleotides is not caused by the absence of amplification products. These results suggest that the superior performance of the probes made according to various embodiments of the present invention are a result of the novel design of the probes. The improvements are not caused by the unique nature of the dyes or the manner at which an individual dye is attached to the oligonucleotides, or by the interaction between the dye and oligonucleotide.

Example 7

Spectral Comparison of Homo-Doubly Labeled Probes According to the Present Invention with Similar Molecular Beacon Probes Here we compare the absorption spectra of probes doubly labeled with a reporter dye according to the present invention with probes having a physically touching dye pair according to prior art. The purpose is to further demonstrate that unlike probes of prior art, doubly labeled probes of the present invention do not form dye aggregates.

A GAPDH stem-loop sequence having an amine group at the 3' and 5' ends respectively, 5'-(Am-$L_3$-) CCAAGCGGCTGAGAACGGGAAGCTTG GCTTGG(-$L_1$-Am)-3' was synthesized, where the underlined nucleotides indicate the stem-forming sequences. This amine-modified sequence was then used to synthesize three homo-doubly labeled molecular beacon probes by reacting with the succinimidyl esters of 6-CR110 (SEQ ID No 12, Table 1)), 6-TAMRA (SEQ ID No 13, Table 1) and 6-ROX (SEQ ID No 14, Table 1), respectively. Similarly, three corresponding homo-doubly labeled probes according to the present invention were made by reacting a double amine-modified sequence of (Am-$L_3$-) CAAGCTTCCC GTTCT-CAGC(-$L_1$-Am) with the succinimidyl esters of 6-CR110 ((SEQ ID No 21, Table 1), 6-TAMRA (SEQ ID No 22, Table 1) and 6-ROX (SEQ ID No 23, Table 1), respectively. The spectra of aforementioned stem-loop probes and their counterparts according to the present invention were measured at ~0.5 µM in 10 mM Tris buffer (pH 8.0) at 25° C. on a Shimadzu 1201 UV/Vis spectrophotometer. For easy comparison, spectra for each pair of a beacon probe and the corresponding probe of this invention were shown in FIGS. 5A, 5B and 5C, respectively. All homo-doubly labeled beacon probes showed a shorter wavelength shoulder peak, which indicates dye dimer formation (Blackman et al., 2002, Biochemistry, Packard et al., 1996, Proc. Natl. Acad. Sci.). On the other hand, probes of the present invention had spectra similar to those of singly labeled oligonucleotides or digested labeled oligonucleotides (See example 5)

Example 8

Signal Strength Comparison of Doubly Labeled Probes According to the Present Invention with Corresponding Homo-Doubly Labeled Beacon Probes This experiment demonstrates that homo-doubly labeled probes according to the present invention are several times more sensitive than the corresponding doubly labeled beacon probes.

A GAPDH gene fragment was amplified from a pTOPO plasmid containing GAPDH gene fragment (SEQ ID 24) using primers and conditions identical to that in Example 4. Each of the six probes from Example 7 (three homo-doubly labeled probes of this invention and the three corresponding beacon probes) was used to follow the amplification reaction at four different probe concentrations, 125 nM, 250 nM, 500 nM and 1 mM, respectively. Amplifications were performed in extra cycles to ensure all reactions are complete. In addition, gel-electrophoresis revealed that equal amount of amplified PCR products were formed for all three reactions. The kinetic profiles for each pair of a homo-doubly labeled probe of this invention and the related beacon probe are shown in FIGS. 6A, 6B and 6C respectively.

The data in FIGS. 6A, 6B and 6C clearly show that probes according to this invention are several fold more sensitive than the corresponding beacon probes when used at the same concentration. Also shown in the figures is that the beacon probes did not become fully saturated even at 1 mM concentration while the related probes of this invention displayed saturation at or near 250 nM. This delayed saturation is due to the equilibrium between the open and closed beacon conformations that makes only a fraction of the total amount of the probe available for hybridization with the target sequence at a given time (FIG. 7).

Example 9

Probes Labeled with a Mixture of FAM and CR110

This experiment demonstrates that oligonucleotides of the present invention can be labeled with a mixture of reporter dyes.

To synthesize a probe labeled with a single 6-FAM and a single 6-CR110, a double amine-modified GAPDH probe sequence of 5'-(Am-$L_3$-)CAAGCTTCCC GTTCTCAGC(-$L_1$-Am)-3' was reacted with a 1:1 mixture of 6-FAM SE and 6-CR110 SE. The labeling reaction produced four doubly labeled products: 1) 5'-(6-FAM-$L_3$-)CAAGCTTCCC GTTCTCAGC(-$L_1$-6-FAM)-3'; 2) 5'-(6-FAM-$L_3$-) CAAGCTTCCC GTTCTCAGC(-$L_1$-6-CR110)-3'; 3) 5'-(6-CR110-$L_3$-)CAAGCTTCCC GTTCTCAGC(-$L_1$-6-FAM)-3'; 4) 5'-(6-CR110-$L_3$-)CAAGCTTCCC GTTCTCAGC(-$L_1$-6-CR110)-3'. Products were purified by C18 RP HPLC and peaks corresponding to products 1) and 4) were identified by comparing the HPLC retention times of individually prepared products. Peaks that had retention times between those of product 1) and product 4) were assigned to those of the two hetero-doubly labeled probes, and fractions were collected and analyzed by UV/Vis spectroscopy. FIG. 8A shows the UV/Vis spectra of product 1) (Trace 80), products 2) and 3) (Trace 81) and product 4) (Trace 82). The spectrum of the hetero-doubly labeled probes (products 2) and 3)) falls in between those of the two homo-doubly labeled probes as one would have expected. The isolated probes were then used as probes for the amplification of the GAPDH gene under condition identical to that used in Example 4. FIG. 8B shows the kinetic profiles of GAPDH gene amplification using the isolated probes.

Alternatively, a hetero-doubly labeled oligonucleotide can be made via the traditional method for synthesizing FRET-based probes or primers by attaching the dyes in separate steps. However, the synthesis procedure described in this example may serve as a rapid way of screening for optimal dye pairs that may yield the best performance of the labeled oligonucleotides.

Example 10

Homo-Doubly Labeled Primers

These experiments demonstrate the use of oligonucleotides according to the present invention as fluorogenic primers for RT-PCR monitoring.

In a first experiment, a fluorogenic forward primer (5'-(5-CR110-L$_3$-)GAAGGTGMGGTCGGAGT (-L$_2$-5-CR110)C-3', SEQ No. 15, Table 1) for a GAPDH gene amplification was synthesized by reacting 5-CR110 SE with a diamine-modified primer 5'-(Am-L$_3$-)GAAGGTGAAGGTCGGAGT(-L$_2$-Am)C-3', wherein one amine is attached to the 5' phosphate via a C6 aliphatic linker and another amine attached to the base of No. 18 deoxynucleotide dT via a 10-atom aliphatic linker (See Example 1 for synthesis details). Amplification of the GAPDH gene was carried out using conditions identical to those used in Example 4 except that: 1) no probe was used; 2) the forward primer was replaced with the above homo-doubly labeled fluorogenic primer; and 3) three template copy numbers were used: one million, one thousand and zero (control). FIG. 9A shows the amplification profiles, where Traces 87, 88, and 89 represent one million, one thousand copies of templates and NTC, respectively.

In a second experiment, we synthesized another doubly labeled fluorogenic primer identical to the above forward fluorogenic primer except that the G at the very 5' end is omitted, (5'-(5-CR110-L$_3$-) AAGGTGAAGGTCGGAGT(-L$_2$-5-CR110)C-3', SEQ ID No 16, table 1). Similarly, PCR reactions were carried out using the same three template copy numbers as in the first experiment. FIG. 9B shows the amplification profiles, where Traces 90, 91, and 92 represent one million, one thousand and zero copies of templates, respectively. The result indicates that the successful application of the homo-doubly labeled primers according to the present invention is not due to G-nucleotide-associated fluorescence quenching/de-quenching, the working mechanism of the LUX primers (Nazarenko et al., 2002, *Nucleic Acid Research*)

In a third experiment, we synthesized a homo-doubly labeled reverse primer 5'-(5-CR110-L$_3$-)GAAGATGGT-GATGGGATT(-L$_3$ 5-CR110)TC-3' (SEQ No 17, Table 1) by reacting 5-CR110 SE with a diamine-modified reverse primer 5'-(Am-L$_2$-)GAAGATGGTGATGGGATT(-L$_2$Am)TC-3', wherein one amine is attached to the 5' phosphate via a C6 aliphatic linker and another amine attached to the base of No. 18 nucleotide dT via a 10-atom aliphatic linker. Similarly, the GAPDH gene was amplified using condition identical to that used in the first experiment except that 1) a regular forward primer was used and 2) the above homo-doubly labeled reverse primer was used. FIG. 9C shows the amplification profiles, where Traces 93, 94, and 95 represent one million, one thousand and zero copies of templates, respectively. The data from the first and second experiments indicates that either a forward primer or a reverse primer can be fluorogenically labeled according to the present invention for nucleic acid detection.

To exclude the possibility that the fluorescence quenching/dequenching of the homo-doubly labeled primers was caused by a difference in the interaction between the dye and the oligonucleotide before and after hybridization with the target, we synthesized two control primers, one with a single 5' end label (5'-(5-CR110-L$_3$-)GAAGGTGMG GTCGGAGTC-3', SEQ No 18, Table 1), and another with a single 5-CR110 attached to the base of No. 17 dT via a 10-atom linker (5'-(AAGGTGAAGG TCGGAGT(-L$_2$-5-CR110)C)-3', SEQ No 19, Table 1). As FIGS. 9D and 9E show, neither the 5'-end labeled primer (Trace 97 in FIG. 9D) nor the dT-labeled primer (Trace 99 in FIG. 9E) responded to the PCR reaction, although gel electrophoresis of the end products revealed that both PCR reaction proceeded normally.

In still another control experiment, we synthesized a singly labeled forward primer with the dye 5-CR110 attached to the No. 18 dT nucleotide via a 10-atom flexible linker (5'-GAAG-GTGAAGGTCGGAGT(-L$_2$-5-CR110)C-3', SEQ No 20, Table 1). This primer did respond positively to the amplification reactions as it was incorporated into PCR product, similar to the homo-doubly labeled primers in experiments 1) and 3). A possible explanation for this observation is that the dG nucleotide at the very 5' end may loop over to the 3' end to quench the fluorophore as in the case of LUX primers (FIG. 9F). To test this hypothesis, we synthesized a singly labeled forward primer with the 5'-end dG removed (5'-AAGGT-GAAGGTCGGAGT(-L$_2$-5-CR110)C-3', SEQ No 19, Table 1). As shown in FIG. 9E, this primer failed to respond to the amplification reaction. This result, along with the result from the second experiment in this example, indicates that in the absence of nucleotide G-associated fluorescence quenching/de-quenching fluorogenic oligonucleotides of the present invention require at least two reporter dyes.

Example 11

SNP Typing with a Pair of Homo-Doubly Labeled Probes

Tapp et al have shown SNP typing by using a pair of TaqMan probes, each labeled with FAM and TET respectively for C to T transition of the estrogen receptor gene in codon 10. This experiment demonstrates a pair of AllGlo probes, labeled with CR110 or R6G, in replacement of FAM and TET respectively work equally well for this purpose.

SNP typing reactions were carried out in 20 µl reactions containing 10 mM Tris (pH 8.0), 50 mM KCl, 3.5 mM MgCl$_2$, 2 mM each of dNTP, 1 unit of AmpliTaq Gold (ABI, Foster City, Calif.), 0.5 µM forward primer 5'-CCACGGACCAT-GACCATGA-3' (SEQ ID No. 26), 0.5 µM reverse primer 5'-TCTTGAGCTGCGGACGGT-3' (SEQ ID No. 27), 0.2 µM ERcodon10C probe, 5'-(6-CR110-L$_3$-CCAAAGCATC CGGGATGGCC(-L$_1$-6-CR110)-3' (SEQ ID No. 28), 2 µM ERcodon10T probe, 5'-(5-R6G-L$_3$-CCAAAGCATC TGGGATGGCC (-L$_1$-5-R6G)-3' (SEQ ID No. 29), and model plasmid DNA to be typed. The reaction profile was set at 95° C. for 7-minutes followed by 50 cycles of 15 second at 95° C. and 20 second at 60° C. Fluorescence was measured at the 60° C. step simultaneously from both FAM and TET channels. The homozygote CC model genotype consists of 10$^6$ copies of a plasmid pER(C), a pTOPO plasmid containing an 10$^6$ bp insert flanking the codon10 of estrogen receptor gene, where the SNP is C (SEQ ID No. 30); the homozygote TT model genotype consists of 10$^6$ copies of a plasmid pER (T), a pTOPO plasmid containing an 106 bp insert flanking the codon10 of estrogen receptor gene, where the SNP is T (SEQ ID No. 31); the hoterozygote CT genotype consist of 0.5×10$^5$ copies of pER(C) and 0.5×10$^5$ copies of pER(C). The three genotypes exhibited three distinct amplification profile patterns, these patterns are a follows: Homozygote CC had a high CR110 signal (Trace 131, FIG. 10A) and very low R6G signal (Trace 132, FIG. 10A); Homozygote TT has low CR110 signal (Trace 135, FIG. 10C) and high R6G signal (Trace 136, FIG. 10C); Heterozygote CT has mid-level CR110 signal (Trace 133, FIG. 10B) and mid-level R6G signal (Trace 134, FIG. 10B).

Example 12

Amplification Using an Exo⁻ DNA Polymerase

This experiment demonstrates the use of an exo⁻ DNA polymerase in real time PCR where the fluorescent signal was monitored by hybridization instead of cleavage of the probes. The amplifications were performed in 20 µl reaction solution containing premixed buffer and Titanium Taq (BD Biosciences, Mountain View, Calif.). A HCV gene fragment (SEQ ID 32) in pTOPO plasmid was amplified with 2 µM forward primer 5'-GCACGAATCCTAAACCTCAAAA-3' (SEQ ID No. 33), 0.2 µM reverse primer 5'-GGCAACAAGT-MACTCCACCAA-3' (SEQ ID No. 34). A doubly 6-ROX-labeled HCV probe, 5'-(6-ROX-$L_3$-ATCTGACCACCGC-CCGGGAAC-(-$L_1$-6-ROX)-3' (SEQ ID No. 35) at final 0.5 µM was used for each of the reactions. The thermal regimen was set at 95° C. for 2 minutes followed by 50 cycles of 15-second duration at 95° C., 20-second duration at 60° C. and 5 second duration at 72° C. Fluorescence was measured at the 60° C. step. A series of 10-fold dilutions of the template was made to create titration curves of the amplification plot. FIG. 12 shows amplification plots of aforementioned reactions starting with $10^6$ copies of template (Trace 140) down to 1 copy of the template (Trace 146). An NTC (no template control, Traces 148) is also shown in the figure. The inset shows that the Ct value is reversibly correlated with the logarithm of starting copy number (Trace 148).

All publications, patents, and patent applications cited in this specification are incorporated herein by reference as if each individual publication, patent, or patent application was specifically and individually indicated to be incorporated by reference and set forth in its entirety herein.

Unless specifically identified to the contrary, all terms used herein are used to include their normal and customary terminology. Further, while various embodiments of diagnostic tests and medical treatment devices having specific components and steps are described and illustrated herein, it is to be understood that any selected embodiment can include one or more of the specific components and/or steps described for another embodiment where possible.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. And while the invention was illustrated using specific examples, and theoretical arguments, protein and DNA sequences, accounts and illustrations these examples, arguments, illustrations sequences, accounts and the accompanying discussion should by no means be interpreted as limiting the invention. The Abstract of the Disclosure is included for the convenience of the persons searching for the document; the Abstract is not a summary of the invention it should not be used to interpret or to limit the claims or specification.

---

What is claimed is:

1. A probe comprising a nucleic acid sequence, said sequence having a 5' end and a 3' end, wherein the 3'end is blocked to prevent extension via polymerization, and wherein the nucleic acid sequence is labeled with only two spectrally similar or identical fluorophores, wherein a first fluorophore is attached to a first site of said probe and a second fluorophore is attached to a second site of said probe, the first site and the second site being separated from one another by about 3 to about 60 nucleotides, and wherein said probe exhibits a random coil conformation when unhybridized with a target polynucleotide and yields an increase in detectable emission from the first fluorophore and the second fluorophore upon separation of the first or the second fluorophore from said probe.

2. The probe according to claim 1, wherein said probe further includes at least one cleavage site located between the two fluorophores attached to said probe.

3. The oligonucleotide probe according to claim 1, wherein the two fluorophores attached to said probe are separated from one another by 3 to 35 nucleotides.

4. The probe according to claim 1, wherein the two fluorophores attached to said probe are separated from one another by about 12 to about 35 nucleotides.

5. The probe according to claim 1, wherein absorption wavelengths of the two fluorophores are within 15 nm.

6. The probe according to claim 1, wherein the fluorophores are selected from the group consisting of a dye that has delocalized positive charge, a dye that has a delocalized negative charge, and a dye that has an equal number of positive and negative charges.

7. The probe according to claim 1, wherein said probe has a 5'-end and a 3'-end, wherein the first fluorophore is attached to the 5'-end of said probe, and wherein the second fluorophore is attached to the 3' end of said probe.

8. The probe according to claim 7, further including at least a first flexible aliphatic linker and a second aliphatic linker, wherein the first fluorophore is attached to the first linker and the first linker is attached to the 5'-end of said probe, and the second fluorophore is attached to the second linker, and the second linker is attached to the 3' end of said probe.

9. The probe according to claim 1, wherein said labeled probe is suitable in a polynucleotide amplification reaction performed at a temperature of about 56° C. or higher.

10. The probe according to claim 9, wherein said polynucleotide amplification reaction is selected from the group consisting of PCR, multiplex PCR, real time PCR, quantitative PCR, and real time quantitative PCR.

11. A method of labeling a probe having a 5'end and a 3'end, wherein the 3'end is blocked to prevent extension via polymerization, wherein said probe is labeled with two spectrally similar or identical fluorophores, said method comprising:

attaching a first fluorophore to a first site of said probe sequence and a second fluorophore to a second site of said probe sequence, the first site and the second site being separated from one another by about 3 to about 60 nucleotides, thereby labeling said probe, such that said probe sequence exhibits a random coil conformation when unhybridized with a target polynucleotide and yields an increase in detectable emission from the first fluorophore and the second fluorophore upon separation of the first or the second fluorophore from said probe.

12. The method of labeling a probe according to claim 11, wherein the two fluorophores attached to said probe are separated from one another by about 3 to about 35 nucleotides.

13. The method of labeling a probe according to claim 11, wherein the two fluorophores attached to said probe are separated from one another by about 12 to about 35 nucleotides.

14. The method of labeling a probe according to claim 11, wherein absorption wavelengths of the two fluorophores are within 15 nm.

15. The method of labeling a probe according to claim 11, wherein at least one of the fluorophores is selected from the group consisting of a dye that has delocalized positive charge, a dye that has a delocalized negative charge, and a dye that has an equal number of positive and negative charges.

16. The method of labeling a probe according to claim 11, further including:

adding a plurality of flexible aliphatic linkers including a first linker and a second linker, wherein the first fluorophore is attached to the first linker, and the first linker is attached to the 5'-end of said probe, and the second fluorophore is attached to the second linker, and the second linker is attached to the 3'-end of said probe.

17. A kit for labeling a probe, the kit comprising:
a probe, said probe having a random coil conformation when unhybridized with a target polynucleotide, a length of at least 7 nucleotides and including at least a first site and a second site, said probe having a 5' end and a 3' end, wherein the 3' end is blocked to prevent extension via polymerization;
two spectrally similar or identical fluorophores each having a reactive group, wherein a first fluorophore is reactive for attaching to the first site of said probe, and a second fluorophore is reactive for attaching to the second site of said probe such that the first fluorophore and the second fluorophores attached to said probe are separated from one another by about 3 to about 60 nucleotides, and wherein said probe when labeled yields an increase in detectable emission from the first fluorophore and the second fluorophore upon separation of the first or the second fluorophore from said probe.

18. The kit for labeling a probe according to claim 17, wherein at least one of the two fluorophores is selected from the group consisting of a dye that has a delocalized positive charge, a dye that has a delocalized negative charge, and a dye that has an equal number of positive and negative charges.

19. A method of using a probe comprising the steps of:
supplying a sample of a target nucleic acid; and
hybridizing a probe of claim 1 to the target nucleic acid.

20. The method of using an probe according to claim 19, wherein said sample is selected from the group consisting of tissue extract, cell extract, bodily fluid, in vitro nucleic acid synthesis reaction, and PCR reaction mixture.

21. The method of using a probe according to claim 19, wherein said labeled probe is used in a nucleic acid amplification reaction wherein the reaction is selected form the group consisting of PCR, multiplex PCR, real-time PCR, quantitative PCR, and real-time quantitative PCR.

22. The method of using a probe according to claim 19, wherein said probe is for identifying the presence of a target sequence of nucleic acid polymer in the sample.

23. The method of using a probe according to claim 19, wherein said sample is applied to a nucleic acid chip and said nucleic acid chip includes said labeled probe.

24. The probe according to claim 6, wherein the dye having the delocalized positive charge is a cyanine dye.

25. The probe according to claim 6, wherein the dye having an equal number of positive and negative charges is a rhodamine dye.

26. The probe according to claim 7, wherein the fluorophores are identical.

27. The probe according to claim 9, wherein the fluorophores are identical.

28. The probe according to claim 1, wherein emission wavelengths of the two fluorophores are within 15 nm.

29. The probe according to claim 1, wherein the first or second fluorophore is a xanthene dye.

30. The probe according to claim 1, wherein the first or second fluorophore is a cyanine dye.

31. The probe according to claim 1, wherein the probe yields an increase in detectable emission from the fluorophores, which correlates with the amount of target polynucleotide amplified in an amplification reaction.

32. A kit comprising the probe of claim 1.

33. A kit according to claim 17, wherein the two spectrally similar or identical fluorophores are of different types of fluorophores.

34. A kit according to claim 33, wherein the two different types of fluorophores are selected from the group consisting of a dye that has a delocalized positive charge, a dye that has a delocalized negative charge, and a dye that has an equal number of positive and negative charges.

35. The method of claim 11, wherein the fluorophores are identical.

36. The kit of claim 32 comprising reagents for nucleic acid amplification and a polymerase possessing 5'-exonuclease activity.

37. The kit of claim 17 further comprising an instruction manual for carrying out said labeling of said probe.

38. The probe of claim 1 wherein said probe is complementary to a region of the target polynucleotide.

39. The probe of claim 1 wherein at least one of the two spectrally similar fluorophores is a non-sulfonated dye.

40. The probe of claim 38 wherein the two spectrally similar fluorophores are non-sulfonated dyes.

41. The probe of claim 38 or 39 wherein the non-sulfonated dye is a xanthene dye.

42. The method of claim 38 or 39 wherein the non-sulfonated dye is a cyanine dye.

* * * * *

UNITED STATES PATENT AND TRADEMARK OFFICE
CERTIFICATE OF CORRECTION

PATENT NO. : 7,667,024 B2
APPLICATION NO. : 10/993625
DATED : February 23, 2010
INVENTOR(S) : Fei Mao and Xing Xin It is certified that error appears in the above-identified patent and that said Letters Patent is hereby corrected as shown below:

On the title page Item (*) Notice: delete "by 166 days" insert --by 229 days--

On the title page, Item (60), replace "60/253,263" with "60/523,263"

At column 47, line 44, replace "The oligonucleotide probe" with "The probe"

At column 49, line 30, replace "an probe" with "a probe"

At column 49, line 36, replace "selected form" with "selected from"

Signed and Sealed this

Fourteenth Day of September, 2010

David J. Kappos
*Director of the United States Patent and Trademark Office*